(12) United States Patent
Kim et al.

(10) Patent No.: US 12,364,961 B2
(45) Date of Patent: Jul. 22, 2025

(54) MULTIPLEX SYNTHESIS METHOD OF COMPOUND LIBRARY AND PARALLEL SYNTHESIZER OF COMPOUND LIBRARY USING SAME

(71) Applicant: POSTECH Research and Business Development Foundation, Pohang-si (KR)

(72) Inventors: Dong Pyo Kim, Pohang-si (KR); Gwang Noh Ahn, Anyang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 828 days.

(21) Appl. No.: 17/527,280

(22) Filed: Nov. 16, 2021

(65) Prior Publication Data
US 2022/0219133 A1    Jul. 14, 2022

(30) Foreign Application Priority Data
Jan. 13, 2021    (KR) .................... 10-2021-0004589

(51) Int. Cl.
*B01J 19/00*    (2006.01)
*C40B 50/08*    (2006.01)

(52) U.S. Cl.
CPC .......... *B01J 19/0046* (2013.01); *C40B 50/08* (2013.01); *B01J 2219/00313* (2013.01); *B01J 2219/00355* (2013.01); *B01J 2219/00479* (2013.01); *B01J 2219/00495* (2013.01); *B01J 2219/00587* (2013.01); *B01J 2219/0072* (2013.01)

(58) Field of Classification Search
CPC .......... B01J 19/0046; B01J 2219/00281; B01J 2219/00299; B01J 2219/00313; B01J 2219/00353; B01J 2219/00355; B01J 2219/00479; B01J 2219/00495; B01J 2219/00587; B01J 2219/0072; C40B 60/14
See application file for complete search history.

(56) References Cited

U.S. PATENT DOCUMENTS

2002/0048536 A1*  4/2002  Bergh ................... B01L 3/5025
                                                    422/640
2018/0311638 A1*  11/2018  Jensen ................... B01J 19/004

FOREIGN PATENT DOCUMENTS

KR    10-2003-0092043    12/2003
KR    10-2020-0126819    11/2020

OTHER PUBLICATIONS

KIPO, Office Action of KR 10-2021-0004589 dated Jul. 18, 2022.

* cited by examiner

*Primary Examiner* — Lessanework Seifu
(74) *Attorney, Agent, or Firm* — LEX IP MEISTER, PLLC

(57) ABSTRACT

The present invention relates to a parallel synthesis method and synthesizer of a compound library, and more specifically provides a parallel synthesis method and synthesizer of a compound library, which uniformly distribute a first reactant and perform independent reactions in separate spaces, and since it is possible to confirm the results for various reaction variables at once, the synthesis time of the compound library can be reduced with a high synthesis yield of the product.

10 Claims, 64 Drawing Sheets

| Design parameter | Design condition | Design parameter | Design condition |
|---|---|---|---|
| $D_{In}$ | 2.4 mm | $n$ | 16 |
| $D_{Mixer}$ | 5 mm | $D_{Capillary}$ | 0.75 mm |
| $D_{Damper1}$ | 81 mm | $L_{Capillary}$ | 1,500 mm |
| $D_{Damper2}$ | 43 mm | $V_{Mixer}$ | 0.77 mL |
| $L_{Mixer}$ | 50.11 mm | $V_{Damper}$ | 9.6 mL |
| $L_{Baffle}$ | 1.25 mm | $V_{Junction}$ | 5.2 mL |
| $L_{Damper1}$ | 2.5 mm | $V_{Capillary}$ | 39.3 mL |
| $L_{Damper2}$ | 1.15 mm | | |

FIG. 14

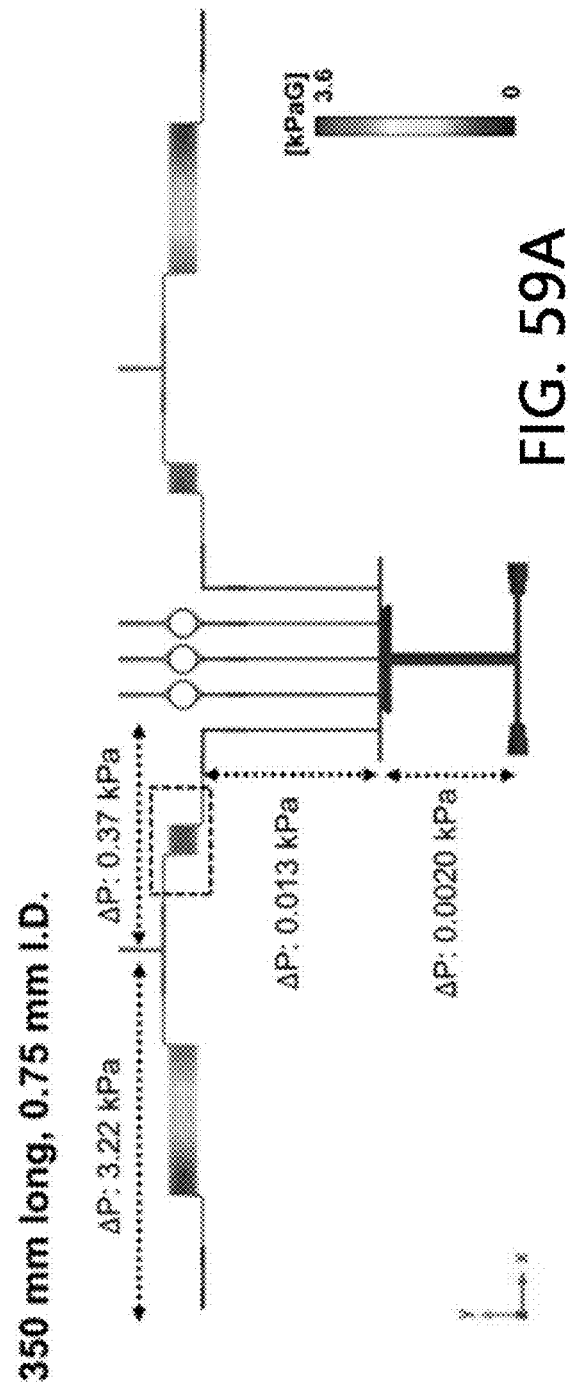

MULTIPLEX SYNTHESIS METHOD OF COMPOUND LIBRARY AND PARALLEL SYNTHESIZER OF COMPOUND LIBRARY USING SAME

CROSS-REFERENCE TO RELATED APPLICATION

This application claims priority to and the benefit of Korean Patent Application No. 10-2021-0004589, filed on Jan. 13, 2021, the disclosure of which is incorporated herein by reference in its entirety.

TECHNICAL FIELD

The present invention relates to a parallel multiplex synthesis method of a compound library and a parallel synthesizer of a compound library, and more specifically relates to a parallel synthesis method and synthesizer of a compound library, which enables efficient synthesis of a compound library by distributing a specific reagent into a plurality of accommodation spaces and simultaneously performing several types of reactions in parallel.

BACKGROUND ART

Optimization and screening of variables related to a chemical reaction is the most important issue that has troubled the synthetic community throughout the history. Currently, the synthetic community mostly relies on commercially available batch synthesizers for quick screening of solvents, reaction temperatures, reagents and concentrations for maximizing the product yield and purity. These batch parallel synthesizers usually require simultaneous processing and handling of a large number of reaction flasks on a single platform in order to precisely control individual reaction parameters in multiple flasks.

Recently, novel screening approaches have been attempted using micro-well platforms in a high-throughput combinatorial manner, and this is for screening additive combinations for organic reactions. In 2015, an approach of handling reagents in nanoliter volumes using a micro-titer plate system in batch mode was devised to improve the efficiency of optimization in the early stages of all of the natural product or drug discovery programs. In this context, it can be seen that there is a need to develop innovative fusions of synthesis and screening in order to save time and run multiple experiments simultaneously.

Continuous flow techniques have received much attention due to their better reproducibility, high selectivity and control over various reaction parameters compared to batch. Moreover, continuous flow techniques are replacing routine batch synthesis with the development of "universal" automated flow synthesis platforms for the efficient optimization of organic synthesis. This emergence marks a significant step forward in the search for drug discovery, either through the effective development of Computer-Aided Synthesis Planning (CASP) or through robotically-executed target- or diversity-directed flow synthesis of specific molecules. This approach can significantly improve productivity and screening techniques by reducing the time and space required for chemical processes. In addition, on-demand small molecule synthesis, the use of reconfigurable systems and commercially available arrays of multi-reactor modules extend flow chemistry to new horizons. Despite all of these sophisticated advances, the overall technology transformation from continuous flow to rapid optimization and screening for routine workflows in the laboratory is not yet useful.

On the other hand, most of the reported flow platforms perform single or multi-step transformations in a sequential manner based on linear or radial approach, allowing only certain types of reactions or combinations, such as $Ai \times Bj$, to be tested at a time, thereby limiting the speed of the overall process. Nevertheless, research on flow parallel synthesizers for multiplex parallel synthesis and chemical screening that can perform multiple reactions has not been reported, and thus, the situation is that research thereon is necessary.

DISCLOSURE

Technical Problem

The technical problem to be solved by the present invention is to provide a multiplex synthesis method and a parallel synthesizer for the simultaneous synthesis of a compound library.

In addition, the present invention is directed to providing a parallel synthesizer including a distributor capable of uniformly distributing a reactant.

Another object of the present invention is to provide a parallel synthesizer of a compound library in which reactants are distributed to perform independent reactions.

Technical Solution

In order to solve the above problems, the inventors of the present invention tried to develop the maximum potential of a user-friendly flow parallel synthesizer. As such, the present invention provides a multiplex synthesis method of a compound library and a parallel synthesizer of a compound library using the same.

The parallel synthesis method of a compound library according to the present invention may include a) introducing a first reactant at a controlled flow rate to be distributed into a plurality of accommodation spaces, b) introducing a second reactant into each of the plurality of accommodation spaces to mix with the first reactant, and c) after each independent chemical reaction is performed in the accommodating space, discharging the product of the chemical reaction through a discharge unit on one side of the accommodation space.

As the plurality of accommodation spaces are independent and configured in parallel, the concentration of the second reactant and the temperature and time of the chemical reaction may be set differently for each accommodation space.

The first reactant of step a) may be distributed in equal amounts into a plurality of accommodation spaces through a flow distributor.

The accommodation space may include a reactor in which the first reactant and the second reactant are mixed; and a duct connected to the reactor to transport the first reactant to the reactor. The reactor may be in the form of a T-mixer.

In addition, according to a preferred exemplary embodiment of the present invention, the flow distributor may include a baffle and a damper, and the damper may uniformly control the flow distribution of the first reactant by using the baffle.

According to another exemplary embodiment of the present invention, the first reactant may be an aryldiazonium salt, and the aryldiazonium salt may include a cation represented by Chemical Formula 1 below.

[Chemical Formula 1]

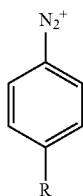

In Chemical Formula 1 above, R is hydrogen, a hydroxyl group, an ether group, a halogen atom, a carbonyl group, a nitro group, a naphthyl group, a cyano group, an amino group, an amidino group, hydrazine, hydrazone, a carboxyl group, a sulfonic acid group, a phosphoric acid group, an alkyl group having 1 to 12 carbon atoms, an alkenyl group having 1 to 12 carbon atoms, an alkynyl group having 1 to 12 carbon atoms, an aryl group having 6 to 10 carbon atoms, or an arylalkyl group having 7 to 10 carbon atoms.

The second reactant is a substance for chemically reacting with the first reactant, and the type thereof may be the same or different for each accommodation space.

In the multiplex synthesis method of a compound library according to the present invention, as indicted in FIG. 2, instead of sequentially performing several AixBj type reactions, one action activates many combinations such as Ai×(B1, B2, B3 . . . Bn) in multiple modes The multiplex synthesis method of the present invention also enables efficient chemical development by allowing chemists to screen for reaction variables to derive optimal values for temperature, solvents, catalysts, loading amounts, reaction equivalence and concentration parameters.

Due to the unique properties of microfluidics, the multiplex synthesis method of a compound library according to the present invention and the parallel synthesizer using the same can simultaneously perform reactions at various time scales and various reaction combinations (refer to FIGS. 1 and 2). The present invention provides a parallel synthesizer for a library of metal-based compounds to quickly and efficiently investigate reagents, reaction conditions and molecular spaces to unlock the chemical space that can aid the workflow of early discovery chemistry.

The parallel synthesizer of a compound library according to the present invention may include a first inlet unit through which a first reactant is introduced and at least one inlet is formed, a flow distributor connected to the first inlet unit and distributing the introduced first reactant in equal amounts, and formed with a damper and a baffle, a plurality of ducts connected to the flow distributor and through which the distributed first reactant passes, respectively, a second inlet unit located at one side of the duct and formed with an inlet through which a second reactant is introduced, a plurality of reactors respectively connected to the duct and in which a product is generated by a chemical reaction of the first reactant and the second reactant transported through the duct, and a discharge unit formed on one side of the reactor to discharge the product, and the damper may be adjusted such that the first reactant is distributed in equal amounts.

According to an exemplary embodiment of the present invention, the duct and the plurality of reactors may be configured in the form of coiled capillaries.

In addition, the plurality of reactors may be independently controlled such that chemical reactions occur under different conditions. For example, the concentration of the second reactant introduced into each of the reactors may be adjusted, and the temperature and time of the chemical reaction may be independently controlled. The plurality of reactors may include a temperature control unit, and the temperature control unit may include a heating device or a cooling device. As the heating device or cooling device according to the present invention, devices commonly used in a compound synthesizer may be used.

According to an exemplary embodiment of the present invention, the duct of the present invention may have a higher hydraulic pressure than the reactor. In this case, in order to increase the hydraulic pressure of the duct, the diameter of the capillary duct may be configured to be smaller and the length of the duct may be configured to be longer (Comparing FIG. 59A and FIG. 59A, the pressure on the right side of the baseline was higher in FIG. 59B than in FIG. 59A). The duct may have a smaller diameter and a longer length than the reactor. The flow velocity in the duct may be 0.3 to 0.5 mL/min, and preferably, 0.3 to 0.4 mL/min.

Referring to FIGS. 59 and 60, unlike the reactant (DMSO) injected through the first inlet unit at a flow velocity of 5.28 mL/min, the reactant (DMSO) may be supplied through each second inlet unit at different flow velocities on the linear graph (±50% difference based on 0.33 mL/min (0.165 to 0.495 mL/min)). When the hydraulic pressure of the duct is low as shown in FIG. 60A, the flow velocity in each duct connected to the flow distributor changes in inverse proportion to the change according to the flow velocity in the second inlet unit, and the flow velocity in the discharge unit is maintained at a constant level.

When the hydraulic pressure of the duct is high as shown in FIG. 60B, the flow velocity in the discharge unit is proportional to the flow velocity in the second inlet unit such that the flow velocity in each duct connected to the flow distributor is constant regardless of the difference in the flow velocities in the second inlet unit. It can be seen that when the hydraulic pressure of the duct is configured to be higher than the hydraulic pressure of the reactor as shown in FIG. 60B, the flow velocity in each duct connected to the flow distributor and the flow velocity in the discharge unit are separated. In FIG. 60, in both cases of FIG. 60A and FIG. 60B, the MF values of the duct and the MF values of the discharge unit were (a) 30.7% and 2.6% and (b) 1.8% and 15.7%, respectively.

That is, when the hydraulic pressure of the duct was configured to be low as shown in FIG. 60A, if the flow velocities of each of the plurality of second inlet units were different from each other, the flow velocity in the discharge unit was maintained constant, and the flow velocity in the duct decreased as the flow velocity in the connected second inlet unit was higher. On the other hand, when the hydraulic pressure of the duct was configured to be high as shown in FIG. 60B, the flow velocity in the discharge unit was proportional to the flow velocity in the second inlet unit, and even though the flow velocities of each of the plurality of second inlet units were different from each other, the flow velocity in the duct maintained a relatively constant flow velocity regardless of the flow velocity of the connected second inlet unit. Referring to the fact that the constant flow velocity of the duct is closely related to the flow rate distribution, when the hydraulic pressure of the duct is configured to be higher (than the reactor), the flow velocity in the discharge unit is proportional to the flow velocity in the second inlet part, and the flow velocity of the duct is maintained relatively constant, and thus, it can be seen that the flow rate of the first reactant is uniformly distributed in each of the plurality of ducts.

According to a preferred exemplary embodiment of the present invention, the first inlet unit and the second inlet unit may include a pump, and the pump may introduce a reactant into an inlet.

According to another exemplary embodiment of the present invention, a syringe pump or a peristaltic pump may be used as the pump, but is not limited thereto.

In the duct, a peristaltic pump may be installed at a position connected to the flow distributor to adjust the injection flow rate of the first reactant into the duct, and accordingly, the residence time in the reactor may be individually adjusted. The first reactant may include an aryldiazonium salt, and the aryldiazonium salt may include a cation represented by Chemical Formula 1 below.

[Chemical Formula 1]

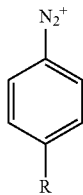

In Chemical Formula 1 above, R is hydrogen, a hydroxyl group, an ether group, a halogen atom, a carbonyl group, a nitro group, a naphthyl group, a cyano group, an amino group, an amidino group, hydrazine, hydrazone, a carboxyl group, a sulfonic acid group, a phosphoric acid group, an alkyl group having 1 to 12 carbon atoms, an alkenyl group having 1 to 12 carbon atoms, an alkynyl group having 1 to 12 carbon atoms, an aryl group having 6 to 10 carbon atoms, or an arylalkyl group having 7 to 10 carbon atoms.

In addition, the second reactant is a substance for chemically reacting with the first reactant, and the type thereof may be the same or different for each duct introduced therein.

The parallel synthesizer of a compound library of the present invention is equipped with a reservoir-type flow distributor, a duct and a reactor (preferably 16 microreactor capillaries), and is configured to simultaneously perform several types of reactions in parallel under various reaction conditions including photochemistry.

According to a preferred exemplary embodiment of the present invention, for the reaction based on the first reactant (preferably a diazonium salt) as a test case, in order to create a compound library under optimal conditions obtained by multiplex screening of different reaction variables (preferably 96 or more), the first reactant may be distributed into a plurality of (preferably 16) ducts through which various second reactants (building blocks) are supplied to explore chemical reactions at various reaction times, temperatures and concentration modes. Therefore, the present invention demonstrates the efficiency of the parallel synthesizer of a compound library by enabling the multiplex formation of various C—C, C—N, C—X and C—S bonds, and when using an aryl diazonium salt as a reactant (first reactant), numerous aryl diazonium chemical compounds (preferably 24 or more aryl diazonium chemical compounds) may be optimized including extended tests by converting various aryl diazonium salt derivatives (preferably at least two diazonium salt derivatives). In particular, the function of the parallel synthesizer of a compound library according to the present invention is implemented without reconfiguration of the equipment at a low manufacturing cost.

The parallel synthesizer of a metal-based compound library according to the present invention (refer to FIGS. 3 and 4) is an assembly of several modules with specific functions. The system consists of an inlet unit located at the bottom, a flow distributor with built-in baffle discs, coiled capillary (preferably 16 or more) ducts and reactors (microreactors) and a discharge unit connected thereto. The reactor (preferably coiled capillary) may be combined with a heating device for independent temperature control of individual reactions, which is proved by IR imaging at two different temperatures, 75° C. and 100° C. (refer to FIG. 10). All components were modeled using a computer-aided design (CAD) program as shown in FIG. 3A.

FIG. 3A is a block diagram of the parallel synthesizer of a compound library according to the present invention, and FIG. 3B is a photograph of the synthesizer. Referring to FIG. 3, the reagent injected into the two inlets at the bottom is uniformly distributed upward through a reservoir-type distributor, and continuously merged with various second reactants (building blocks) in the reactor (preferably T-mixer).

FIG. 4 shows a schematic diagram of the cross-sectional layout and detailed dimensions of a metal-based parallel flow platform along (a) the x-y plane and (b) the x-z plane, and 16 capillaries and a discharge unit are present at the top in which specific locations are numbered.

FIG. 5A is a piping and instrumentation diagram of the parallel synthesizer of a compound library according to the present invention, and FIG. 5B is an image of a metal-based parallel synthesizer for the simultaneous synthesis of an aryldiazonium library according to an exemplary embodiment. Referring to FIG. 5, the aryl diazonium reagent is injected into the reactor system through continuous pumps D1 and D2, and is distributed into 16 capillaries through a flow distributor, and the second reactant (building block) reagent is introduced by syringe pumps I1 to I8 and peristaltic pumps I9 to I16. In addition, peristaltic pumps P1 to P3 may be used to individually control the residence time of the corresponding capillaries.

Specifically, the parallel synthesizer of a compound library is operated in the following order. A solution including a reactant is sequentially injected into the first inlet units D1 and D2 located opposite to the bottom of the system through a liquid pump, and a washing solution is also injected and purified after the reaction sequence is completed. The injected solution passes through an upward flow channel, gradually filling the flow distributor equipped with an optimally designed fluid damper and baffle disc, and is evenly distributed into 16 individual capillaries. The distributed solution (solution including the first reactant) chemically reacts in parallel with the second reactants (building blocks) introduced through each inlet (the second inlet units, I1 to I16) in each reactor (T-mixers, M1 to M16).

According to an exemplary embodiment of the present invention, peristaltic pumps P1 to P3 may be installed to selectively adjust the residence time individually in three capillaries. The system shows a uniform flow distribution in the capillaries R4 to R16 regardless of the change in the flow rates of the remaining capillaries R1 to R3. This is a phenomenon that occurs due to the predominantly acting gravity of a system based on a damper with a baffle structure, which creates a passively driven buffering effect.

In the present invention, CFD analysis was performed in the system based on the modeling generated through the 3D CAD program (refer to FIGS. 6, 8 and 9, Tables 2 and 3). The method of fabricating the parallel synthesizer of a compound library was selected in consideration of the design characteristics, precision, cost and production time of each module. As a result, baffle discs with a complex structure were manufactured by 3D metal printing, and other large and simple parts that require high precision were manufactured by the computer numerical control (CNC) machining. The fabricated modules were assembled with stainless-steel capillaries and pumps using combined-type, T-type and bendable Swagelok connectors, rendering the complete setup of the parallel synthesizer of a metal-based compound library as shown in FIG. 3(b). The flow performance of the parallel synthesizer was evaluated by comparing the CFD numerical analysis and the flow experiment of the fabricated system (refer to FIGS. 6 to 9, Tables 2 and 3). The uniformity of the flow distribution was confirmed by quantifying the maldistribution factor (MF) value, which is the standard deviation of the average mass flow rate in 16 capillaries. As a result, the theoretical MF values at various flow velocities were simulated to be less than 1%, whereas the experimental MF values measured by collecting the amount of DMSO solvent were less than 4% (refer to FIG. 6 and Table 1). A low MF value indicates a uniform flow distribution between the capillaries. The reservoir-type distributor also maintains a uniform motion of the flow velocity in the remaining capillaries, even when clogged in single or multiple capillaries. In addition, the input flow rate may be adjusted during channel clogging to restore the desired optimum flow rate for uniform chemical performance without process interruption.

In particular, compared to the existing flow reactor system, the present invention has an advantage that a gradient flow profile is not formed despite clogging of the channel (FIG. 8 and Table 2). In addition, it was confirmed numerically and experimentally that it is possible to use different flow velocities individually by using a separate pump in some of the 16 reactors, and the remaining reactors maintain a uniform flow distribution such that multiplex synthesis is possible under the conditions of different reaction times and temperatures (FIG. 9).

The present invention may be used for the flow parallel synthesis and parameter screening of an aryl diazonium chemical library.

Diazo groups have broad and adjustable reactivity. The chemical diversity of aryldiazonium chemistry makes it referred to as a transport hub for aryl groups by acting as a $N_2^+X^-$ functional group called "super electrophile" or a good leaving group. Thus, diazo groups may react with nucleophiles such as hydrogen, oxygen, nitrogen, halogen, sulfur and carbon via the ionic or radical pathway to form almost any type of bonds. Moreover, various functionalization methods may be important models for the generation of diverse chemical libraries that can serve as a screening for the preparation of new chemical substances or a lead for drug discovery or as a starting material for subsequent reactions.

Advantageous Effects

By using the multiplex parallel synthesis method and parallel synthesizer of the present invention, it is possible to enable efficient chemical development by screening for reaction variables to select optimal parameters in temperature, solvents, catalysts and loading stoichiometry and concentrations.

DESCRIPTION OF DRAWINGS

FIG. 14 is a chart showing the products and synthesis yields according to the type of reactants.

FIGS. 59A and 59B are comparative mimetic diagrams when the length and diameter of the duct are configured differently according to an exemplary embodiment of the present invention. FIG. 59A is a mimetic diagram when the duct is configured to have a length of 350 mm and a diameter of 0.75 mm, and FIG. 59B is a mimetic diagram when the duct is configured to have a length of 1,500 mm and a diameter of 0.375 mm.

FIG. 60A is a graph when the duct is configured to have a length of 350 mm and a diameter of 0.75 mm, and FIG. 60B is a graph when the duct is configured to have a length of 1,500 mm and a diameter of 0.375 mm.

MODES OF THE INVENTION

Figure 1:
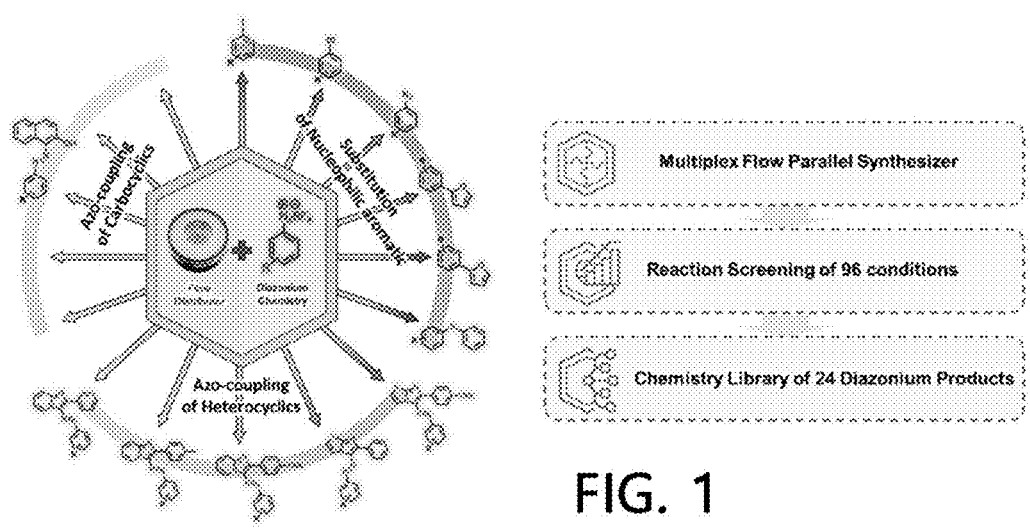
FIG. 1 is an image schematically illustrating a reaction process according to an exemplary embodiment of the present invention.
Figure 2:
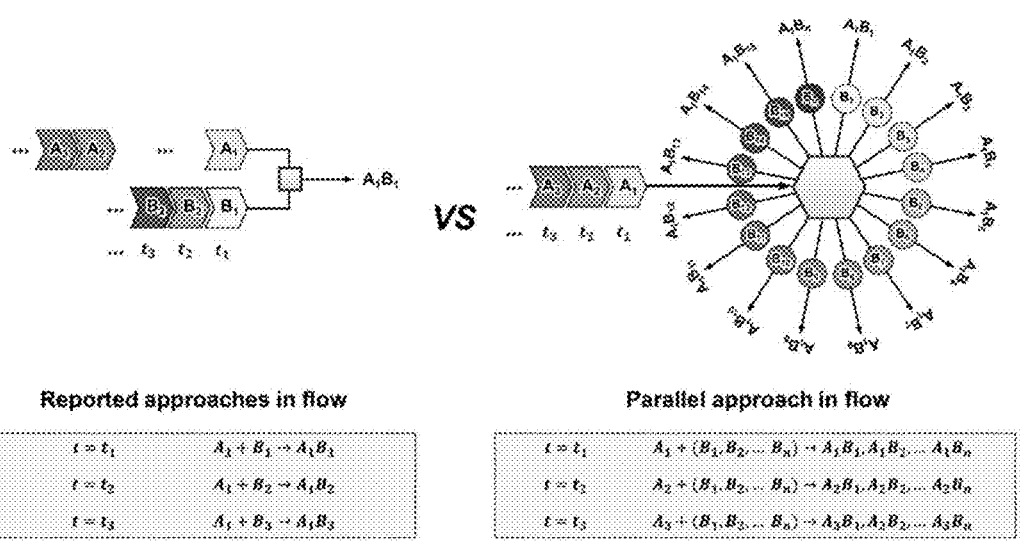
FIG. 2 is a mimetic diagram comparing a known approach of a flow system and the flow parallel synthesis method according to an exemplary embodiment of the present invention.

The inventors of the present invention designed and developed the first flow parallel synthesizer in order to perform multiplex synthesis and optimization of complex libraries. In the present invention, numerical analysis and experimental verification were performed in order to confirm the reliable flow distribution performance of the flow parallel synthesizer in various flow velocities, concentrations, temperatures and clogging cases.

In addition, by using the synthesizer (platform), the present invention simultaneously optimized various aryl diazonium salt-based reactions on small-molecule building blocks in reaction parameters with well-controlled reaction times and concentrations. As a result, the aromatic substitution reaction (C—C, C—N, C—X and C—S bonds) and the azo-coupling reaction based on carbocycles and heterocycles were simultaneously screened for 96 different conditions, and as a result of selecting reaction variables, the optimal conditions were obtained within 1 hour. Based thereon, multiplex synthesis of 12×2 compounds was demonstrated on a single flow platform. From an academic and industrial point of view, particularly in the pharmaceutical field from laboratory to commercialization, the synthesizer of the present invention can minimize the time, labor and capital investment associated with hit-to-lead optimization success rates.

Hereinafter, the present invention will be described in detail through the Examples and Experimental Example.

Example 1

Experimental Method

All reagents and solvents were used as commercial grades. All reactions were performed in a flow parallel synthesizer or in a single capillary reactor. Parts for constructing the flow parallel synthesizer were purchased from IDEX Health & Science LCC. The tube connecting the pump and platform consisted of high-purity PFA and PTFE tubing (1/16' O.D., 0.75 mm I.D.) and polyether ether ketone ¼ 4-28 nuts. Swagelok tube fittings (SS-100-1-1, SS-600-1-2, SS-100-3 and SS-100-9) were purchased from Swagelok. Stainless-steel capillaries of 1/16" O.D and 0.75 mm I.D were connected to the main body of the distributor via Swagelok connectors. O-rings (SM9-4D, heat-resistant fluororubber, 8.5 pi O.D. and 1.5 mm thick) were purchased from Misumi Korea. Reagents were injected using SGE glass syringes (SGE Analytical Science) or PHD Ultra syringe pumps (Harvard Apparatus) equipped with constant flow gradient HPLC piston pumps (PrimeLine™ and Scientific Systems Inc.). For individual heating of the capillaries, the temperature system was configured as follows.

A k-type thermocouple from Omega Engineering Korea was connected to the NX2 PID (Proportional-Integral-Differential)-based temperature controller from HANYOUNG NUX, and the output value according to the current temperature of the capillary reactor was fed back. The output value was converted into a high-voltage current flowing into a cartridge-type rod heater from Super Heat by WYU-DG 25 SI, which is a thyristor power regulator from Woonyoung Co., Ltd. All reactions were monitored by thin layer chromatography (TLC) on Merck silica gel 60-F254-coated 0.25 mm plates detected by UV. Flash chromatography was performed on silica gel (particle size 0.064 to 0.210 mm) with the indicated solvents. The reported yields were for isolated and spectroscopically pure compounds. 1H and 13C NMR spectra were recorded on Bruker-500 MHz and Bruker-300 MHz instruments using TMS as an internal standard. Chemical shifts were provided in ppm ($\delta$) with reference to tetramethylsilane (TMS, $\delta$=0.00 ppm) or residual $CHCl_3$ peak ($\delta$=7.27 ppm) for 1H NMR and 13C-resonance ($\delta$=77.0 ppm) of $CDCl_3$ for 13C NMR as internal standards. Data was presented as chemical shifts, multiple (s=singlet, d=doublet, t=triplet, m=multiples, b=broad, respectively) coupling constants (J, Hz) and integrals.

Example 2

Fabrication and Assembly of Flow Parallel Synthesizer

Metal 3D printing was performed using a Direct Metal Laser Sintering printer (DMLS, ProX DMP320, 3DS Systems Inc.) with an accuracy of 50 μm. SUS630 17-4PH stainless steel powder was used for 3D printing. For CNC machining, machining of SUS316L was performed using a CTX Beta 1250 TC machine from DMG MORI. The CNC machine provides positioning accuracy within 6 μm and repeatability within 2 μm. The individually manufactured parts were joined without leaks by placing polymer O-rings between the assembled parts. The inlet unit/discharge unit tubes and stainless-steel capillaries were connected to the junctions of the main body of the distributor, inlet unit or discharge unit via union-type, T-type and bend-type Swagelok connectors. Microreactors based on stainless-steel capillaries (1/16" O.D., 0.75 mm I.D.) were space efficient by bending the capillary around a cylindrical spool (11 mm I.D., 1.6 mm pitch). The position of the baffle in the fluid damper was set at a height ratio of 1:2 between the upper and lower spaces, and the porosity value of the baffle was 0.5, which was optimized for distribution performance.

Example 3

Computational Fluid Dynamics Simulation Setup

The fluid flow throughout the synthesizer, including the distributor and capillaries, may be described by the incompressible Navier-Stokes equation along with the mass conservation equation. Assuming steady state, the governing equations for fluid flow used in the present invention may be simplified as follows.

$$\rho v \cdot \nabla v = -\nabla p + \mu \nabla^2 v + \rho g: \quad \text{Navier-Stokes equation} \quad (1)$$

$$\nabla \cdot v = 0: \quad \text{Mass conservation equation} \quad (2)$$

The $\rho$ is the fluid density, v is the fluid linear velocity, p is the pressure, $\mu$ is the fluid dynamic viscosity, and g is the gravitational acceleration. The governing equations are generally solved with appropriate boundary conditions where the outlet is set to atmospheric pressure. The corresponding flow conditions were imposed in the case of a discharge unit forced by periodic pumps. Non-slip boundary conditions for velocity and concentration were applied to the wall boundary. For boundary conditions, the physical properties of DMSO (1.1004 g·cm$^{-3}$, 1.996 cP at 20° C.) were imposed as conditions. The equations were discretized based on the finite volume method, and the commercially available numerical software COMSOL (COMSOL, INC.) was used for numerical simulation.

Example 4

Computational and Experimental Fluid Dynamics of Flow Parallel Synthesizer

The flow performance of the parallel synthesizer according to the present invention was evaluated through numerical analysis of computational fluid dynamics (CFD) and preliminary flow experiments of the fabricated system. The uniformity of the flow distribution was quantified using a maldistribution factor (MF).

$$MF(\%) = \sqrt{\frac{1}{n-1} \sum_{k=1}^{n} \left( \frac{m_i - \overline{m}}{\overline{m}} \right)^2} \times 100 \quad (3)$$

In the above mathematical formula, n is the number of capillaries, and mi is the mass flow rate of the $i^{th}$ capillary. The $\overline{m}_i$ represents the average mass flow rate of each capillary. Consequently, the MF value is the standard deviation of the mass flow rate in each capillary. Therefore, a low MF value indicates a uniform flow distribution between the capillaries.

Figure 6:
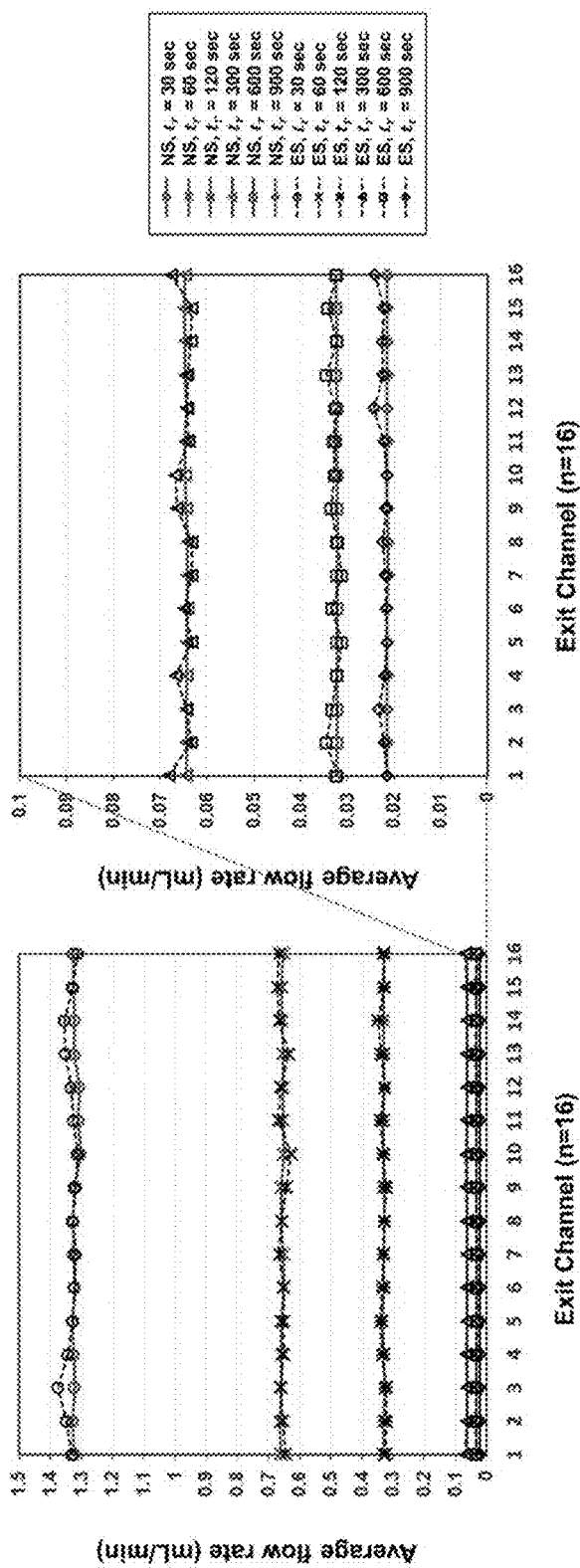
FIG. 6 is a graph showing the flow velocity in a discharge unit according to an exemplary embodiment of the present invention.

FIG. 6 is a graph comparing flow rates in the studies of experimental (black line) and numerical analyses (red line) of 16 discharge units under various flow conditions. DMSO was injected through the first inlet unit (D1 or D2) at flow velocities of 10.56, 5.28, 2.64, 1.06, 0.53 and 0.35 mL/min, respectively. Building blocks were injected through inlets I1 to I16 at flow velocities of 0.66, 0.33, 0.17, 0.066, 0.033 and 0.022 mL/min in each case. The MF values obtained through the experimental and numerical studies are shown in Table 1 below.

TABLE 1

MF values obtained through experimental and numerical studies for 16 outlets under various flow rate conditions

| Flow Velocity (mL/min) | D1 or D2 | 10.56 | 5.28 | 2.64 | 1.06 | 0.53 | 0.35 |
|---|---|---|---|---|---|---|---|
| | I1~I16 | 0.66 | 0.33 | 0.17 | 0.066 | 0.033 | 0.022 |
| Residence Time (s) | | 30 | 60 | 120 | 300 | 600 | 900 |
| Numerical Study, MF (%) | | 0.54 | 0.59 | 0.53 | 0.51 | 0.22 | 0.25 |
| Experimental Study, MF (%) | | 1.27 | 1.85 | 2.27 | 2.61 | 3.06 | 3.86 |

Figure 5A:
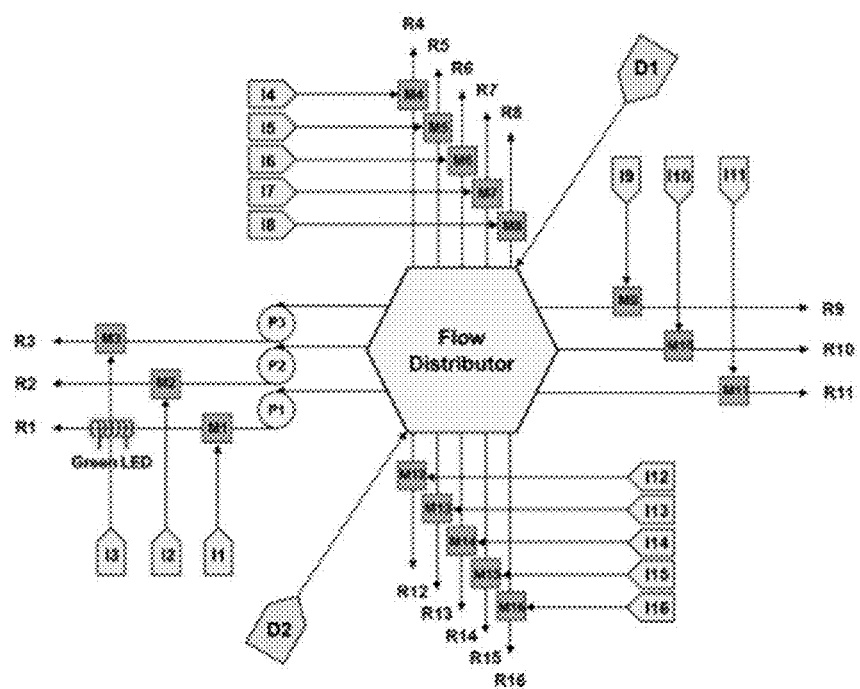
FIG. 5A is a schematic diagram of the parallel synthesizer according to the flow of reactants.
Figure 5B:
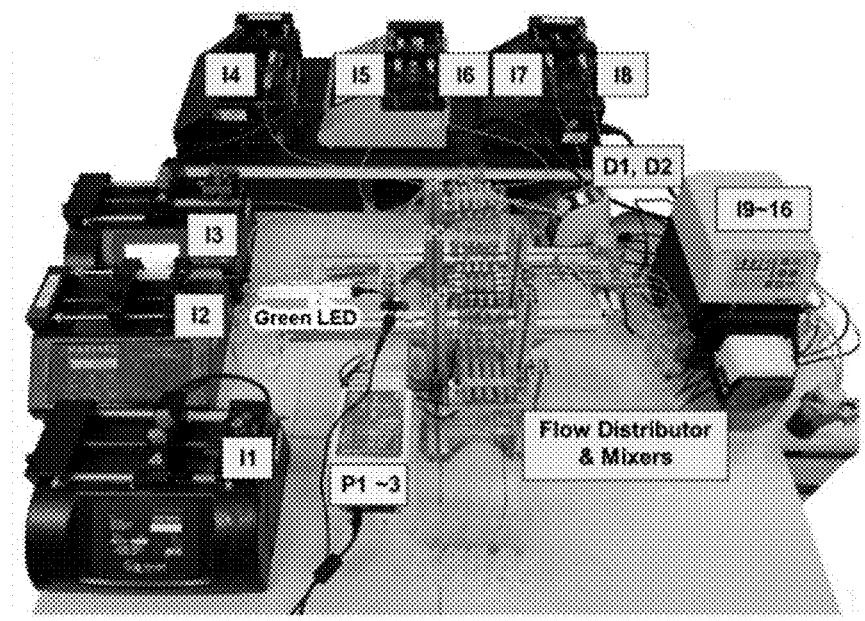
FIG. 5B is an image of the parallel synthesizer according to an exemplary embodiment.

CFD numerical analysis and flow distribution experiments were performed under the assumption that a uniform flow distribution was required in all capillaries in order to screen for the yields of individual reactions under various residence time conditions. A DMSO solution was injected through the first inlet unit (D1 or D2 in FIG. 5) at flow velocities of 6 cases (10.56, 5.28, 2.64, 1.06, 0.53 and 0.35 mL/min). In this case, the peristaltic pumps (P1 to P3) were selectively disconnected. The boundary conditions of I1 to I16 were set such that the flow including the second reactant (building block) was coupled through the second inlet at flow velocities of 6 cases (0.66, 0.33, 0.17, 0.066, 0.033, and 0.022 mL/min). In this case, the volume of each capillary was 0.662 mL, and thus, the residence times in each capillary were 30, 60, 120, 300, 600 and 900 seconds. Finally, the outlet flow velocities were checked in 16 individual capillaries and the MF values were obtained to quantify the uniformity of flow. In the numerical and experimental results, the MF values were sufficiently low at less than 1% and 4%, respectively. Clogging which is a chronic problem of microreactors may occur in some suboptimal organic reactions.

Figure 7A:
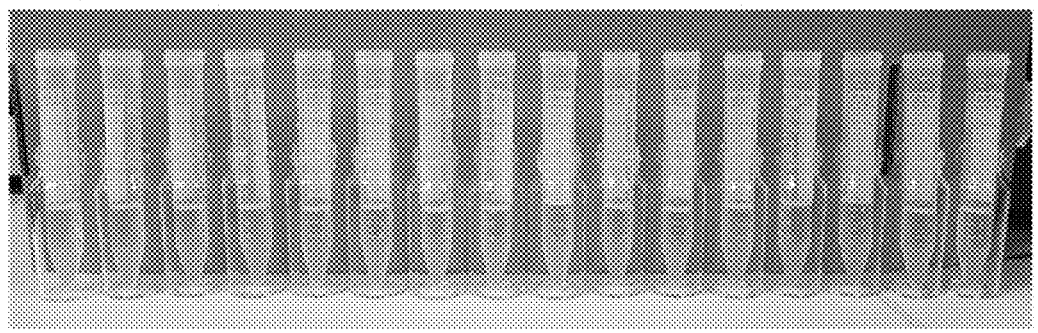
FIGS. 7A and 7B are images comparing the amounts of products synthesized by the parallel synthesizer.
Figure 7B:
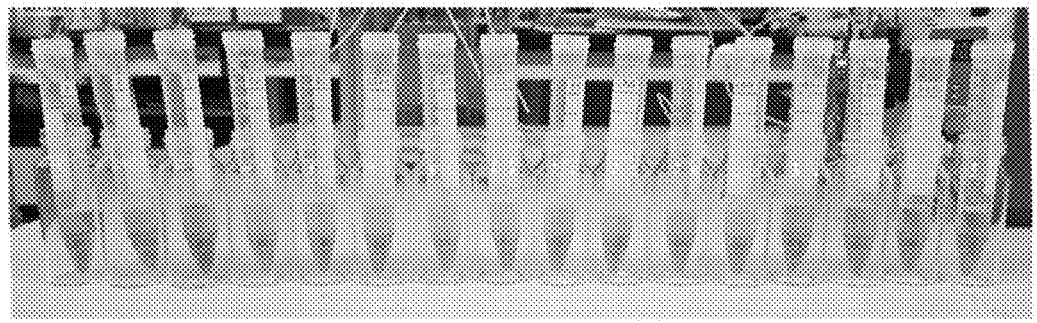

In the present invention, when two types of liquids were separately injected at a flow velocity of 10.56 mL/min through the first inlet units D1 and D2, 16 sample vials collected from R1 to R16 were visualized to experimentally confirm the uniform flow distribution of the flow parallel synthesizer (refer to FIG. 7). In FIG. 7A, only the DMSO solvent was used, and in FIG. 7B, a diazonium salt solution at 0.77 M (mixed with DMSO) was used. The inventors of the present invention investigated the effect of clogging, which occurred in one of the capillaries (R12 to R16), on the other capillaries (FIG. 7 and Table 1). As a result, as indicated in FIG. 7 and Table 1, the MF values of the remaining capillaries except for the clogged capillary showed a uniform flow distribution of less than 3% numerically or experimentally.

Next, simulations were performed by providing various capillaries with varying residence times for the simultaneous synthesis of a compound library under optimized conditions. It was assumed that the solution was injected through the first inlet unit (D1 or D2 in FIG. 5) at a flow velocity of 5.14 mL/min. In order to reflect changes in the flow velocities of the three capillaries through the peristaltic pumps P1 to P3, the boundary conditions of the outlet flow before the T-mixer for the three outlet capillaries were set at flow velocities of 0.022, 0.17 and 0.66 mL/min, respectively. The flow of the second reactant (building block) to the three capillaries I1 to I3 was also set at flow velocities of 0.044, 0.17 and 0.66 m/min, respectively. For the other capillaries, boundary conditions were set for I4 to I16 such that a flow velocity of 0.33 mL/min was merged through each T-mixer. Finally, the flow distribution was quantified by checking the outlet flow rates of the remaining 13 capillaries except for 1 to 3 capillaries (FIG. 8).

Figure 8A:
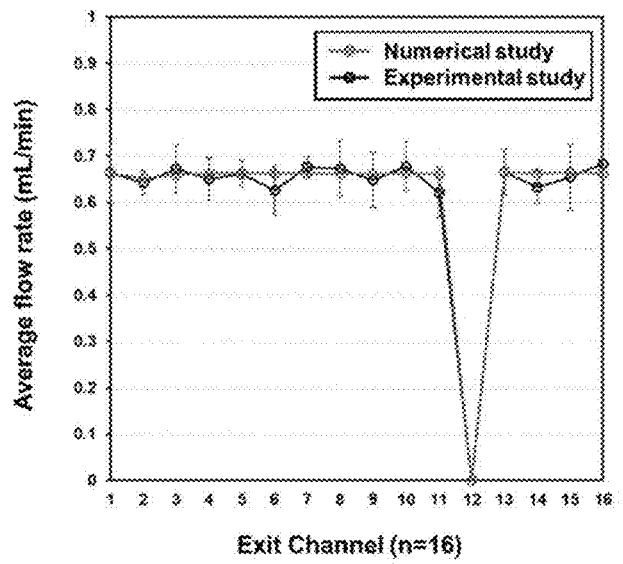
FIGS. 8A, 8B and 8C are comparative graphs of the flow velocities appearing when a specific capillary is clogged according to an exemplary embodiment of the present invention.
Figure 8B:
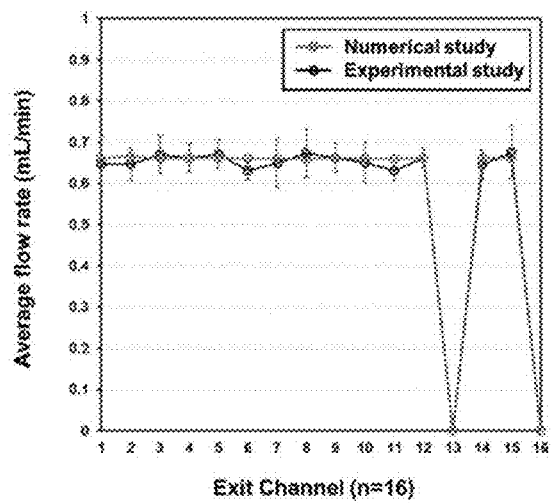
Figure 8C:
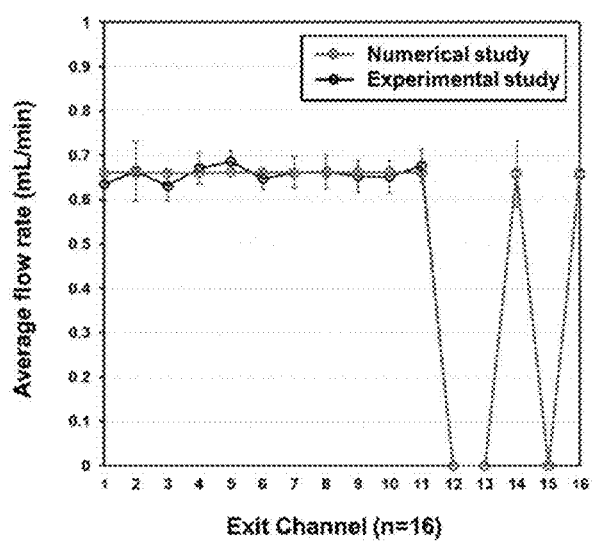

FIG. 8 is an experimental and numerical analysis graph of flow distribution for various cases of clogging. FIG. 8A shows the flow velocity distribution during clogging in R12 when the total flow velocity passing through D1 and D2 was 4.95 m/min, and the flow velocity of all the second inlet units except I12 was 0.33 m/min. FIG. 8B shows the distribution of flow velocities when clogged in two reactors R13 and R16 when the total flow velocity was 4.62 mL/min and the flow velocity of all the second inlet units except I13 and I16 was 0.33 mL/min. Referring to (c) of FIG. 8, when the total flow velocity was 4.29 m/min and the flow velocity of all the second inlet units except I12, I13 and I15 was 0.33 mL/min, it shows the distribution of flow velocities when three reactors R12, R13 and R15 were clogged. Referring to FIG. 8, it can be seen that an even flow velocity distribution appeared overall except for the capillaries in which the clogging occurred. The MF values obtained through the experimental and numerical studies are summarized in Table 2 below.

TABLE 2

MF values obtained from experimental and numerical studies of clogging in three different cases.

| Case | (a) | (b) | (c) |
|---|---|---|---|
| Numerical Study, MF (%) | 0.47 | 0.22 | 0.04 |
| Experimental Study, MF (%) | 2.96 | 2.25 | 2.31 |

Figure 9:
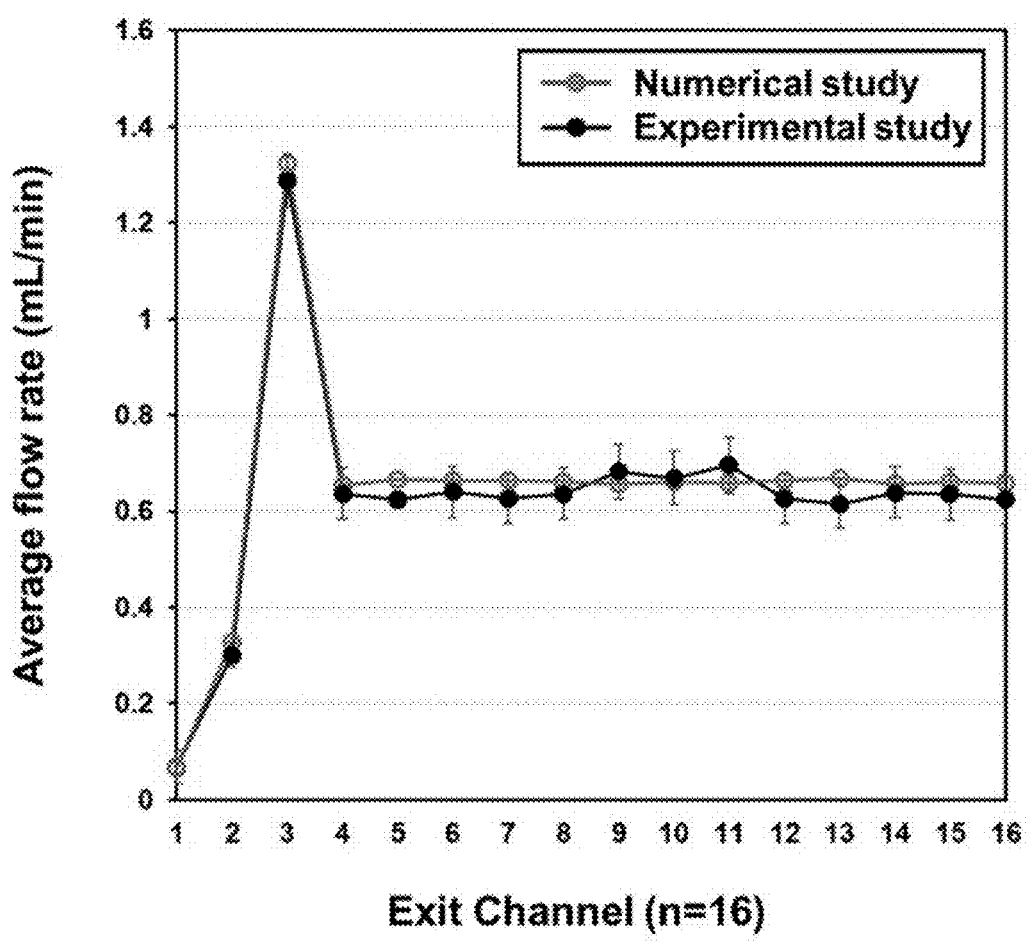
FIG. 9 is a graph showing the flow velocities when the speed in a capillary is changed using a pump at a specific second inlet unit according to an exemplary embodiment of the present invention.

Through numerical analysis, the calculated MF value was less than 1% in the flow distribution of outlets except for outlets R1 to R3. According to this, it can be seen that even when the flow velocities of capillaries 1 to 3 were selectively changed through the peristaltic pumps P1 to P3, the flow rate distribution of the other capillaries except for the above was maintained uniformly. In addition, it can be seen that the experimentally confirmed MF value was less than 4%, indicating that the flow distribution was sufficiently uniform. FIG. 9 is a graph comparing the experimental (black) and numerical (red) flow rate data of 16 discharge units, assuming parallel flow synthesis when reactors R1 to R3 were individually controlled at different flow velocities (0.033, 0.16, 0.66 mL/min) by three peristaltic pumps. In this case, DMSO was injected through D1 and D2 at a flow velocity of 5.14 mL/min and through the second inlet units of I1 to I3 (0.033, 0.16, 0.66 mL/min) to merge at a 1:1 ratio. Referring to FIG. 8, the numerical MF values of R4 to R16 were 0.57, which was slightly higher than the experimental MF value of 3.37.

Example 5

Figure 10:
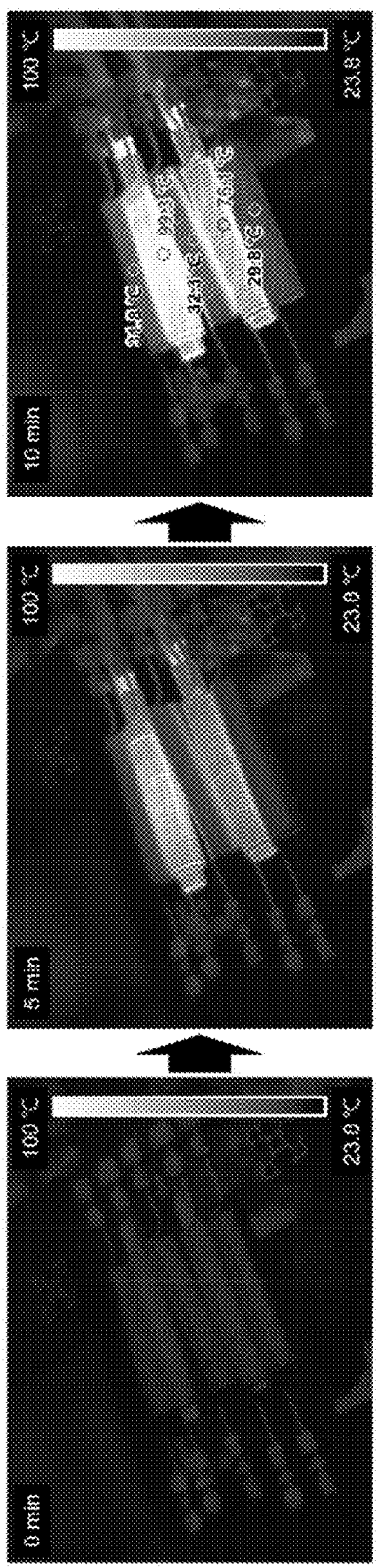
FIG. 10 is an IR photo image observed by varying the speed in each reactor.

Individual Control of Reactions Through Temperature Control of Capillary Including Duct and Reactor Referring to the IR image (plan view) of FIG. 10, it can be seen that only two coiled reactors were controlled and heated in the flow parallel synthesizer according to the present invention. The corresponding temperatures were set at 100° C. (R13) and 75° C. (R15) using a Proportional-Integral-Differential (PID)-based thermostat, thermocouple and heating rod. R13 and R15 reached the setpoint stably in a short period of time (10 min), while the other reactors (coiled capillary) in the vicinity remained stable at room temperature, and for better temperature control, it is suggested to fill the space (1 mm) between the reactors with a sufficient insulating material.

Example 6

Synthesis of Starting Reagents in Batch
6-1. General Procedure for the Synthesis of Aryl Diazonium Tetrafluoroborates Salt

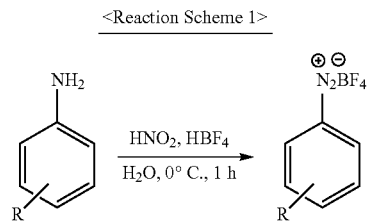

<Reaction Scheme 1>

The appropriate aniline (214.75 mmoles, 20 g, 1 equiv.) was dissolved in a mixture of 86 mL of distilled water and 57 mL of 48 wt. % hydrofluoroboric acid. After the reaction mixture was cooled to 0° C. using an ice bath, a sodium nitrite (15.6 g in 32 mL) solution was added dropwise every 5 minutes. The resulting mixture was stirred for 1 hour, and the precipitate was collected by filtration and redissolved in a minimum amount of acetone. Diethyl ether was added until diazonium tetrafluoroborate was precipitated, and afterwards, it was filtered, washed several times with diethyl ether, and dried under vacuum.

6-2. General Procedure for the Synthesis of Imidazopyridine and Imidazothiazole

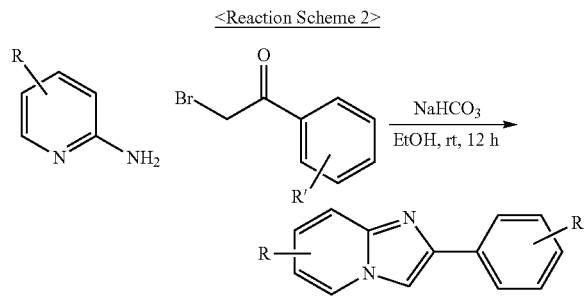

<Reaction Scheme 2>

A solution of 2-aminopyridine/2-aminothiazole (5 mmol, 1 equiv.) and bromomethyl ketone 30 (5 mmol, 1 equiv.) in EtOH (30 mL) was heated at reflux for 16 hours, and the reaction progress was monitored using TLC. The solvent was removed under reduced pressure and a saturated NaHCO₃ solution (30 mL) was added to the remaining solid. Afterwards, the mixture was extracted with EtOAc (30 mL, ×3) and after the organic layers were combined, it was dried over $Na_2SO_4$. The concentrated crude product was dried under vacuum overnight and then triturated with (4:1) EtOAc:n-hexane to obtain prude imidazopyridine/imidazothiazole, and it was used directly in the next step.

Example 7

Synthesis of Starting Reagents of Diazonium Salt in Batch—SNAr-Type Reactions of Diazonium in Batch The diazonium salt was used as a first reactant and injected through the first inlet unit, and the following reaction was performed in each reactor.

7-1. Iodination Reaction

The diazonium salt (738 mg, 3.85 mmol) was dissolved in 9 mL of DMSO. After the reaction mixture was cooled to 20° C., a solution of potassium iodide (640 mg, 3.85 mmoles) dissolved in 1 mL of $H_2O$ was added dropwise to generate nitrogen gas, and the mixture was stirred for 30 minutes. The progress of the reaction was monitored by GC. Subsequently, the product was diluted with water and extracted three times with ether. The organic layer was washed with brine, dried over $Na_2SO_4$ and evaporated under reduced pressure. The resulting compound was absorbed on silica gel and purified through column chromatography (n-pentane/n-hexane, 1:1) to obtain iodobenzene as a colorless liquid in 70% yield.

7-2. Chlorination Reaction

The diazonium salt (738 mg, 3.85 mmol) was dissolved in 8 mL of DMSO. After the reaction mixture was cooled to 20° C., a solution of CuCl (518 mg, 3.85 mmoles) dissolved in 2 mL of HCl was added dropwise to generate nitrogen gas, and the reaction mixture was stirred for 30 minutes. The progress of the reaction was monitored using GC. Subsequently, the product was diluted with water and extracted three times with ether. The organic layer was washed with brine, dried over $Na_2SO_4$ and evaporated under reduced pressure. The resulting compound was absorbed on silica gel and purified by column chromatography (n-pentane/n-hexane, 1:1) to obtain chlorobenzene as a colorless liquid in 64% yield.

7-3. Azidation Reaction

The diazonium salt (738 mg, 3.85 mmol) was dissolved in 9 mL of DMSO. After the reaction mixture was cooled to 20° C., a solution of sodium azide (250 mg, 3.85 mmoles) dissolved in 1 mL of $H_2O$ was added dropwise to generate nitrogen gas, and the mixture was stirred for 30 minutes. The progress of the reaction was monitored by GC. Subsequently, the product was diluted with water and extracted three times with ether. The organic layer was washed with brine, dried over $Na_2SO_4$ and evaporated under reduced pressure. The resulting compound was absorbed on silica gel and purified through column chromatography (n-pentane/n-hexane, 1:1) to obtain azidobenzene as a pale-yellow liquid in 89% yield.

7-4. Synthesis of Diaryl Sulfides

The diazonium salt (738 mg, 3.85 mmol) was dissolved in 4 mL of DMSO. the reaction mixture was cooled to 20° C., and a solution of p-thiocresol (478 mg, 3.85 mmoles) and NaOH (154 mg, 3.85 mmoles) dissolved in 6 mL of DMSO:$H_2O$ (2:1) was added dropwise with lead to generate nitrogen gas, and the mixture was stirred for 2 hours. The progress of the reaction was monitored by TLC. Subsequently, the product was diluted with water and extracted three times with ether. The organic layer was washed with brine, dried over Na$_2$SO$_4$ and evaporated under reduced pressure. The resulting compound was absorbed on silica gel and purified through column chromatography (n-hexane/ethyl acetate, 98:2) to obtain diaryl sulfides as a colorless liquid in 60% yield.

7-5. α-Arylation of Furan

The diazonium salt (738 mg, 3.85 mmol) was dissolved in 9 mL of DMSO. After the reaction mixture was cooled to 20° C., a solution of furan (5.6 mL, 77 mmoles) and 4-aminomorpholine (0.193 mmoles, 5 mol %) dissolved in 10 mL of DMSO was added dropwise to generate nitrogen gas, and the mixture was stirred for 30 minutes. The progress of the reaction was monitored by TLC. Subsequently, the product was diluted with water and extracted three times with ether. The organic layer was washed with brine, dried over Na$_2$SO$_4$ and evaporated under reduced pressure. The resulting compound was absorbed on silica gel and purified through column chromatography (n-hexane/ethyl acetate, 98:2) to obtain α-arylated furan as a colorless liquid in 55% yield.

7-6. Photochemical Reactions for α-Arylation of Furan

The diazonium salt (738 mg, 3.85 mmol) and furan (38.5 mmol) were dissolved in 10 mL DMSO, and Eosin Y (0.193 mmol, 5 mol %) was added thereto, and then, the reaction mixture was stirred under a green LED for 2 hours, and the progress of the reaction was monitored by using TLC. Subsequently, the product was diluted with water and extracted three times with ether. The organic layer was washed with brine, dried over Na$_2$SO$_4$ and evaporated under reduced pressure. The resulting compound was absorbed on silica gel and purified through column chromatography (n-hexane/ethyl acetate, 98:2) to obtain α-arylated furan as a colorless liquid in 61% yield.

7-7. Arylation of Imidazopyridine/Imidazothiazole in Batch

The diazonium salt (738 mg, 3.85 mmol) and imidazopyridine/imidazothiazole (2.55 mmol) were taken together and dissolved in 10 mL of DMSO, and the reaction mixture was stirred at room temperature for 8 hours, and the progress of the reaction was monitored by using TLC. Subsequently, the product was diluted with water and extracted 3 times with ethyl acetate. The organic layer was washed with brine, dried over Na$_2$SO$_4$ and evaporated under reduced pressure. The resulting compound was absorbed on silica gel and purified through column chromatography (n-hexane/ethyl acetate, various ratios).

7-8. Azo-Coupling of Diazonium Salts and β-Naphthol in Batch

The diazonium salts (6.375, 5.1, 3.825, 3.1875 and 2.55 mmol, respectively) were dissolved in 10 mL of DMSO in 5 different vials. After the reaction mixture was cooled to 20° C., a solution of β-naphthol and NaOH (6.375, 5.1, 3.825, 3.1875 and 2.55 mmol, respectively) dissolved in 10 mL of DMSO:H$_2$O (9:1) was added dropwise, and the mixture was stirred for 1 hour, and then, the progress of the reaction was monitored by using TLC. Subsequently, the product was diluted with water and extracted three times with ethyl acetate. The organic layer was washed with brine, dried over Na$_2$SO$_4$ and evaporated under reduced pressure. The resulting compound was absorbed on silica gel and purified by column chromatography (n-hexane/ethyl acetate 98:2) to obtain a reddish-orange solid in 77, 79, 78, 76 and 75% yields, respectively.

Example 8

Preparation of Solutions Using Diazonium Salts and Other Building Blocks for Single Capillary and Flow Parallel Synthesizer Diazonium Solution: A 100 mL and 0.77M solution of each diazonium salt (77 mmol) was prepared using DMSO.

Building Block 1: A 10 mL and 0.77M KI solution (7.7 mmoles) was prepared using DMSO:H$_2$O (9:1).

Building Block 2: A 10 mL and 0.77M CuCl solution (7.7 mmoles) was prepared using DMSO:HCl (3:2).

Building Block 3: A 10 mL and 0.77 M NaN$_3$ solution (7.7 mmoles) was prepared using DMSO:H$_2$O (9:1).

Building Block 4: A 10 mL and 0.77M p-thiocresol and NaOH (7.7 mmol each) solution was prepared using DMSO:H$_2$O (2.5:1).

Building Block 5: 10 mL of a pure furan solution including 4-aminomorpholine (0.385 mmoles, 5 mol %).

Building Block 6: A 10 mL and 7.7M furan (77 mmol) and Eosin Y (0.385 mmol, 5 mol %) solution was prepared using DMSO.

Building Block 7: 10 mL β-naphthol and NaOH solutions at 0.6375, 0.51, 0.3825, 0.31875 and 0.255 M (6.375, 5.1, 3.825, 3.1875 and 2.55 mmoles, respectively) were prepared using DMSO:H$_2$O (9:1), respectively.

Building Blocks 8 to 12: A 5 mL and 0.51M imidazopyridine/imidazothiazole (2.55 mmol) solution was prepared using DMSO.

Example 9

Concurrent Optimization of Complex Libraries

Diazonium (0.77M) solutions and other building blocks were prepared according to Example 7. Stock solutions of diazonium and the building blocks were each transferred to two 10 mL NORM-JECT plastic syringes and introduced into PTFE reactors using two syringe pumps. The stock solutions of diazonium and the building blocks were pumped at specific flow velocities using two syringe pumps in order to meet the required residence times shown in Table N below (Building Block 1: 0.033 mL/min, Building Block 2: 0.16 mL/min, Building Block 3:0.66 m/min and all other Building Blocks (4 to 12): 0.33 m/min, and the flow velocity ratio of diazonium to the Building Block solution=1:1). The two solutions were met in a T-mixer and injected into a PTFE reactor (L=1,500 mm, 1/16' O.D., 0.75 mm I.D.) which was set to room temperature. After maintaining steady state, samples were collected for each individual reaction. After work up using water, it was purified, and the purification procedure was similar to the described procedure (refer to Example 6).

Figure 11:
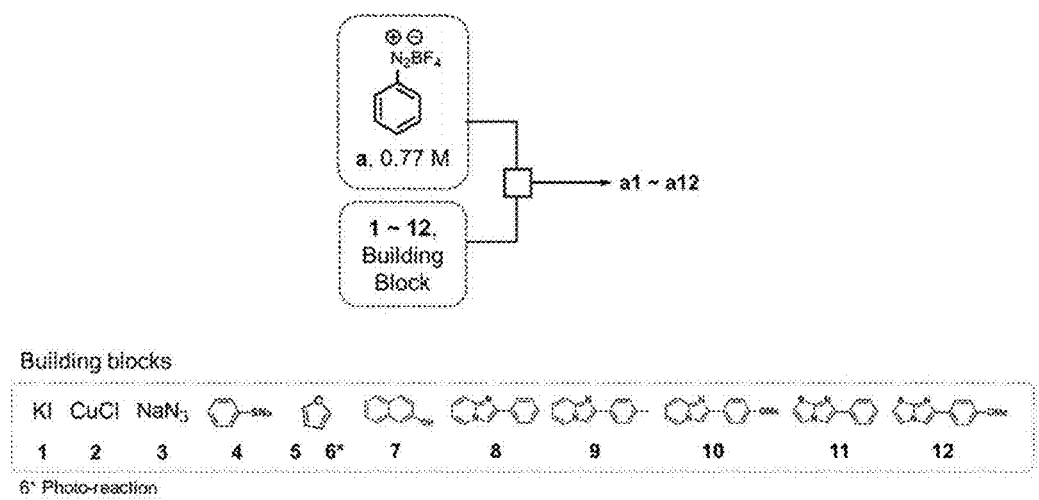
FIGS. 11 and 12 are reaction mimetic diagrams of aryl diazonium salts.
Figure 12:
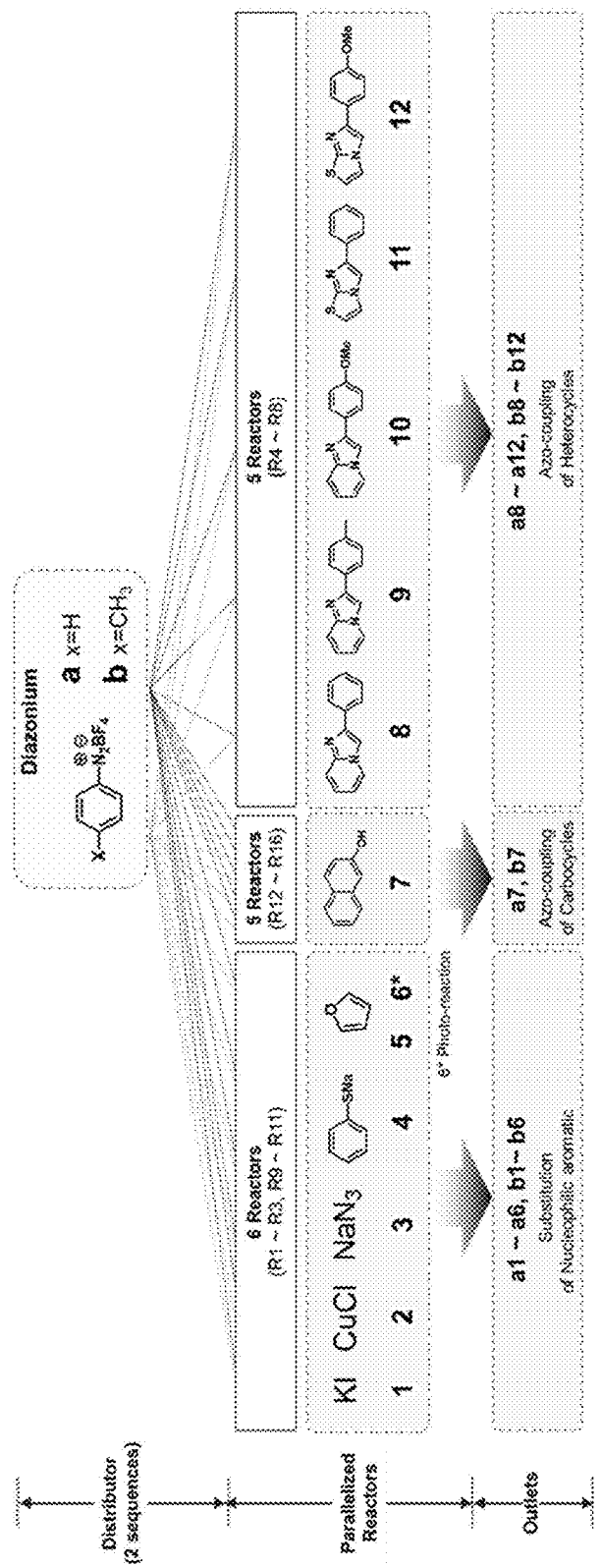

FIGS. 11 and 12 show the parallel synthesis method of diazonium according to an exemplary embodiment of the present invention. Various reactions may be simultaneously performed using a diazonium salt as the first reactant. In particular, FIG. 12 is a schematic diagram of aryl diazonium chemistry enabled by multiplex reactions in the flow parallel synthesizer through two series of experiments. Referring to FIG. 12, it can be seen that a list of 12 building blocks may react with two types of diazonium salts to form 6 types of chemical bonds (C—Halogen, C—N, C—S, C—C, —N=N—) in a library of 24 compounds.

Figure 13:
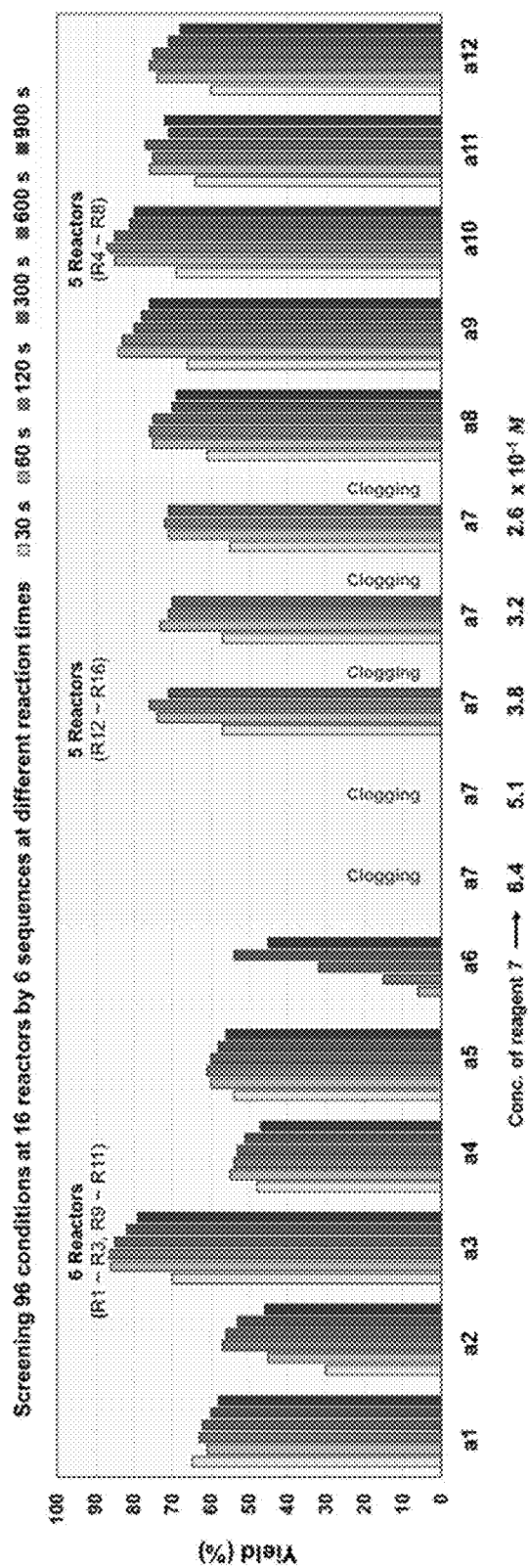
FIG. 13 is a graph showing the synthesis yields of products according to reaction conditions when the parallel synthesizer is used according to an exemplary embodiment of the present invention.
Figure 15:
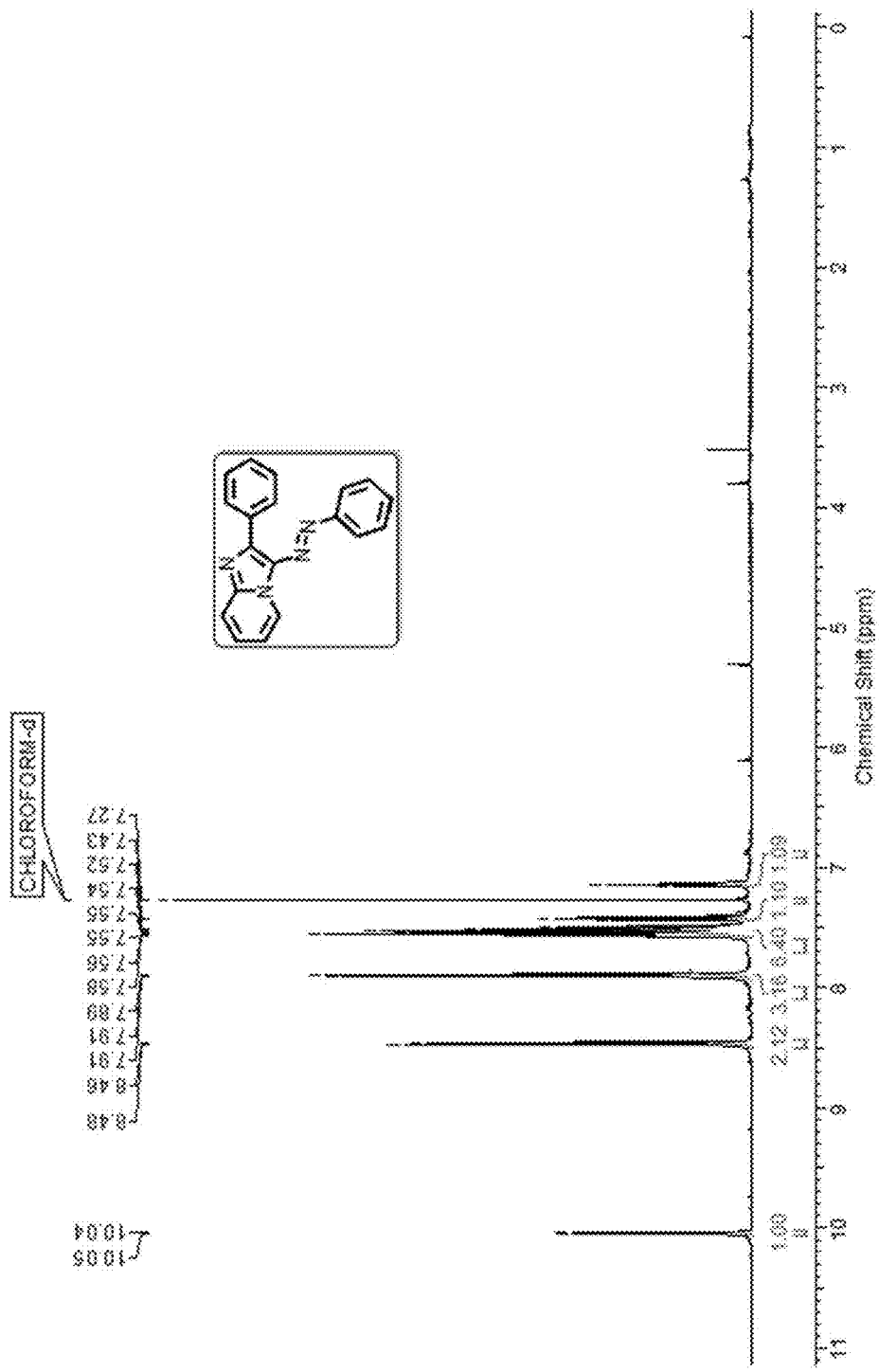
FIGS. 15 to 58 show NMR results of each compound synthesized according to an exemplary embodiment of the present invention.
Figure 16:
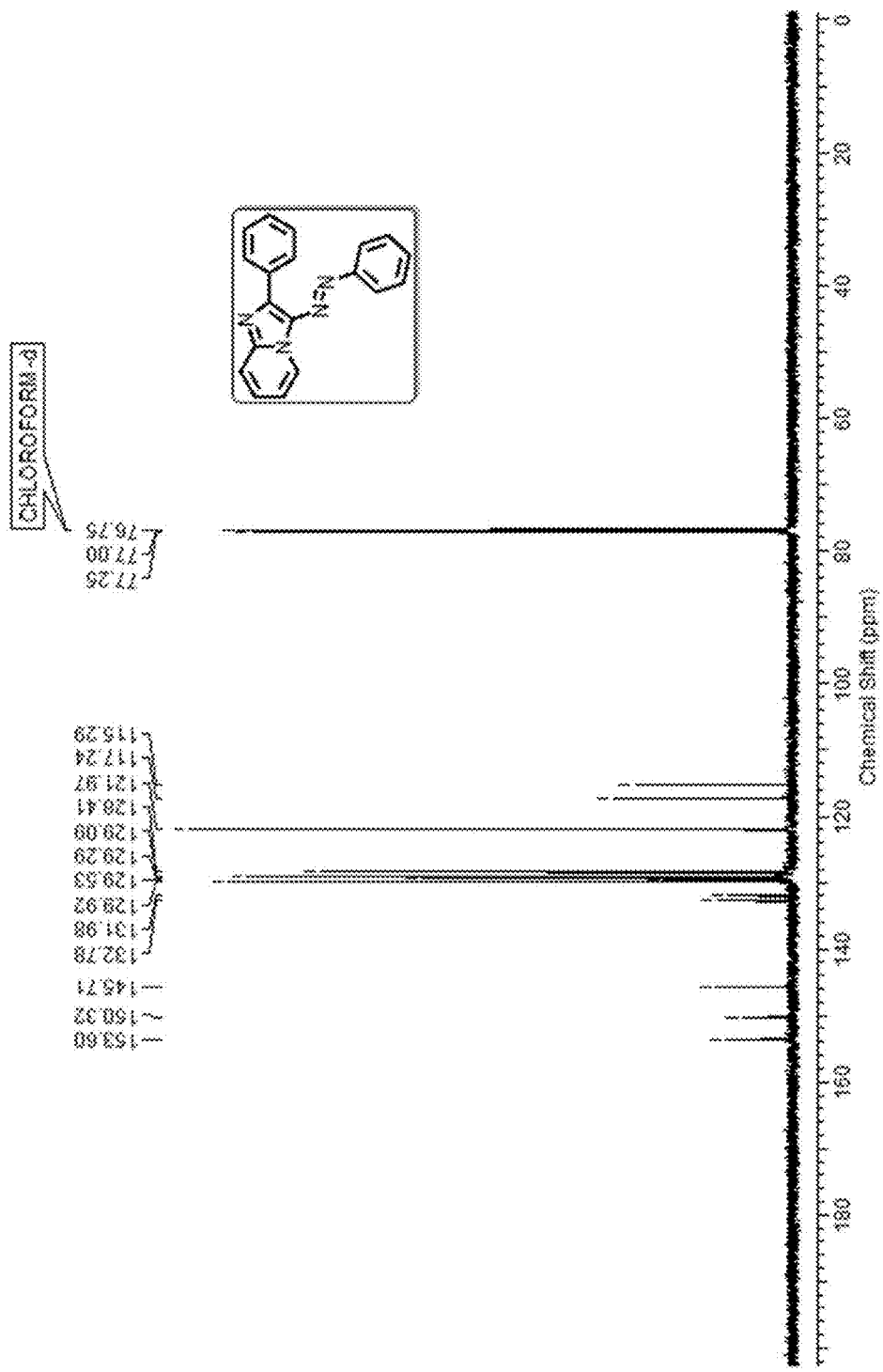
Figure 17:
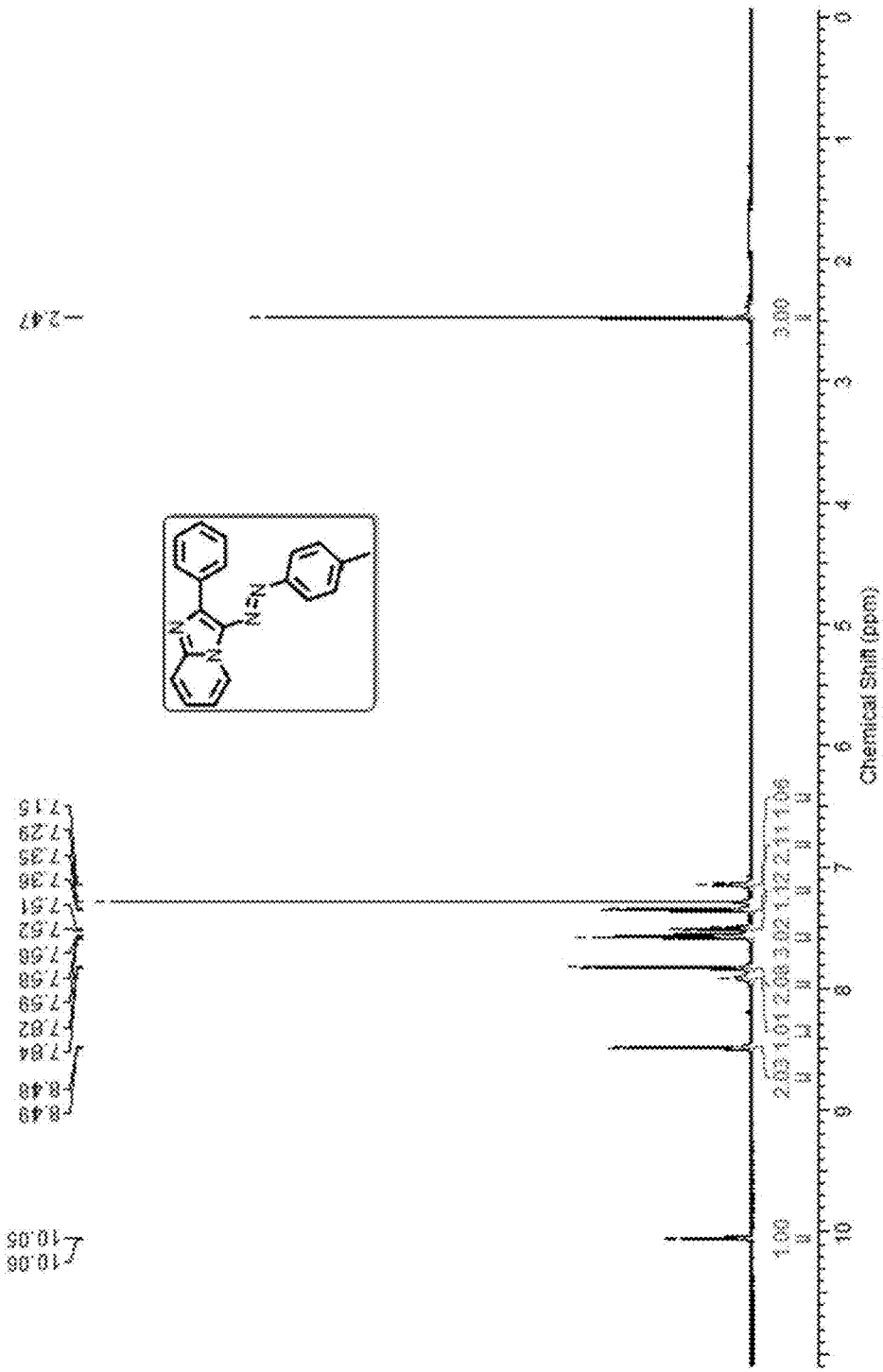
Figure 18:
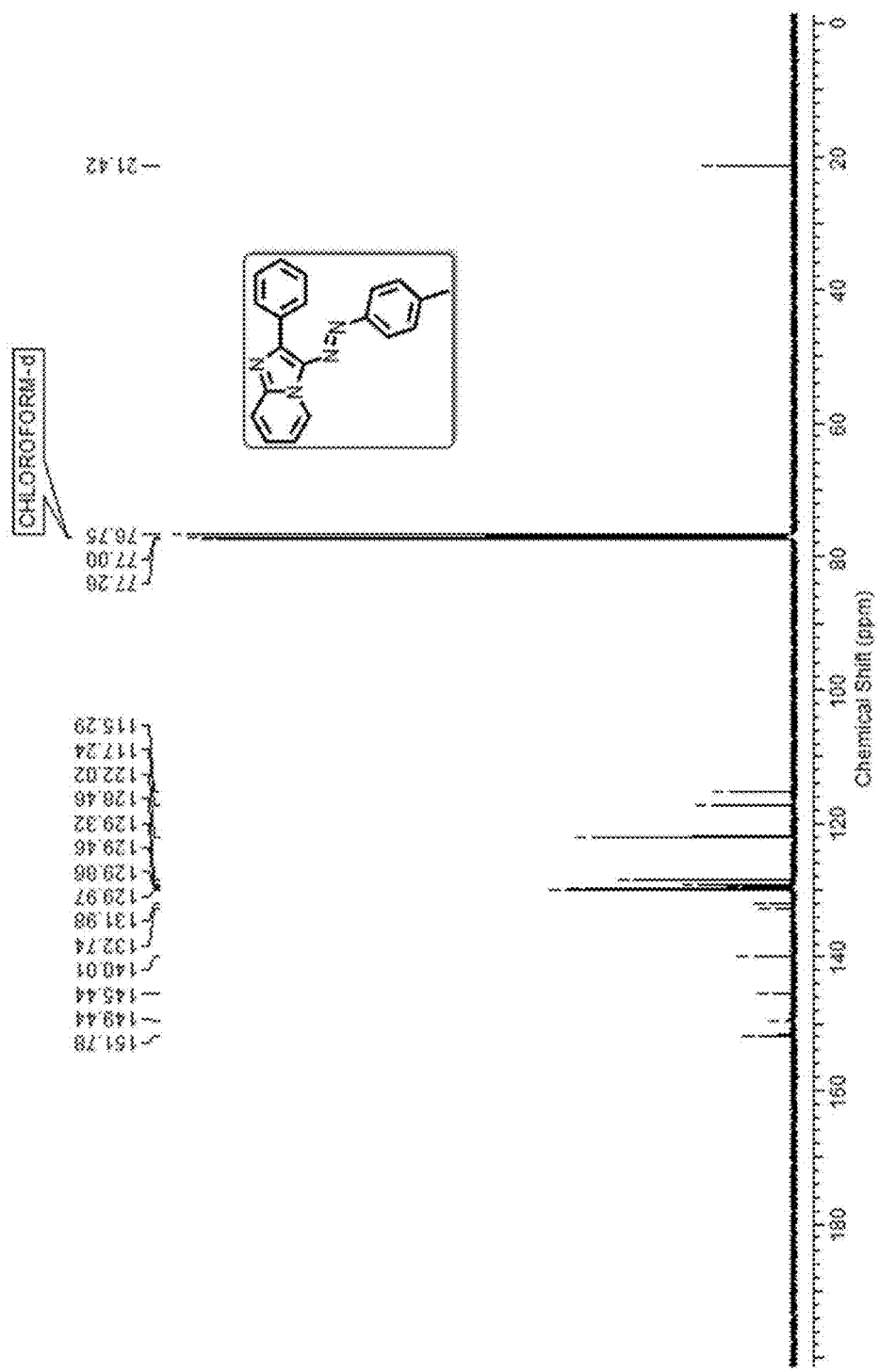
Figure 19:
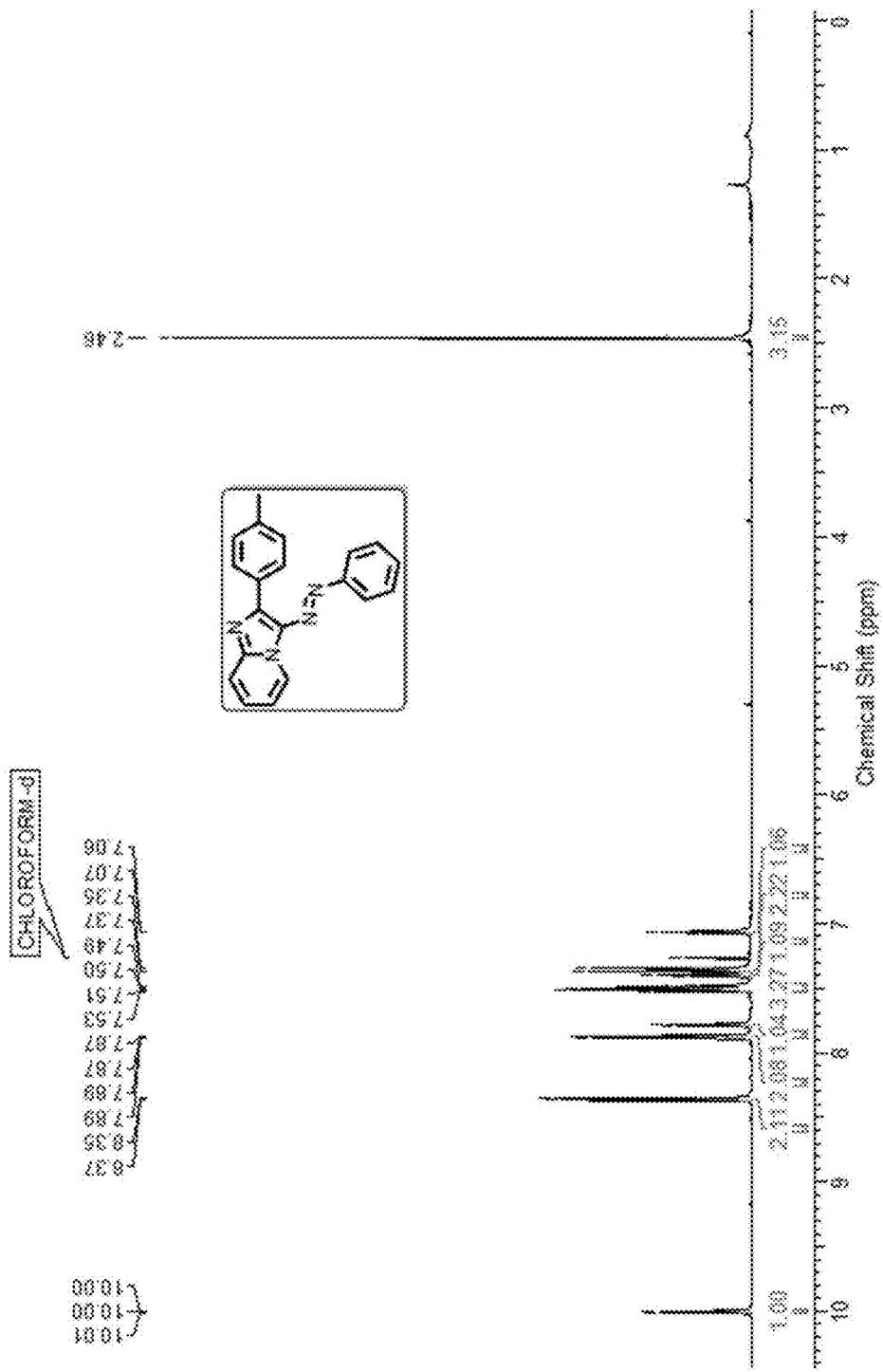
Figure 20:
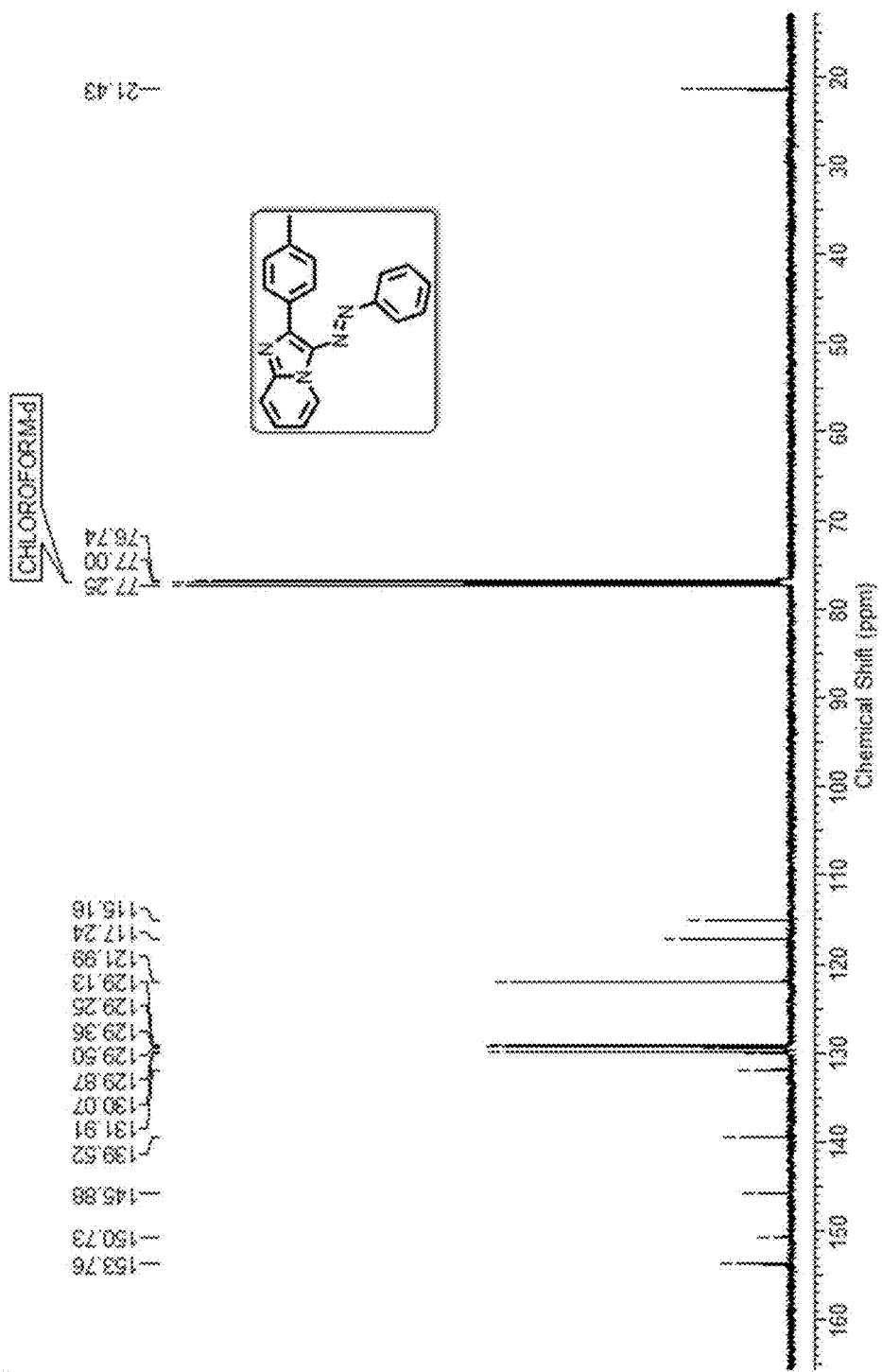
Figure 21:
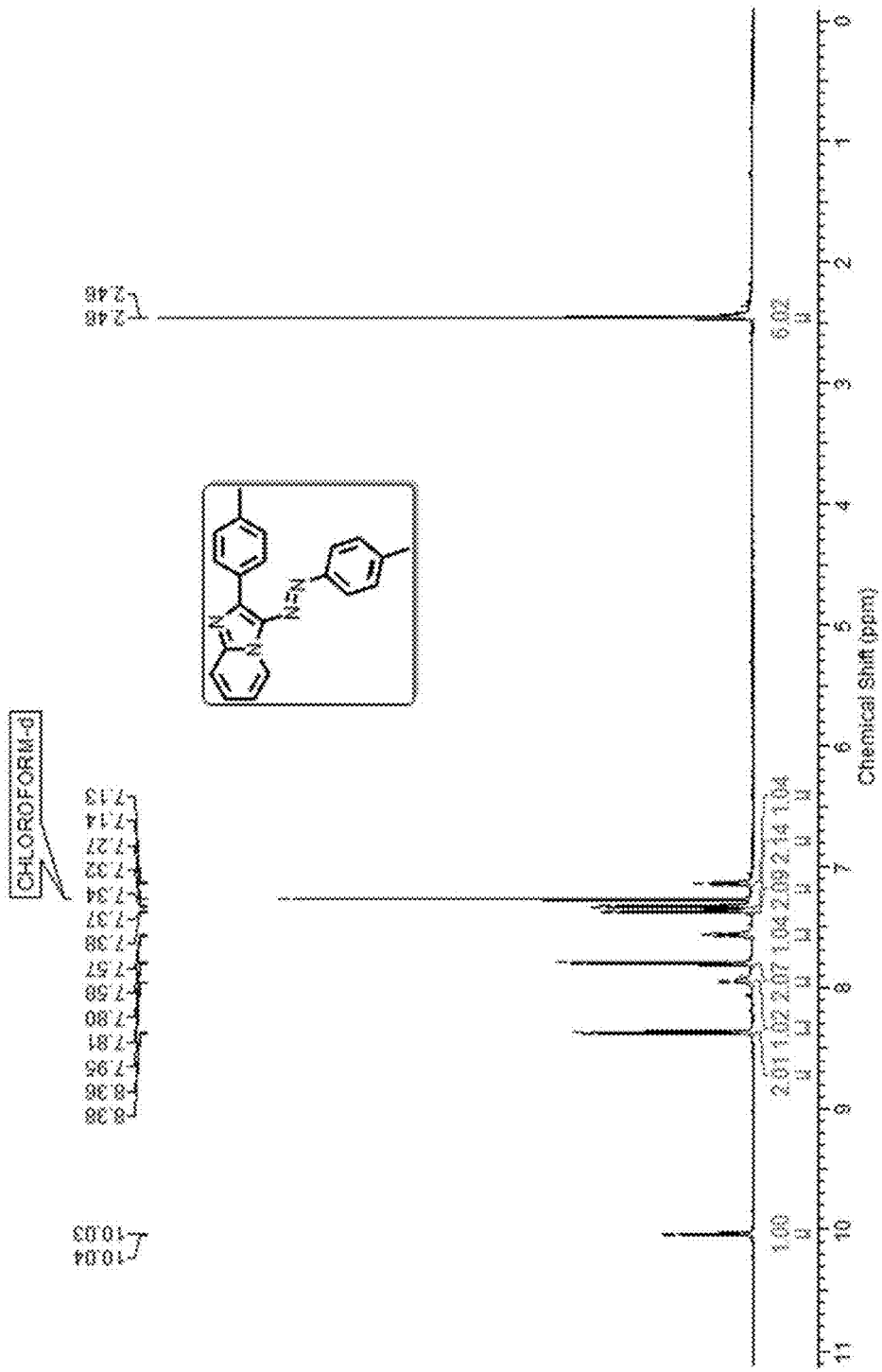
Figure 22:
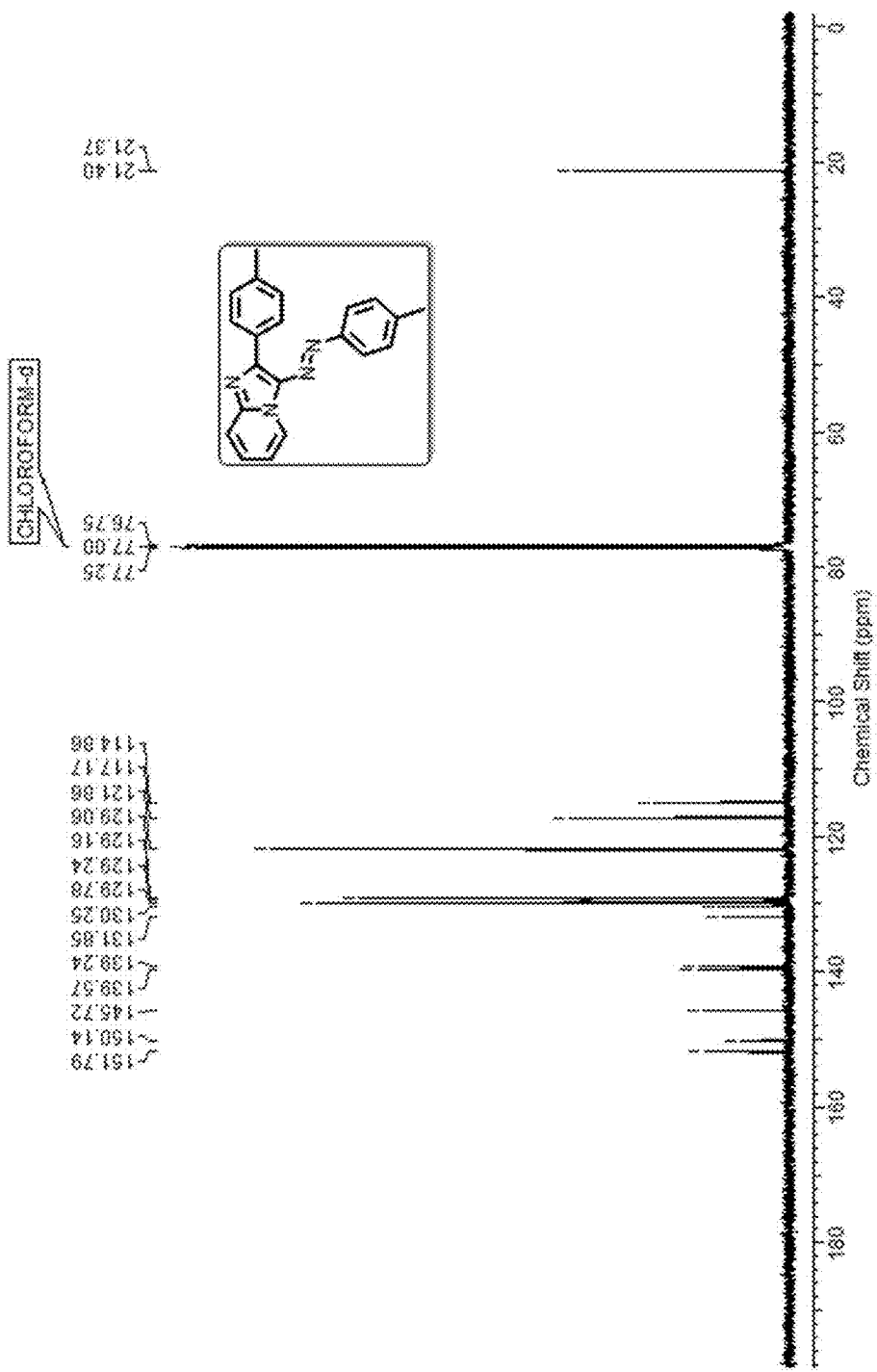
Figure 23:
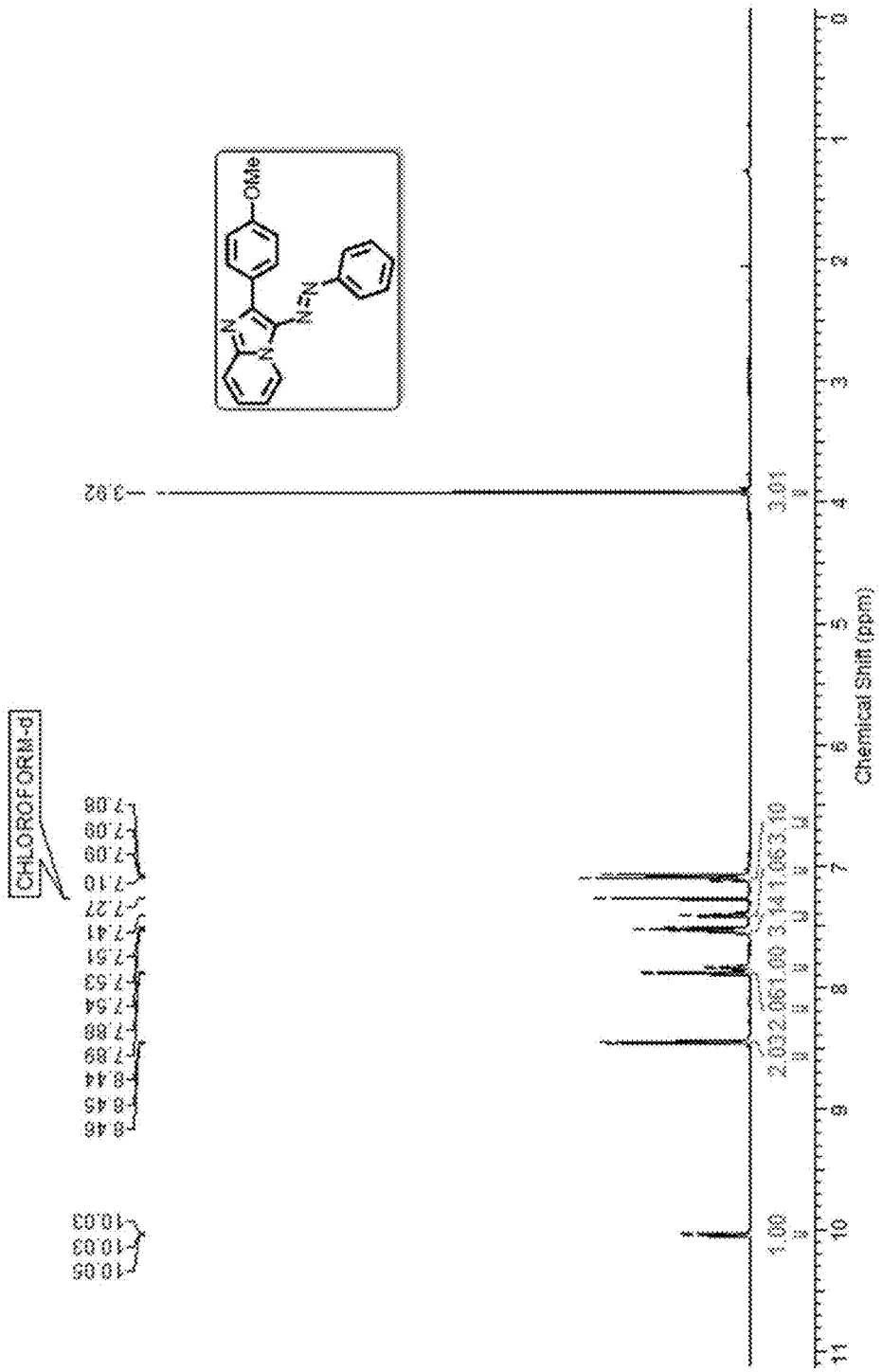
Figure 24:
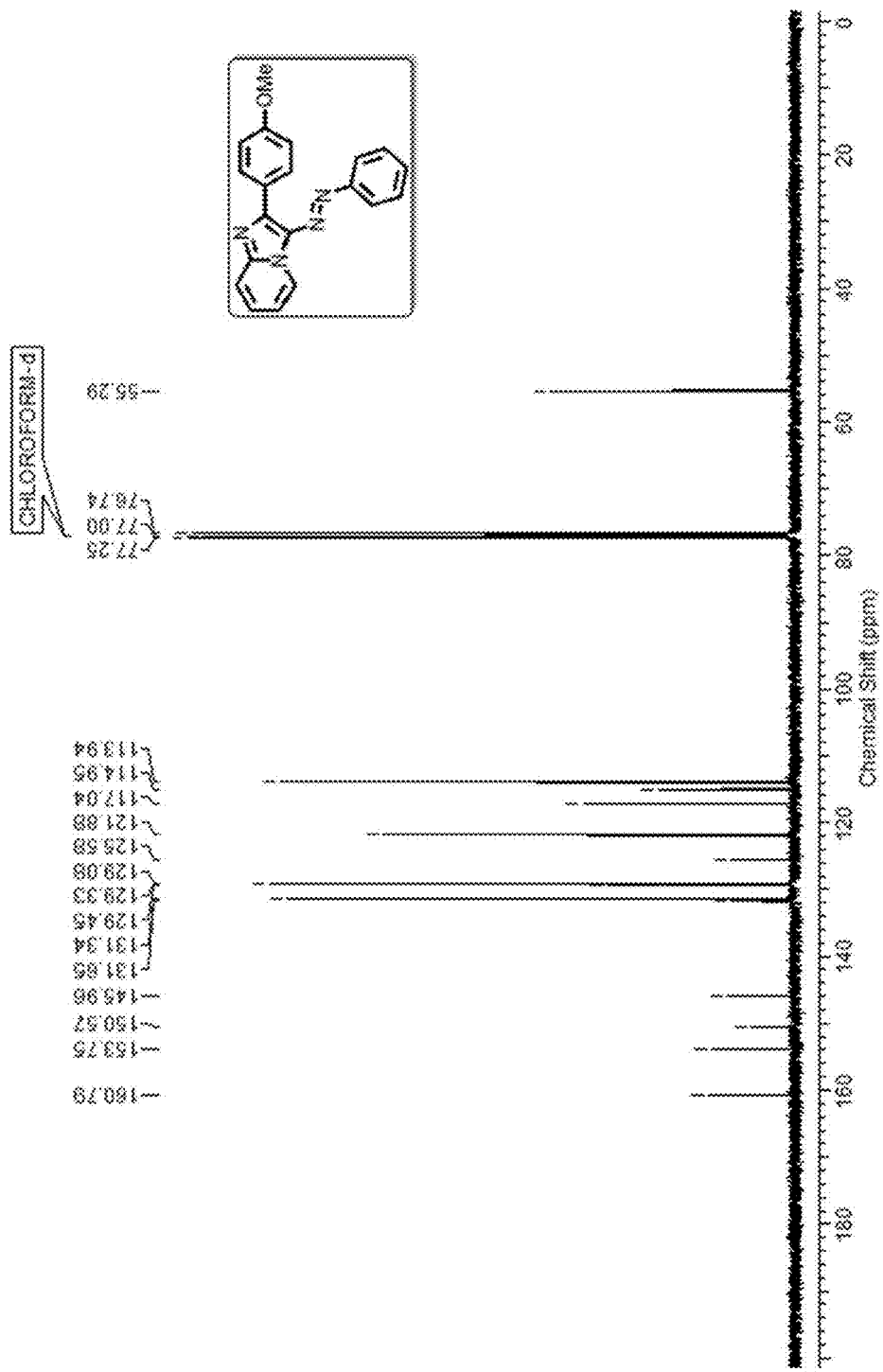
Figure 25:
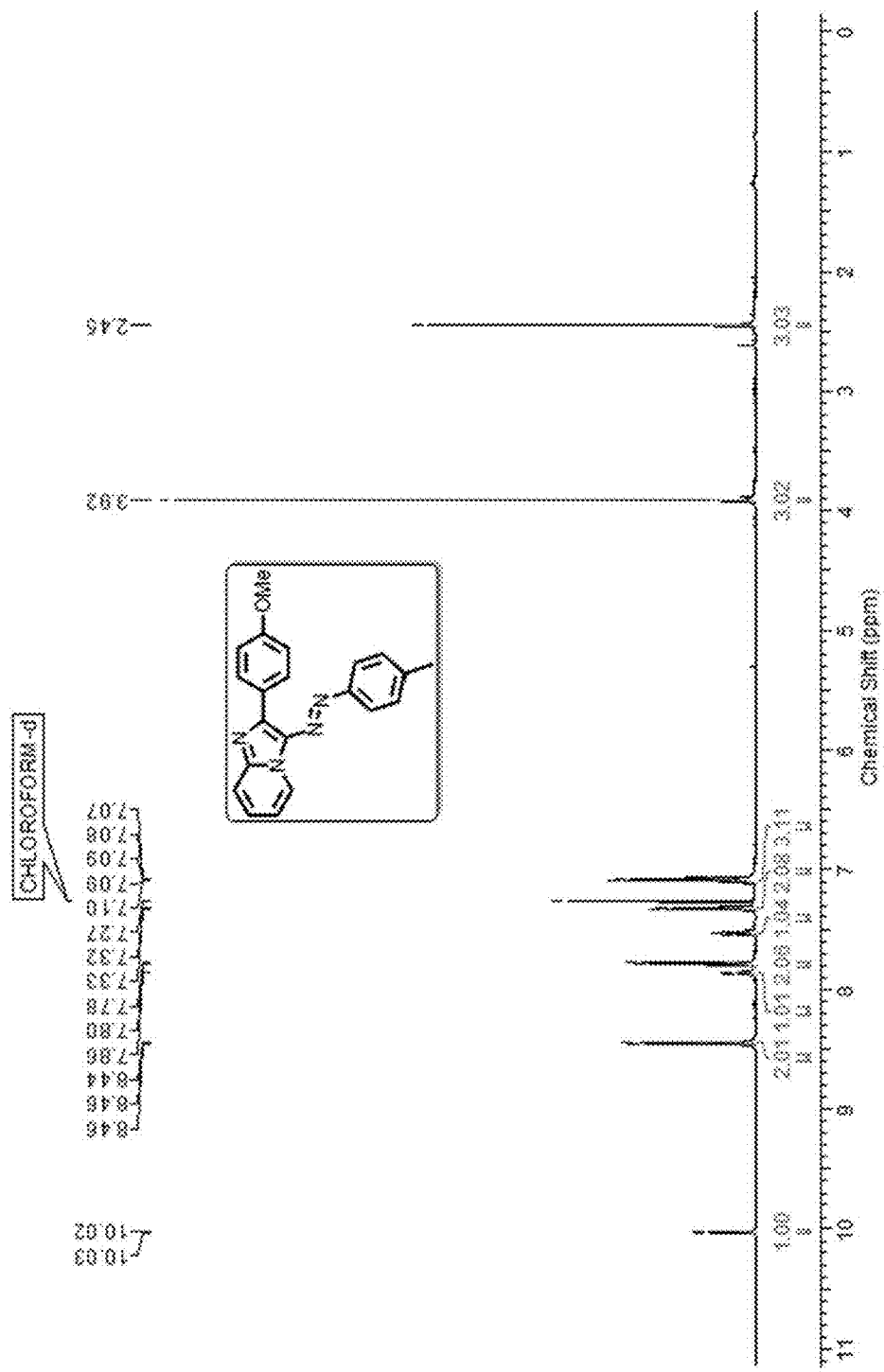
Figure 26:
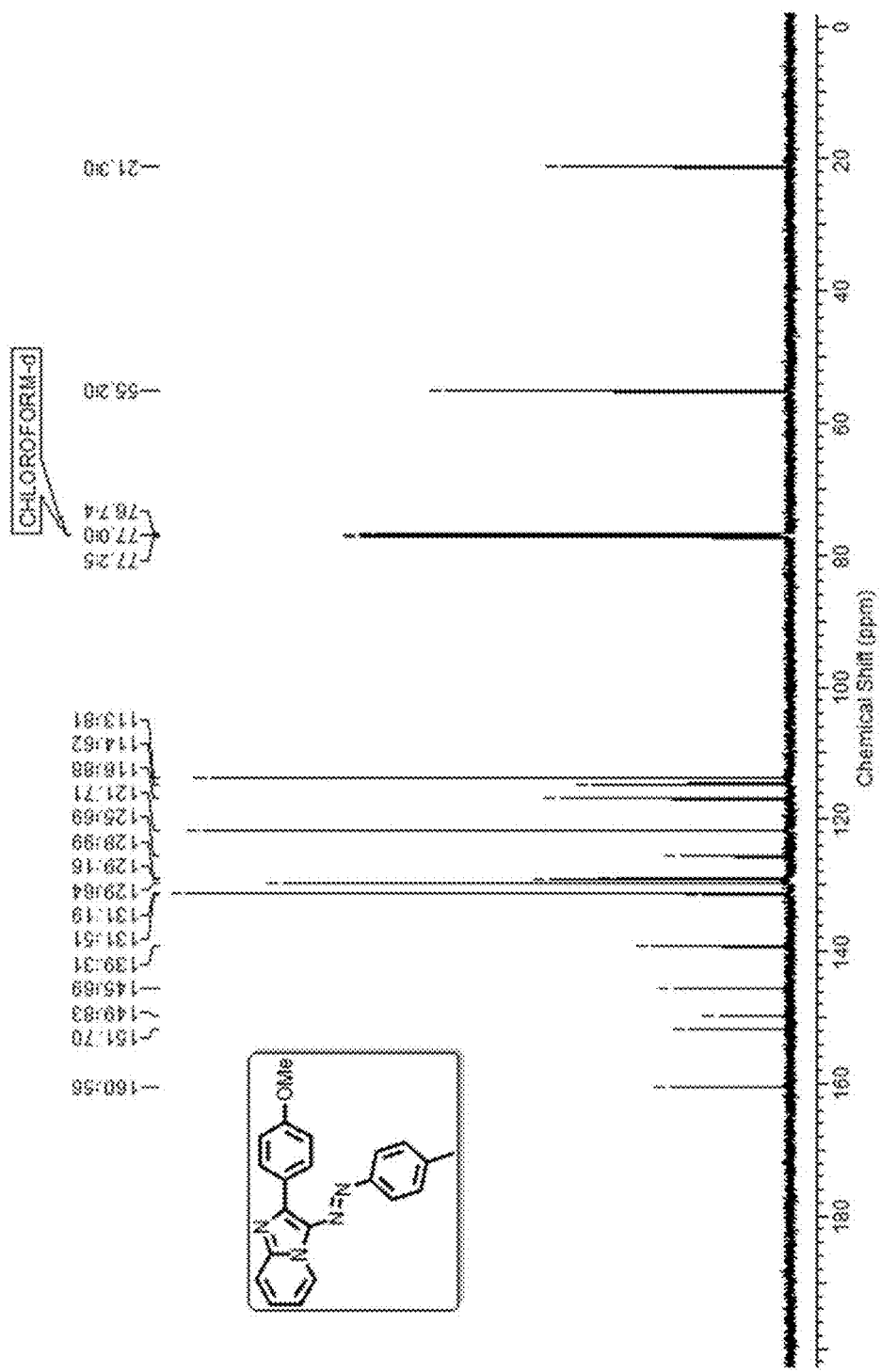
Figure 27:
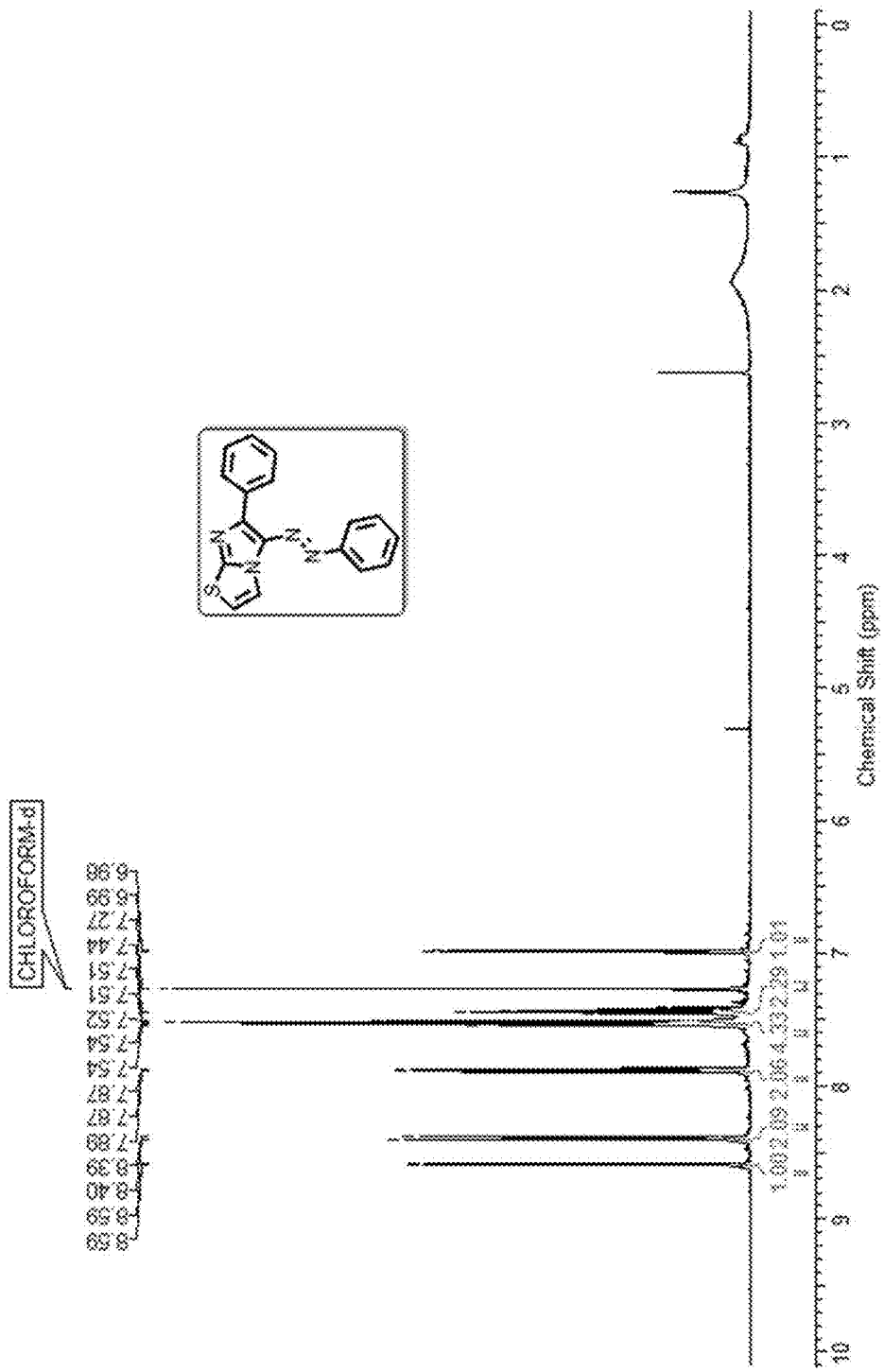
Figure 28:
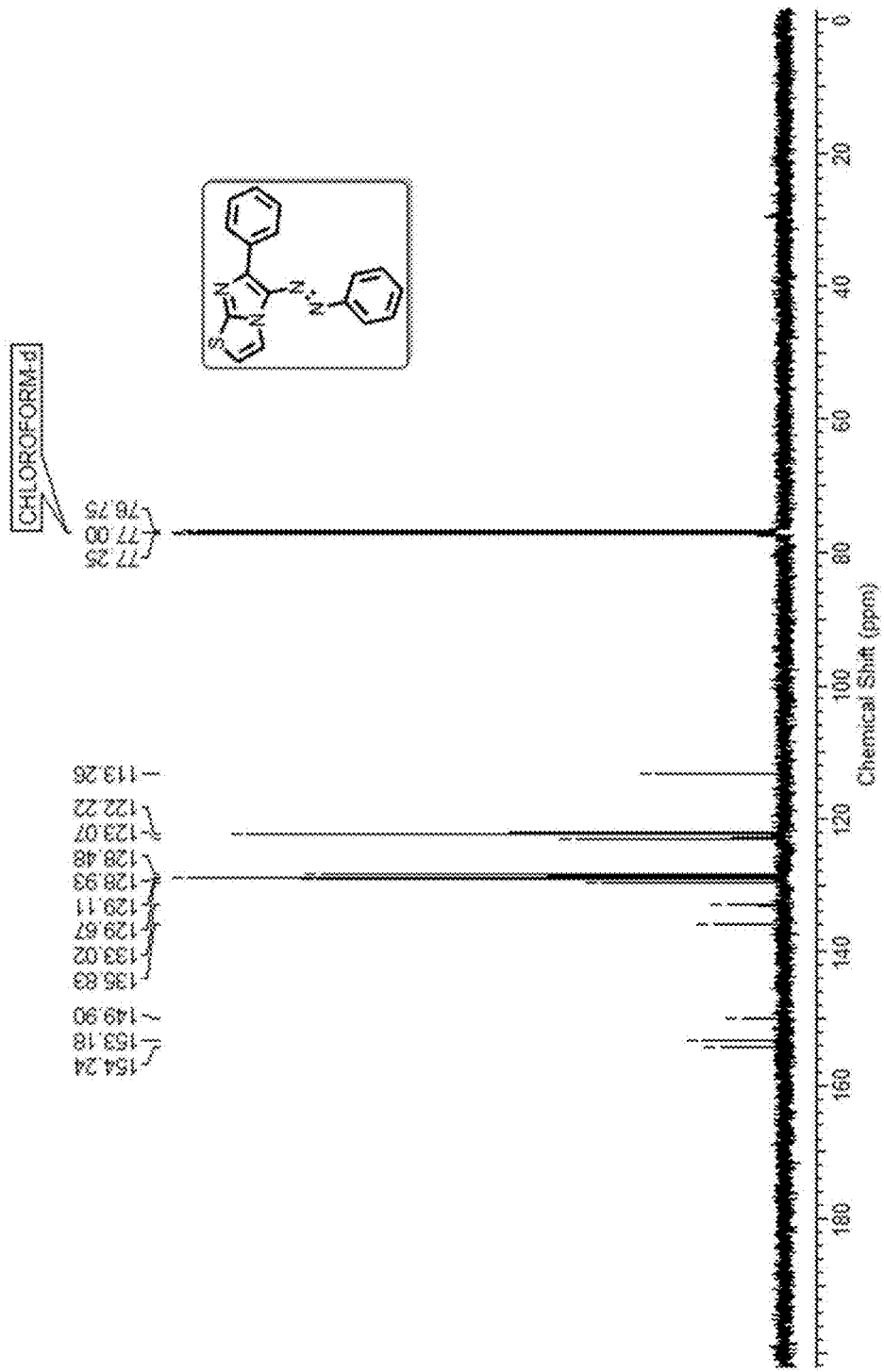
Figure 29:
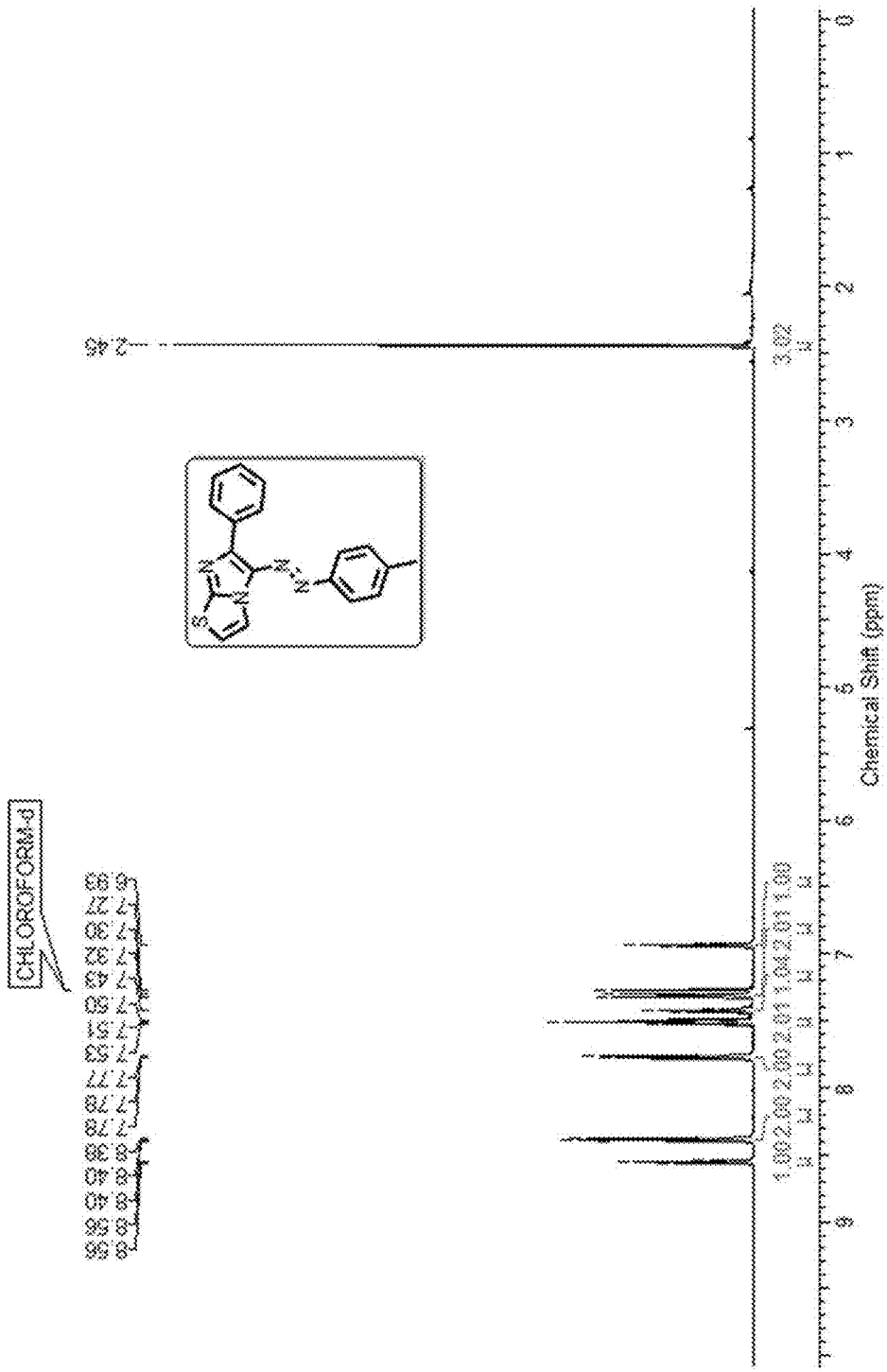
Figure 30:
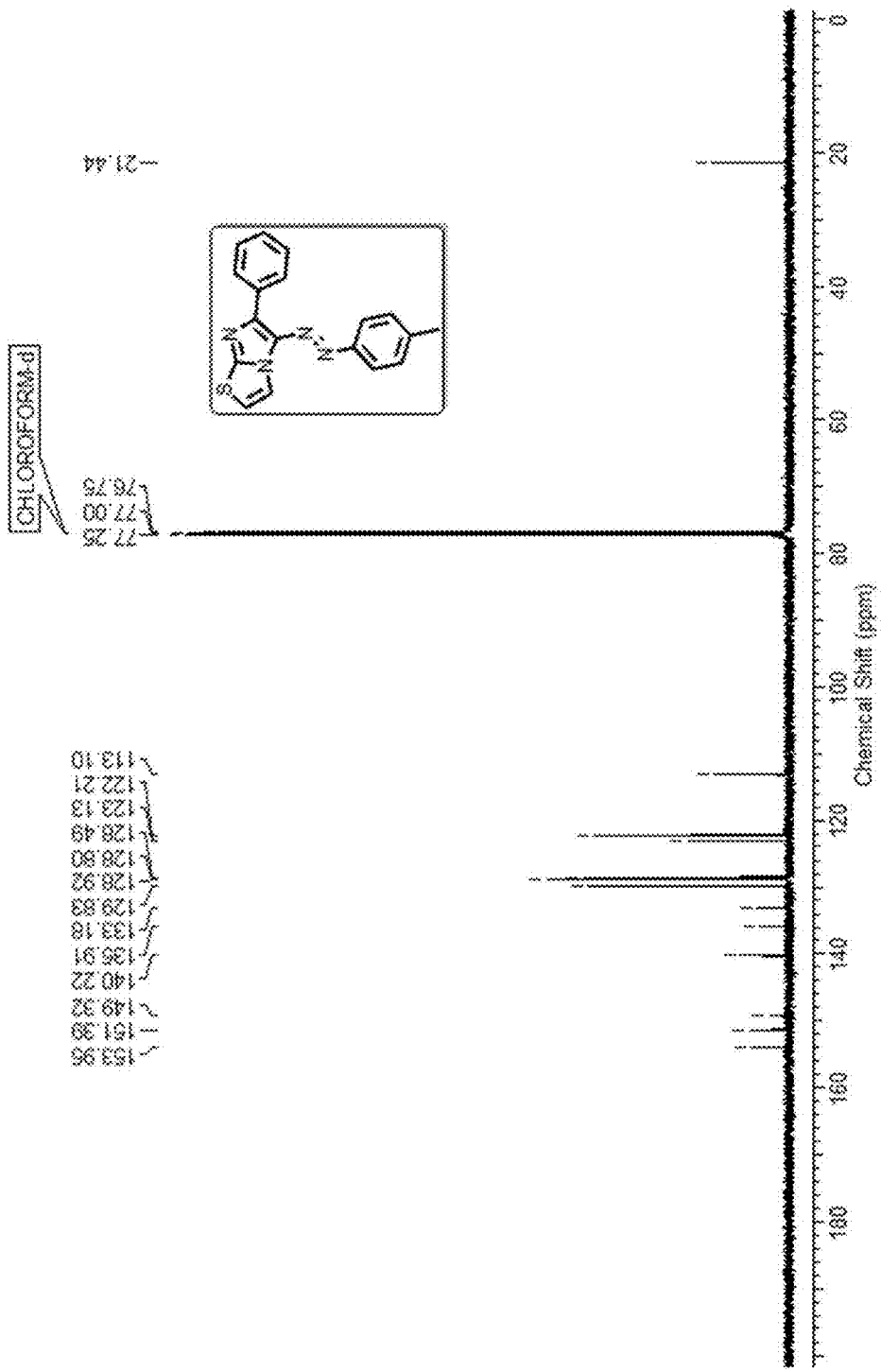
Figure 31:
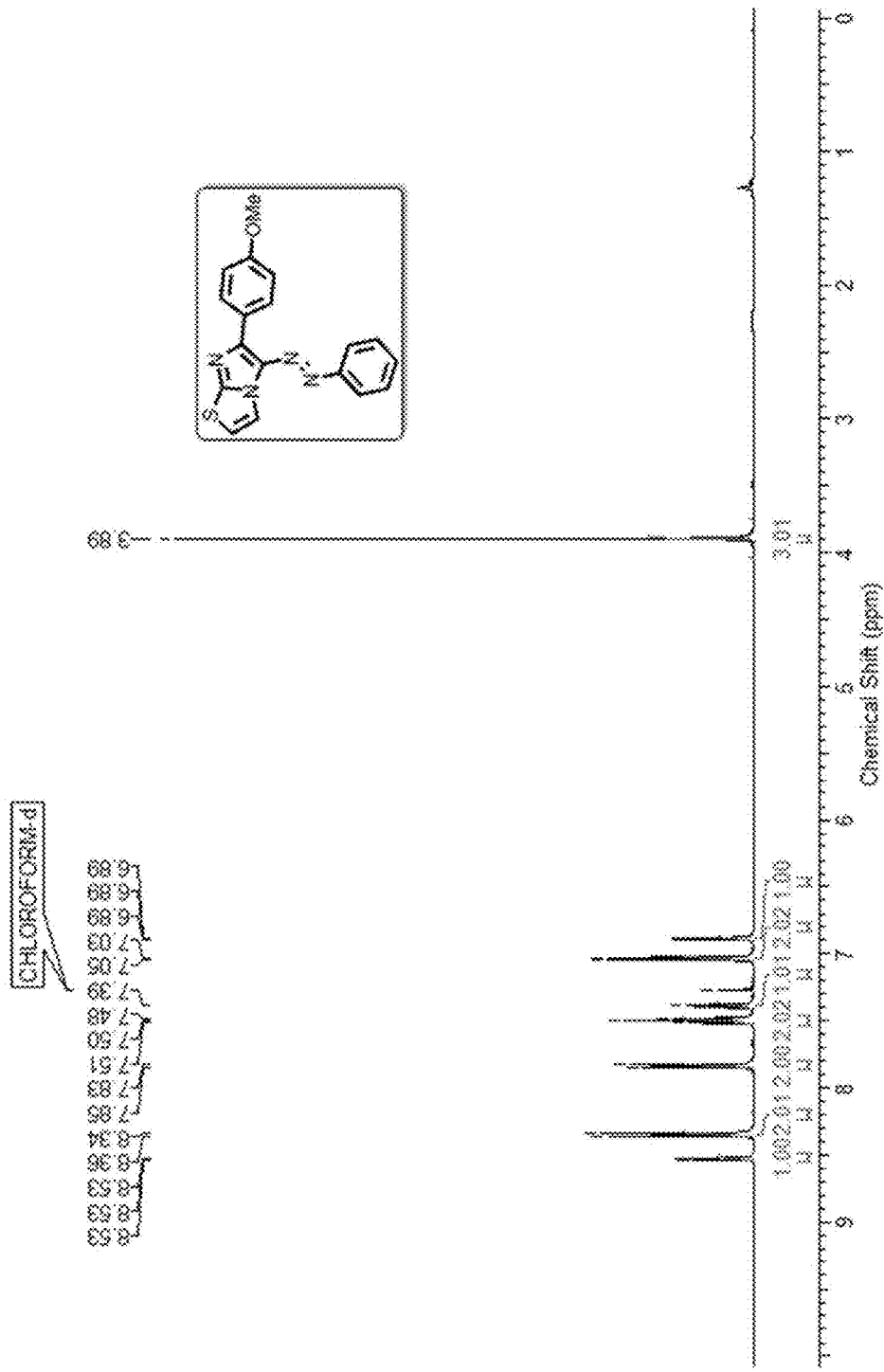
Figure 32:
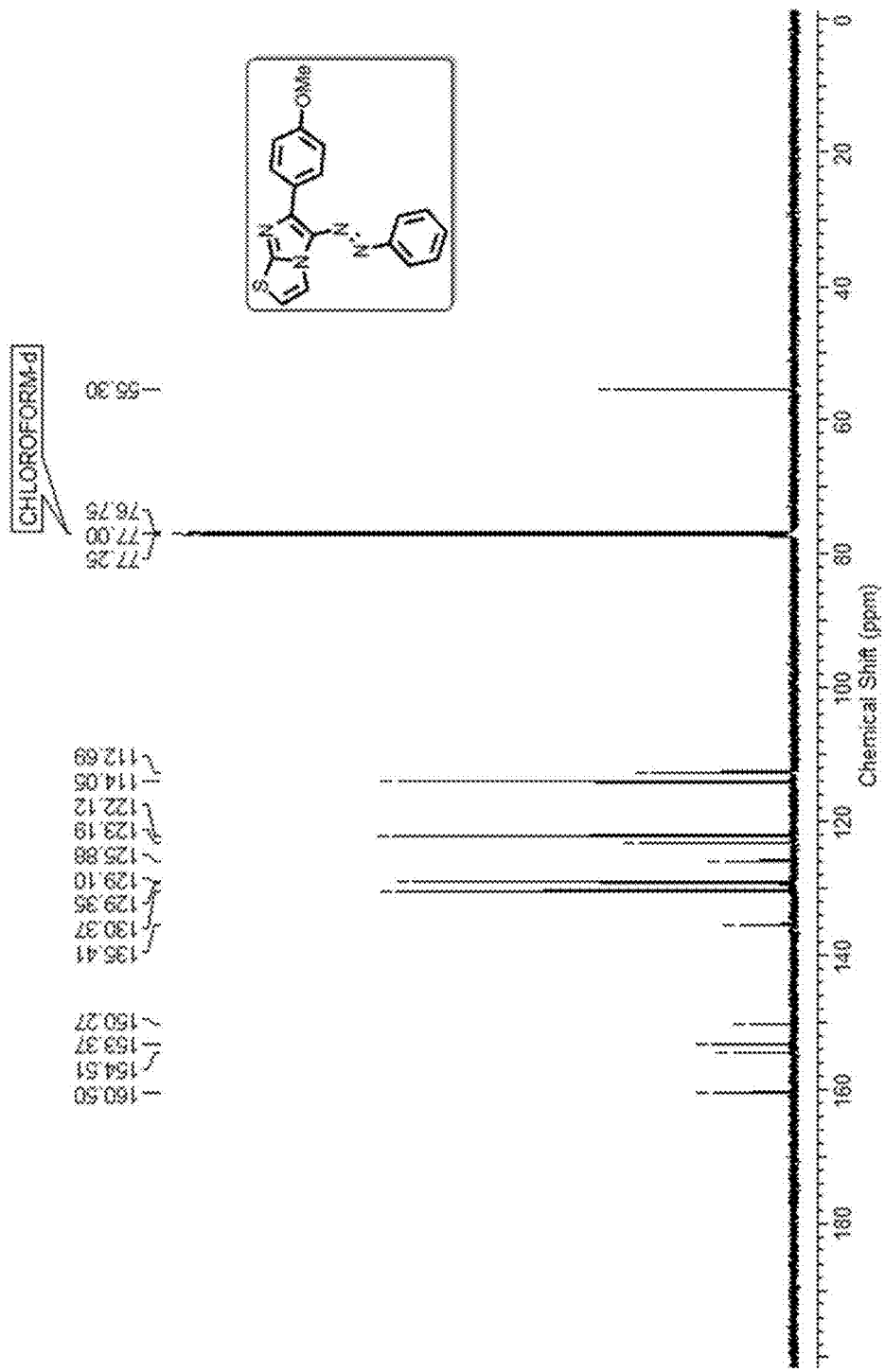
Figure 33:
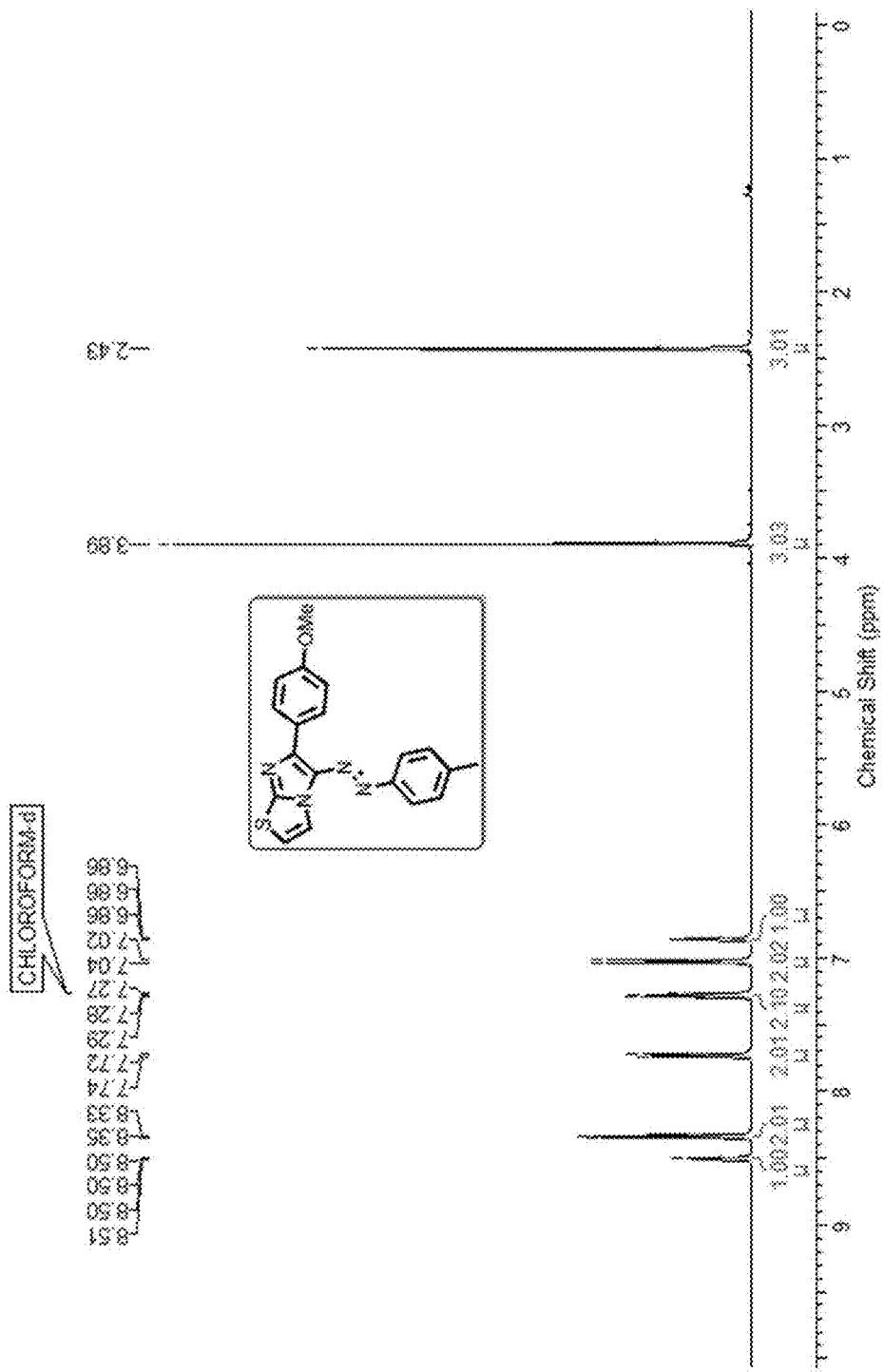
Figure 34:
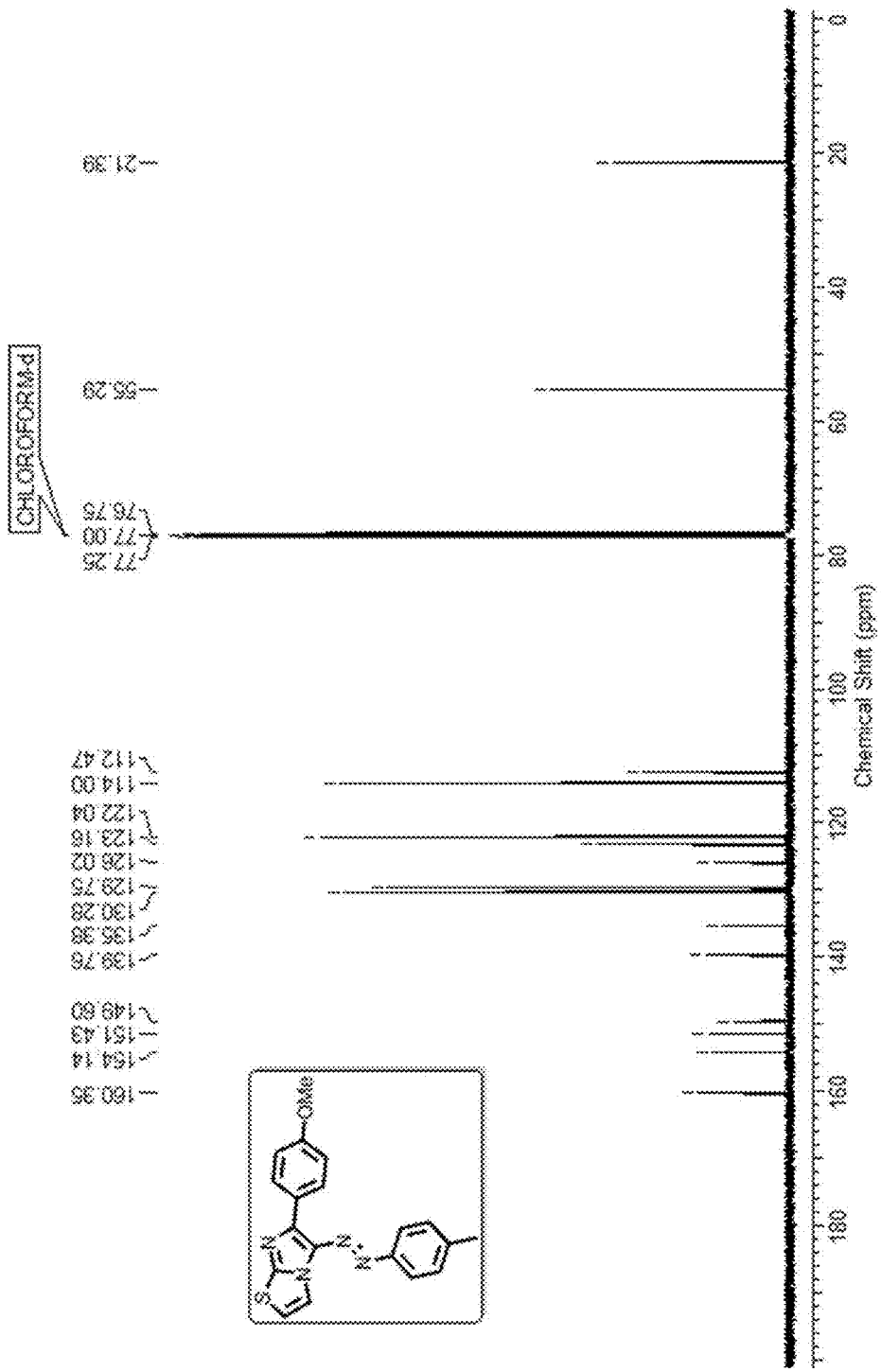
Figure 35:
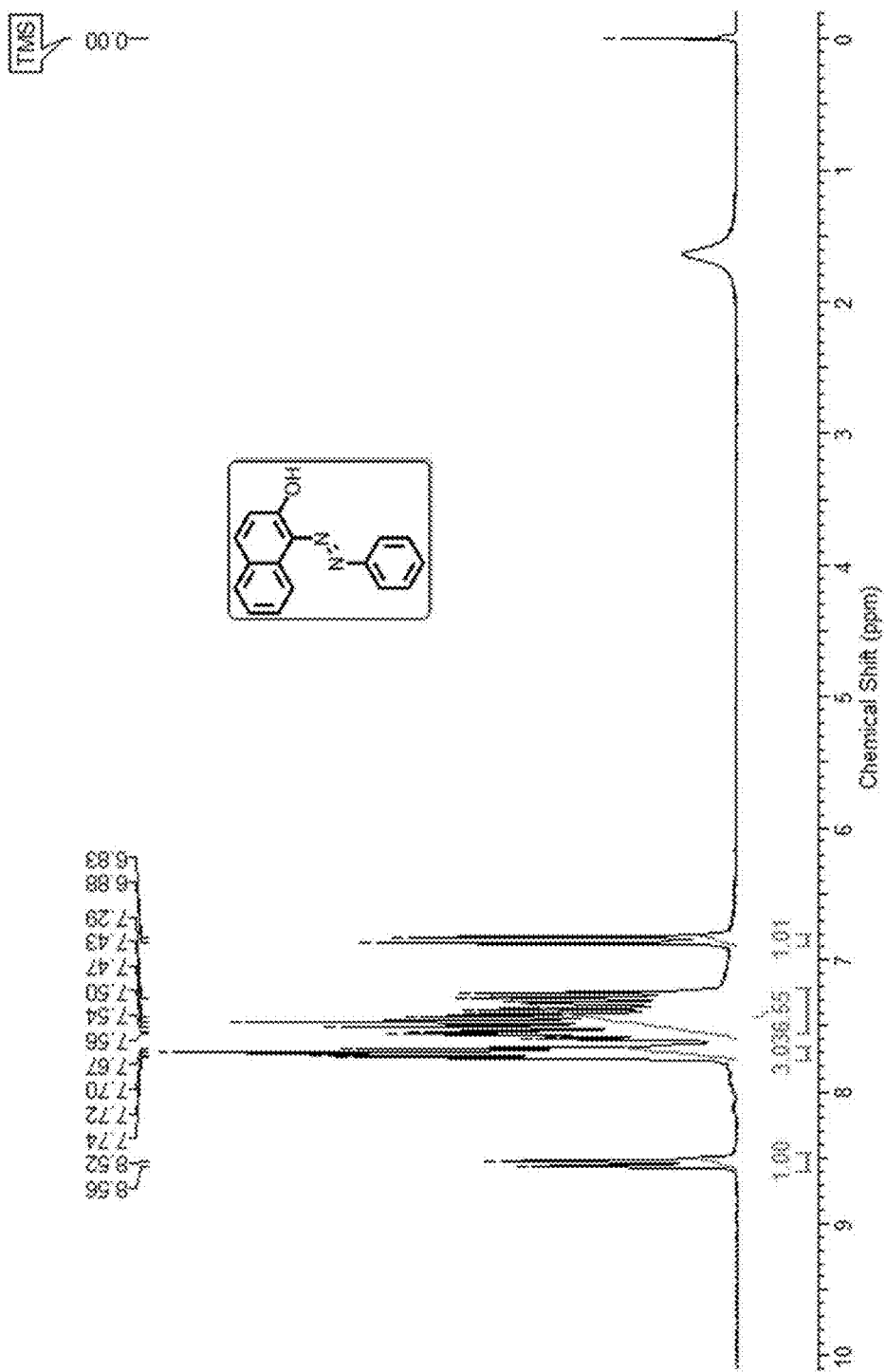
Figure 36:
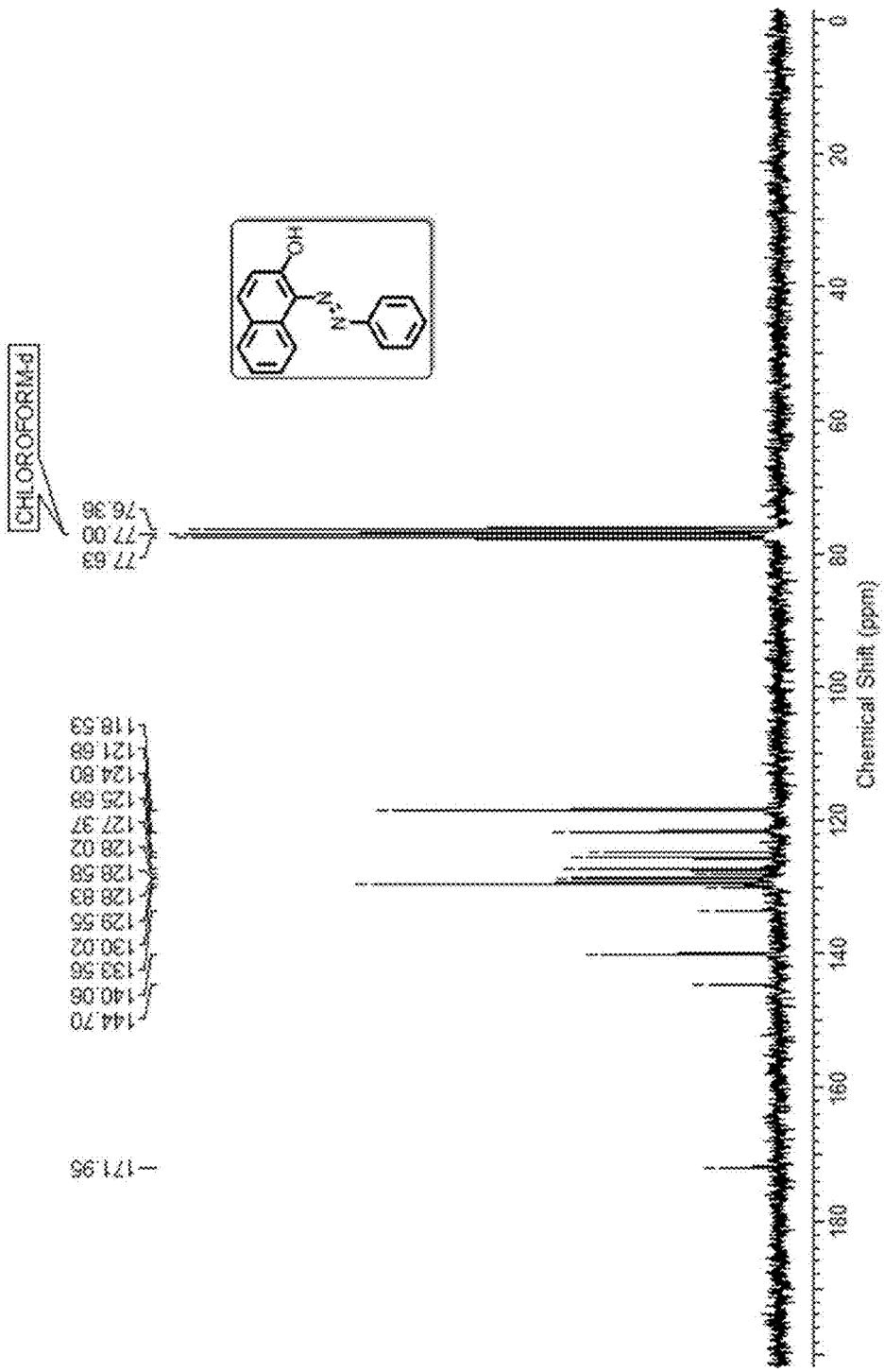
Figure 37:
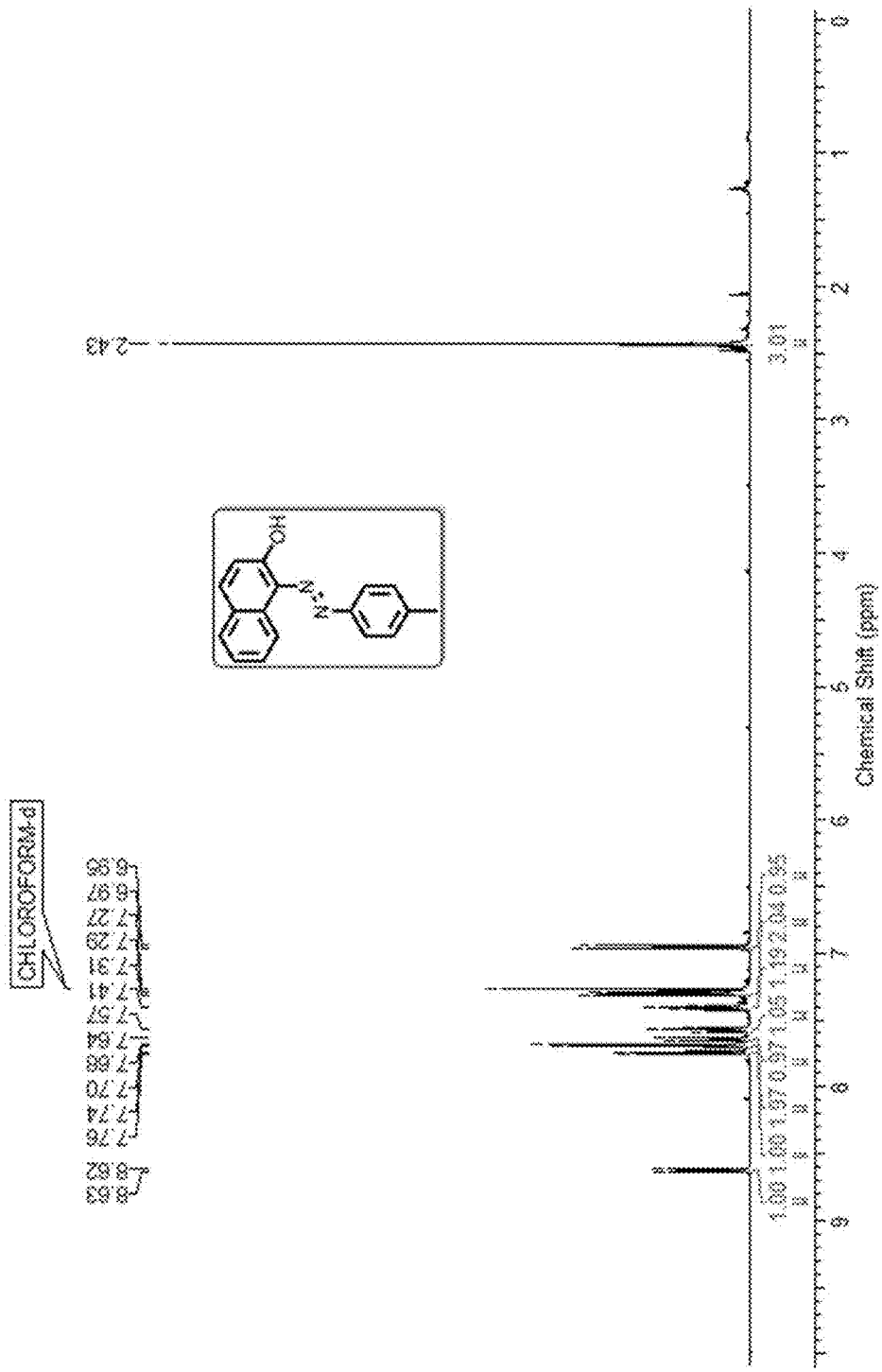
Figure 38:
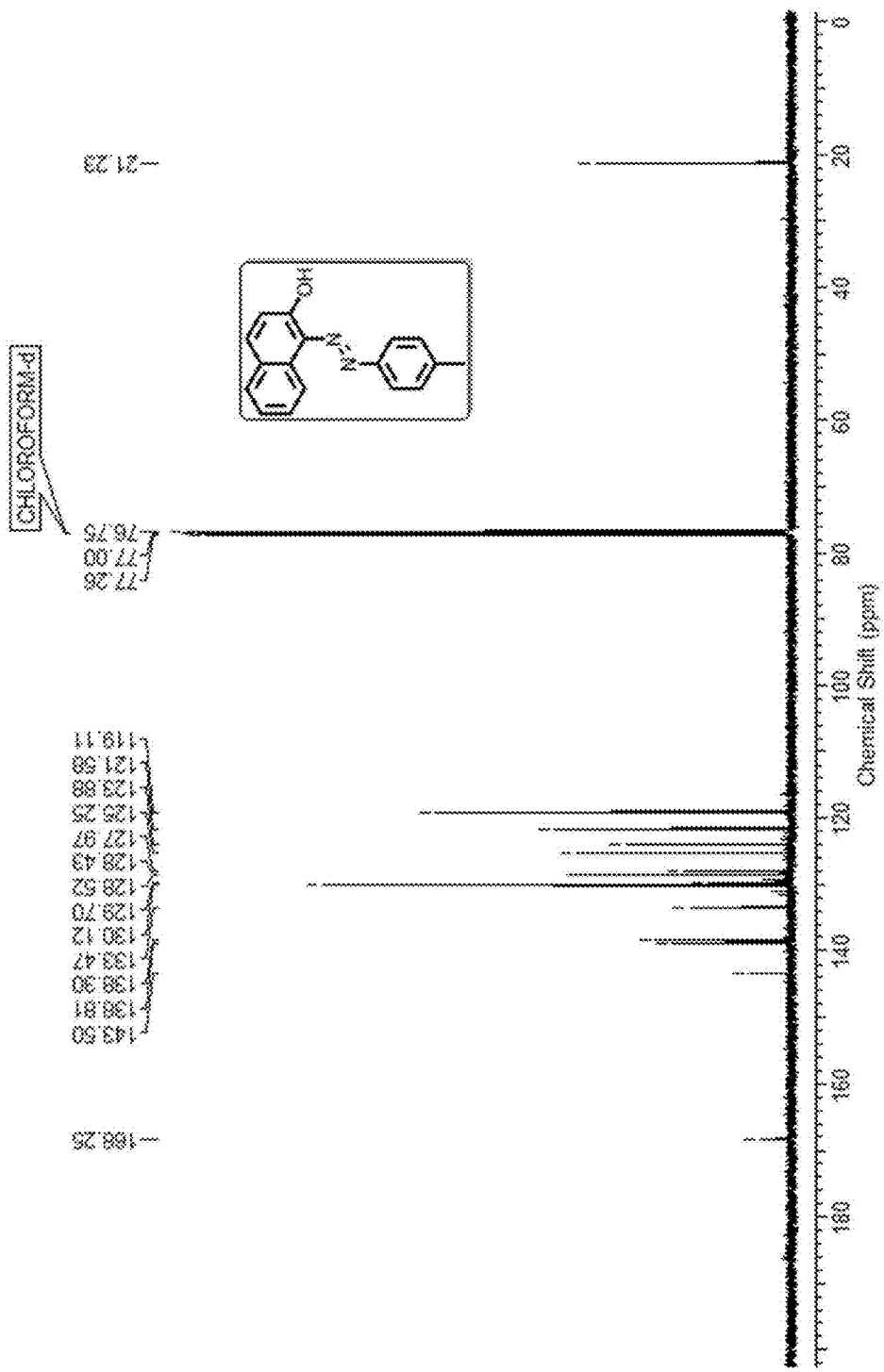
Figure 39:
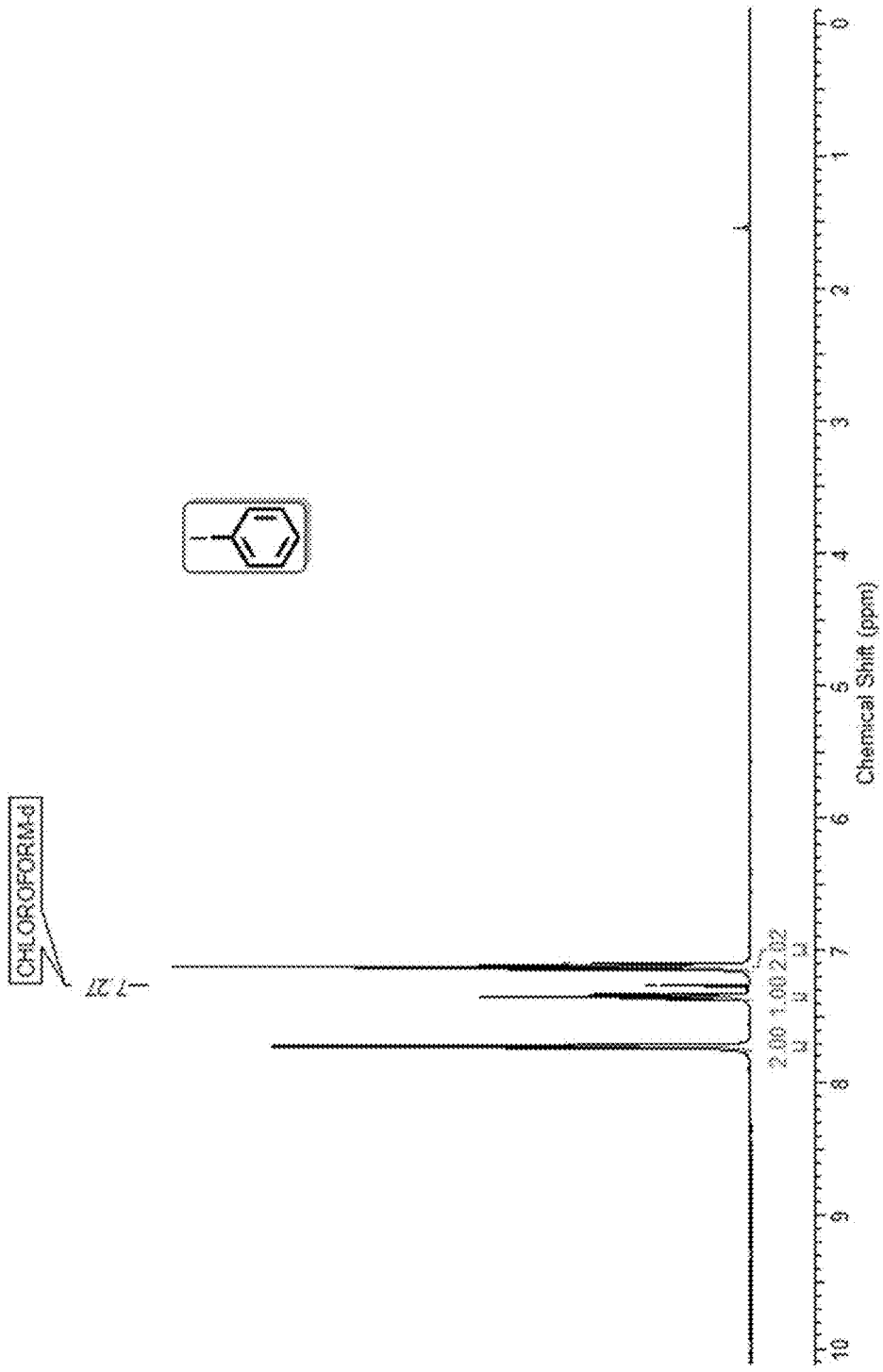
Figure 40:
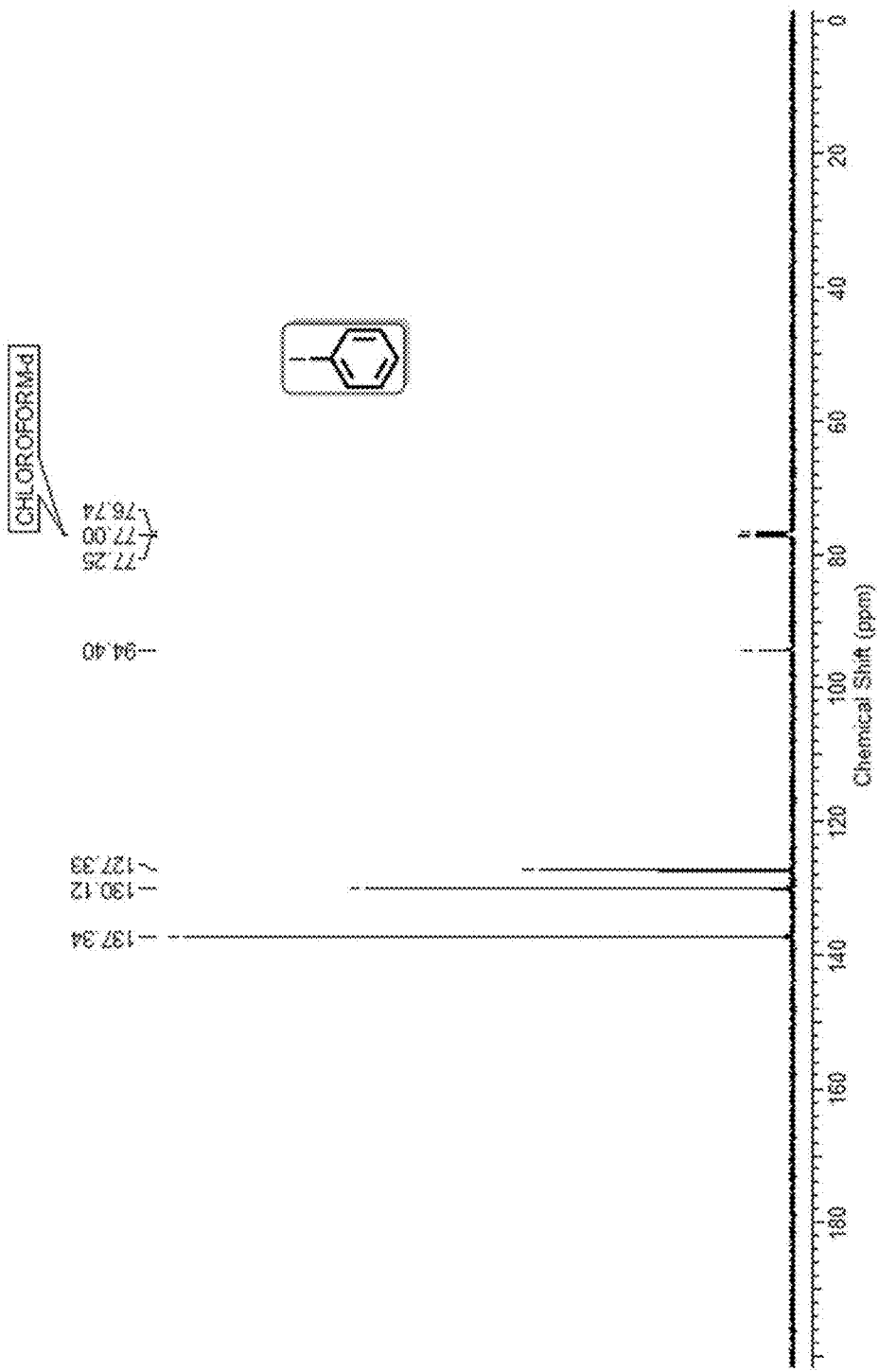
Figure 41:
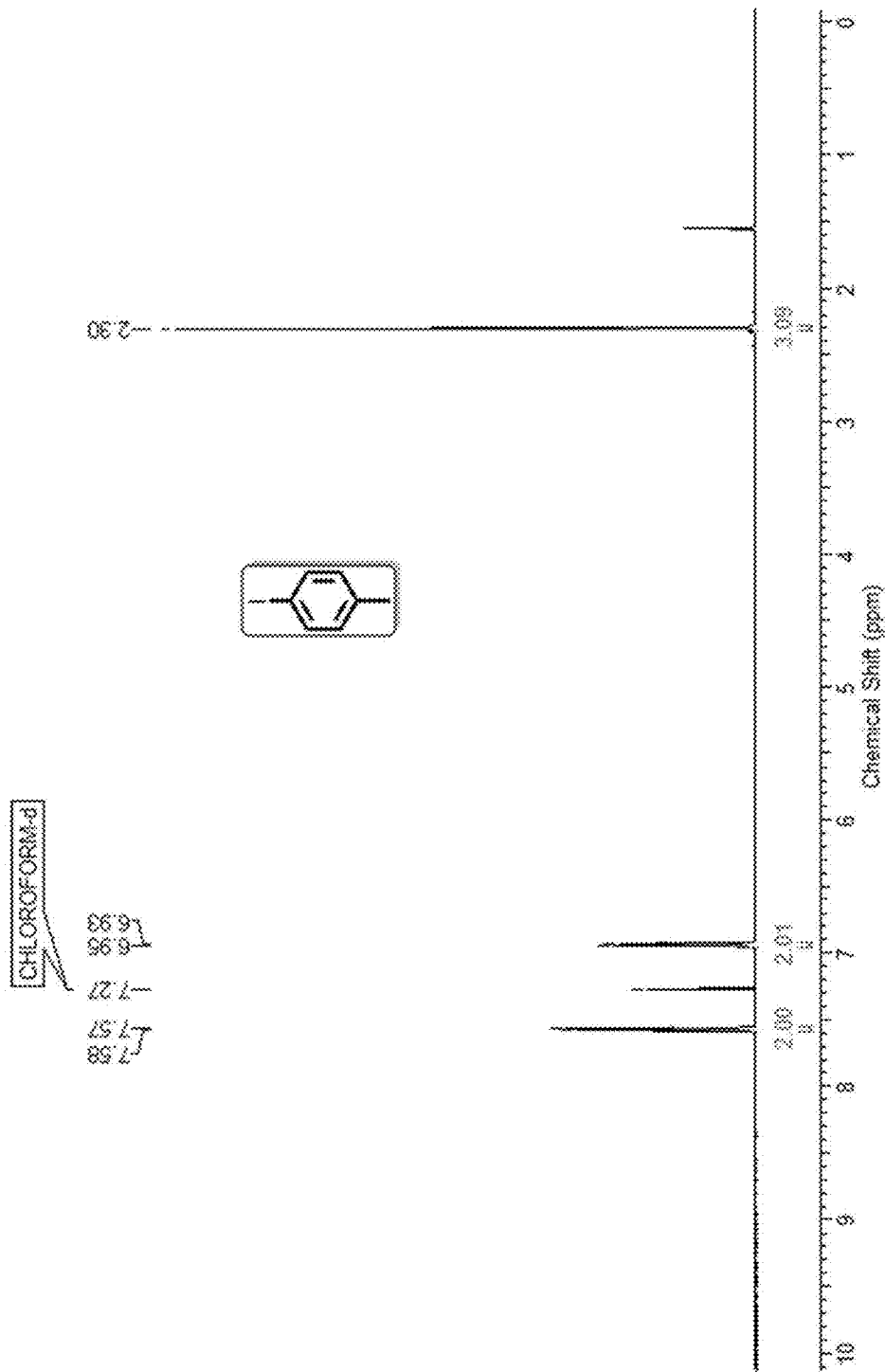
Figure 42:
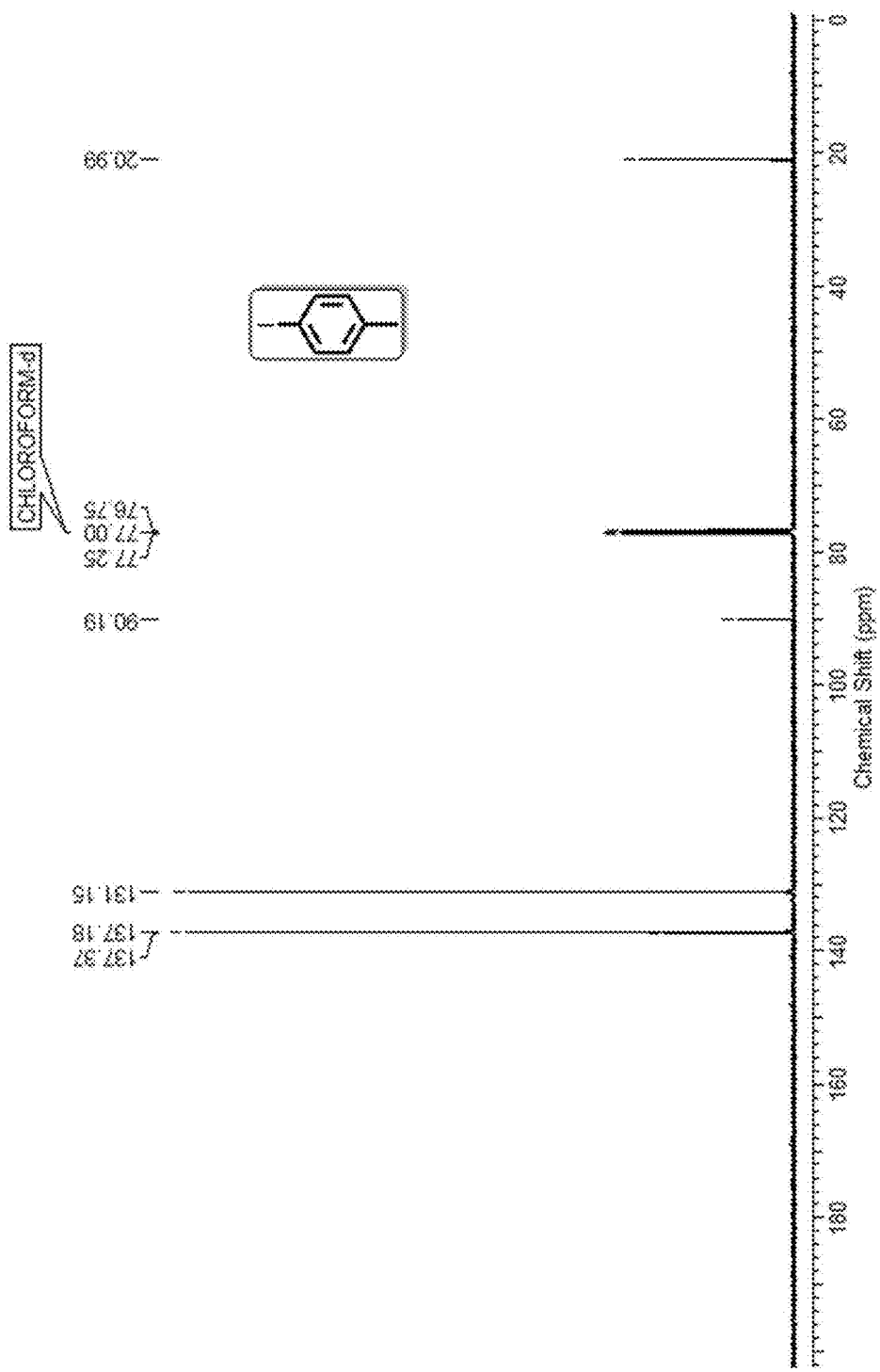
Figure 43:
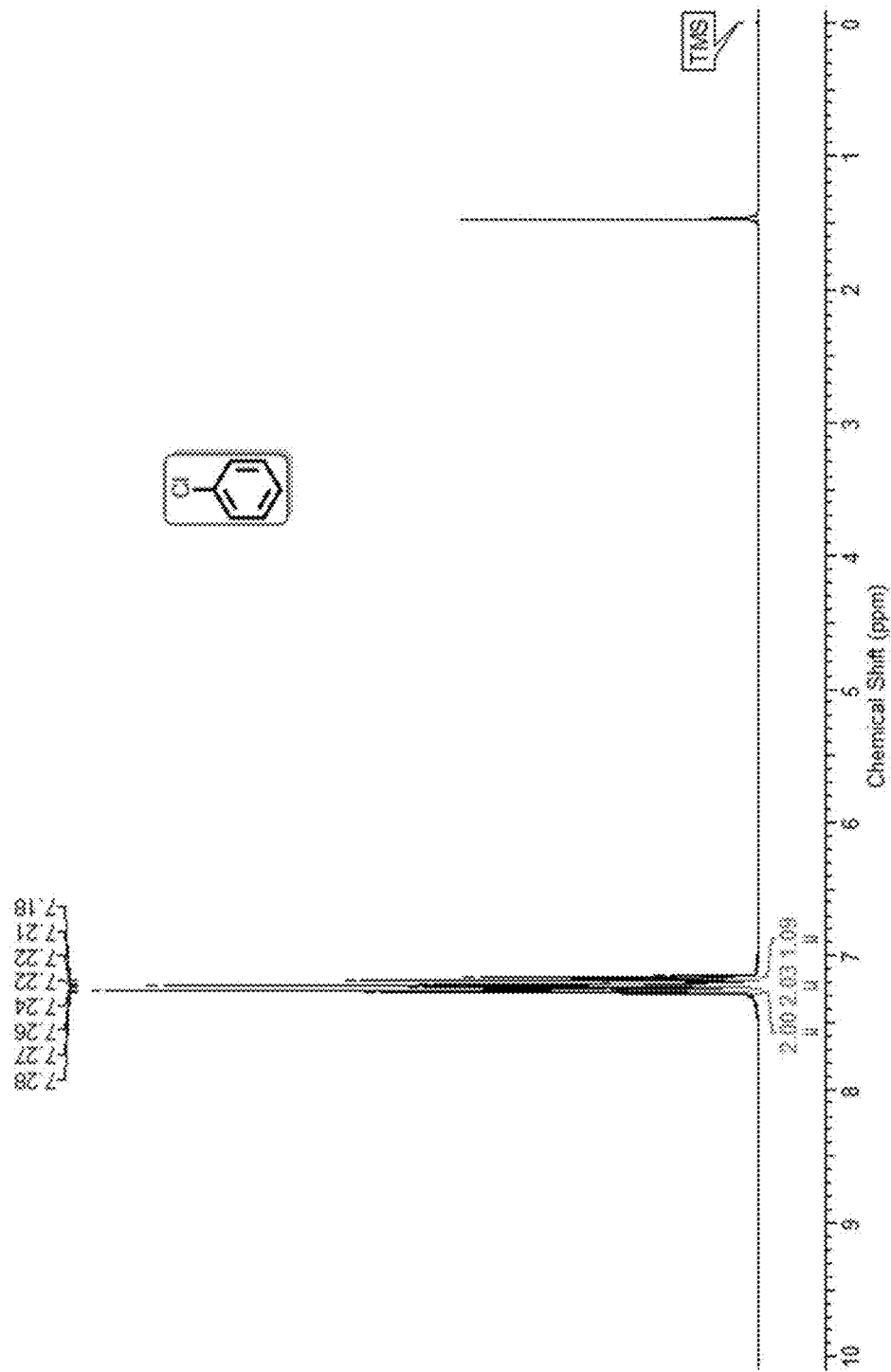
Figure 44:
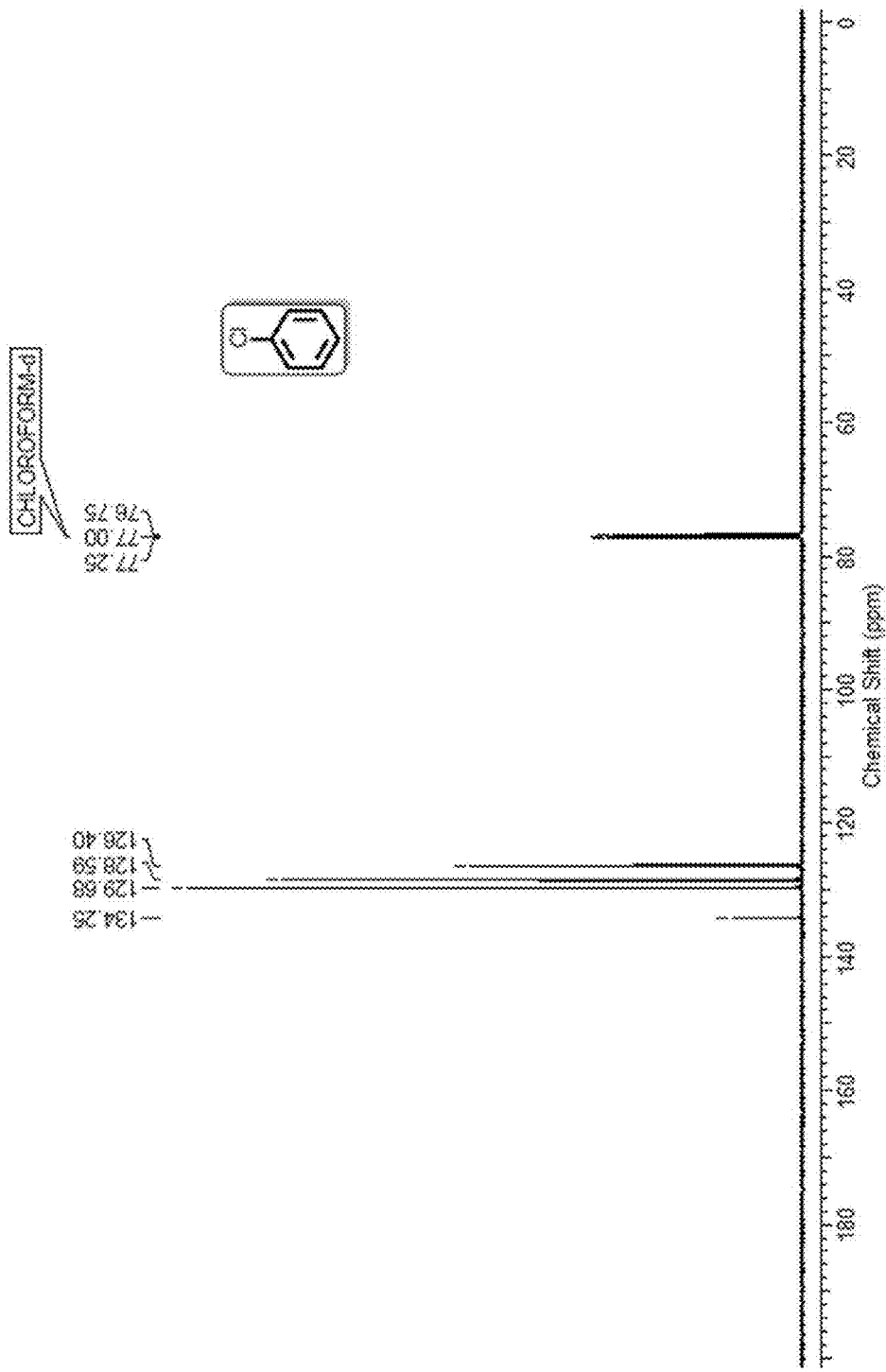
Figure 45:
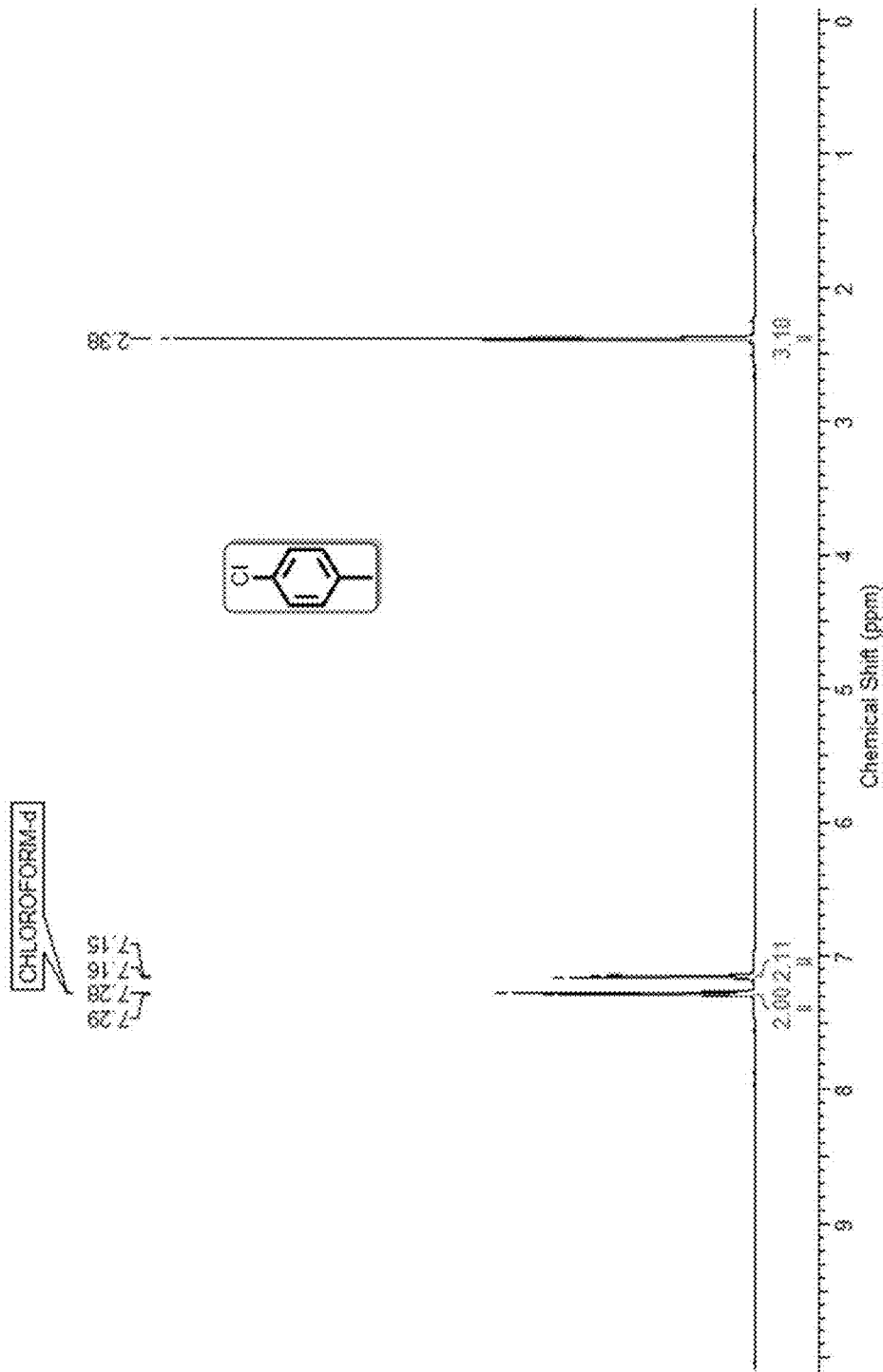
Figure 46:
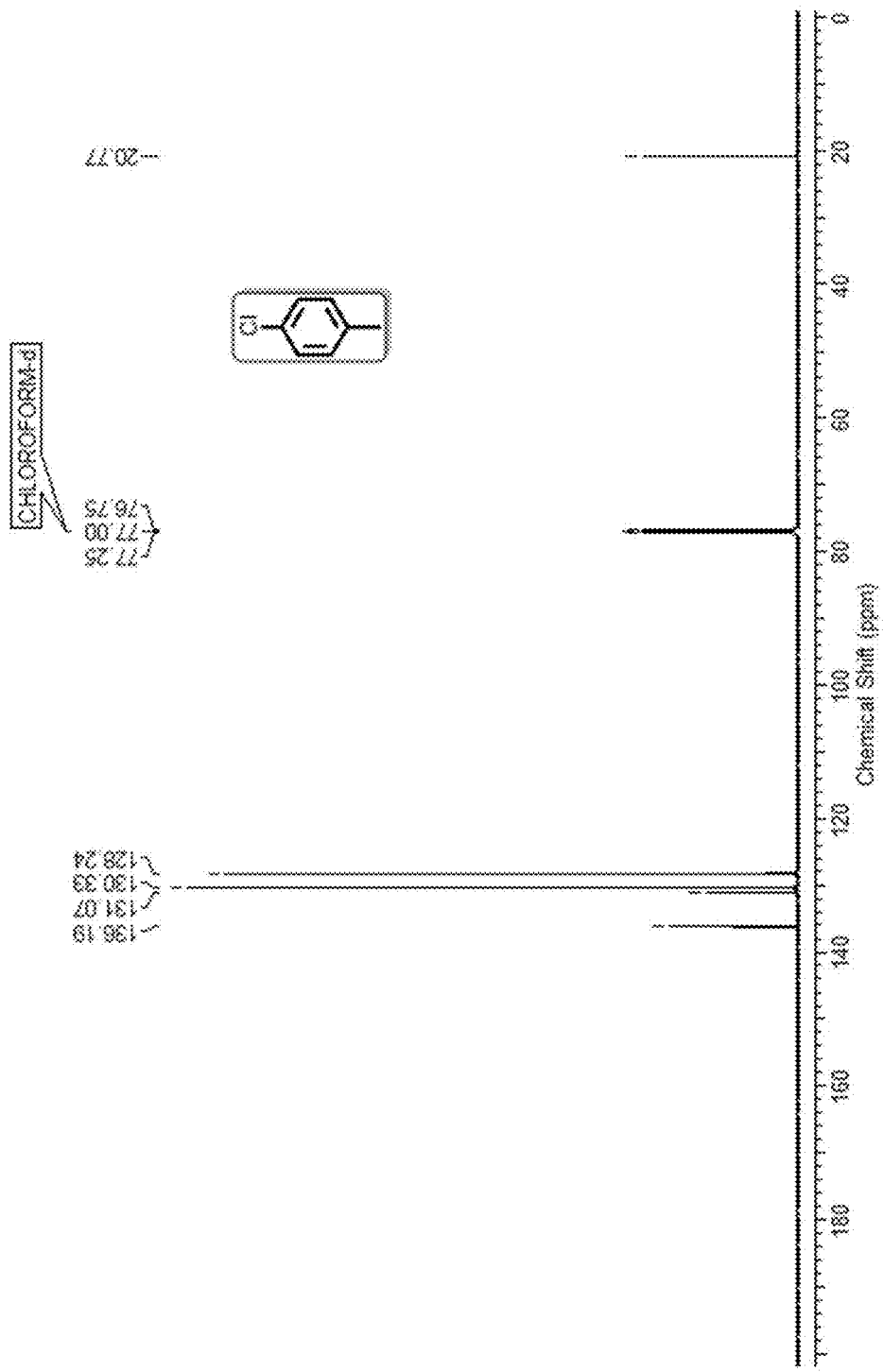
Figure 47:
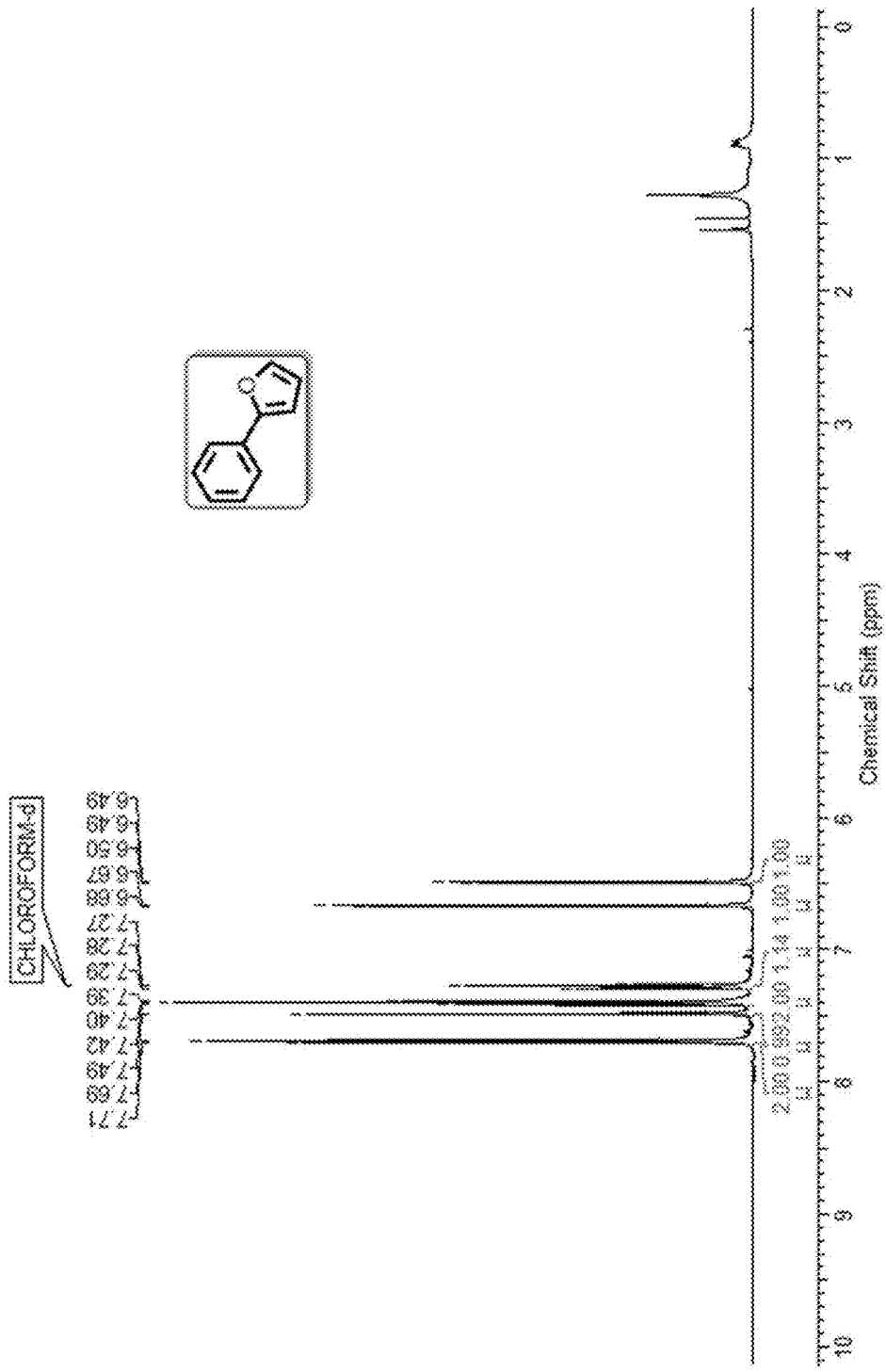
Figure 48:
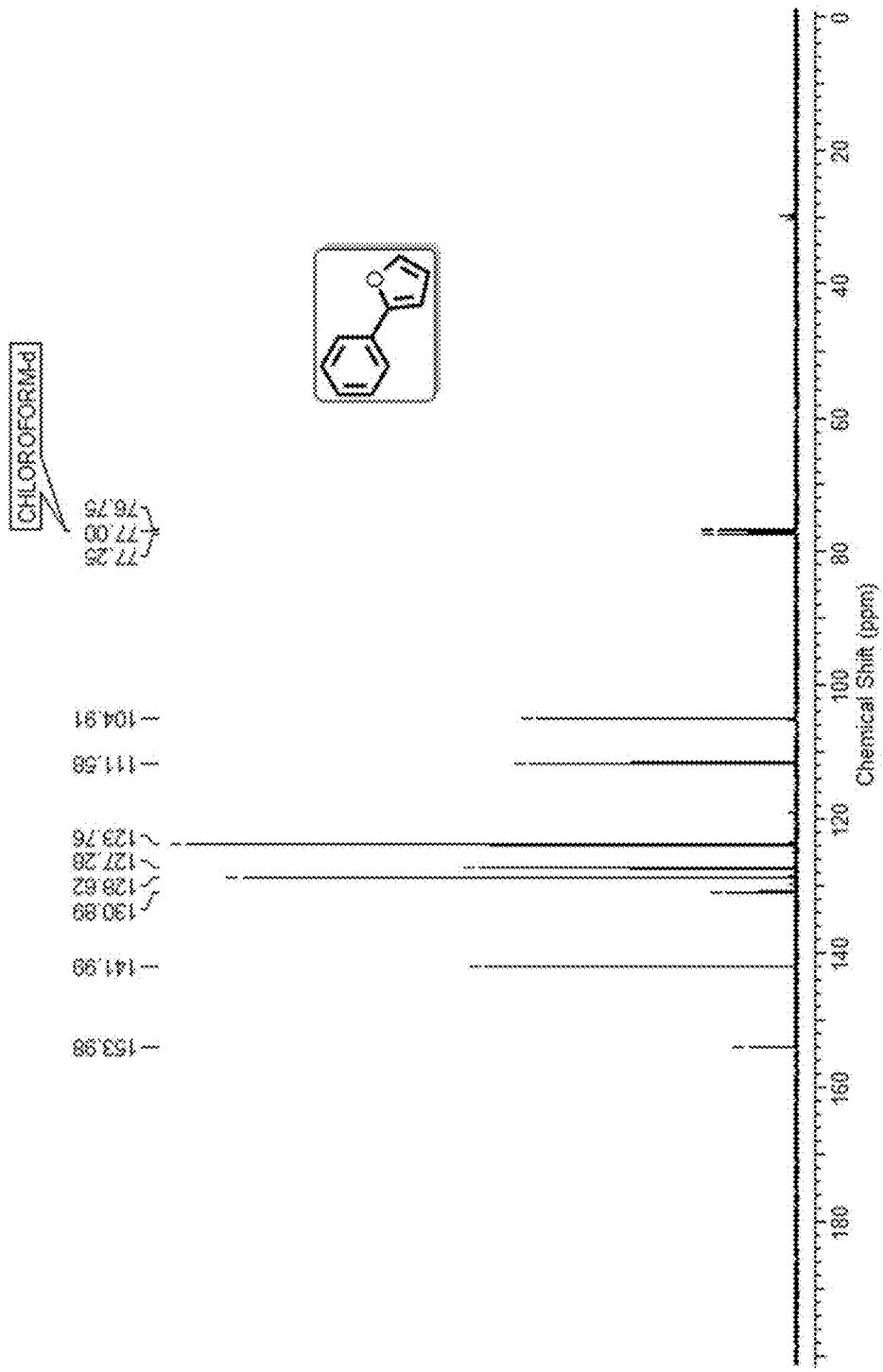
Figure 49:
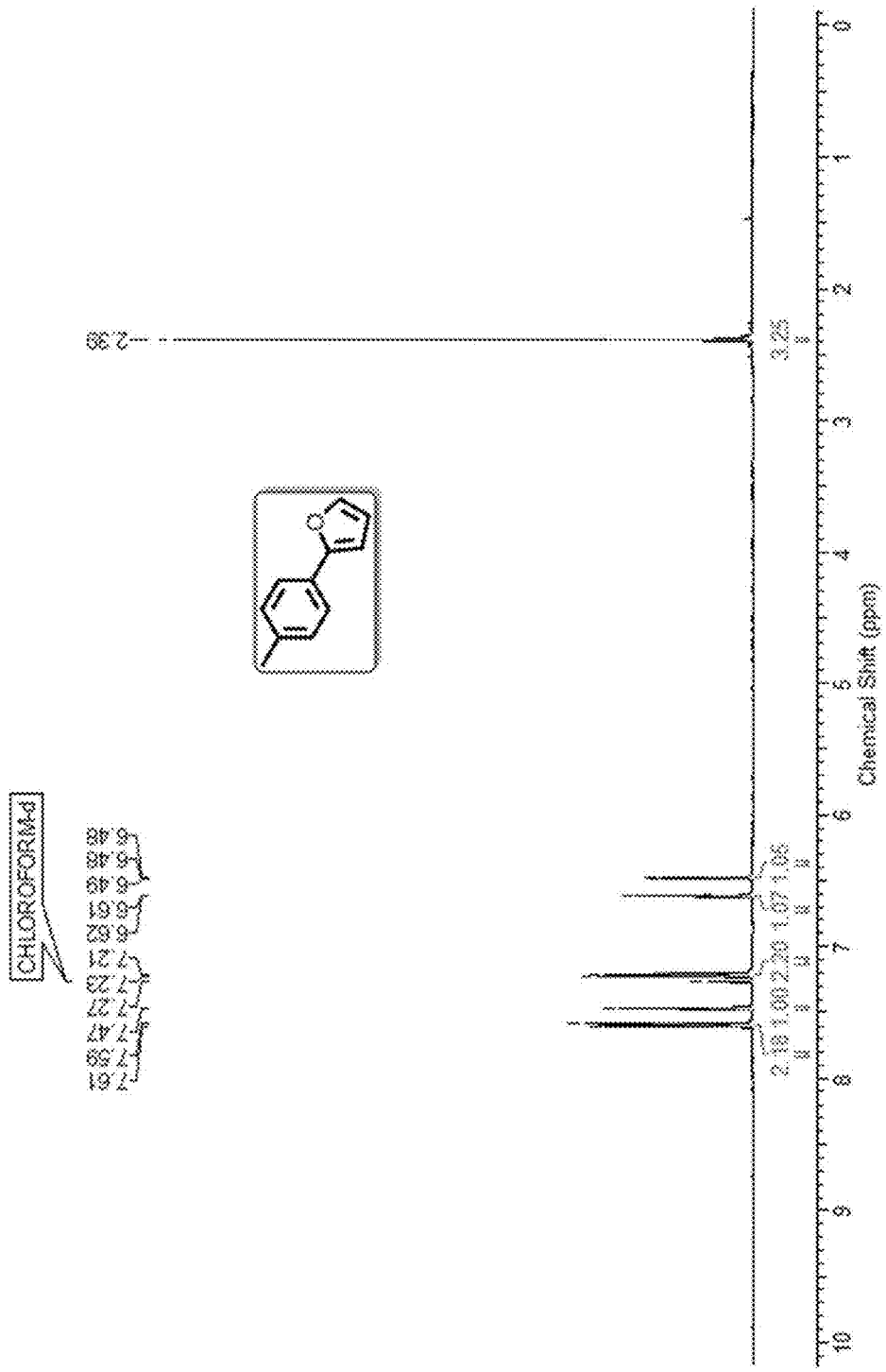
Figure 50:
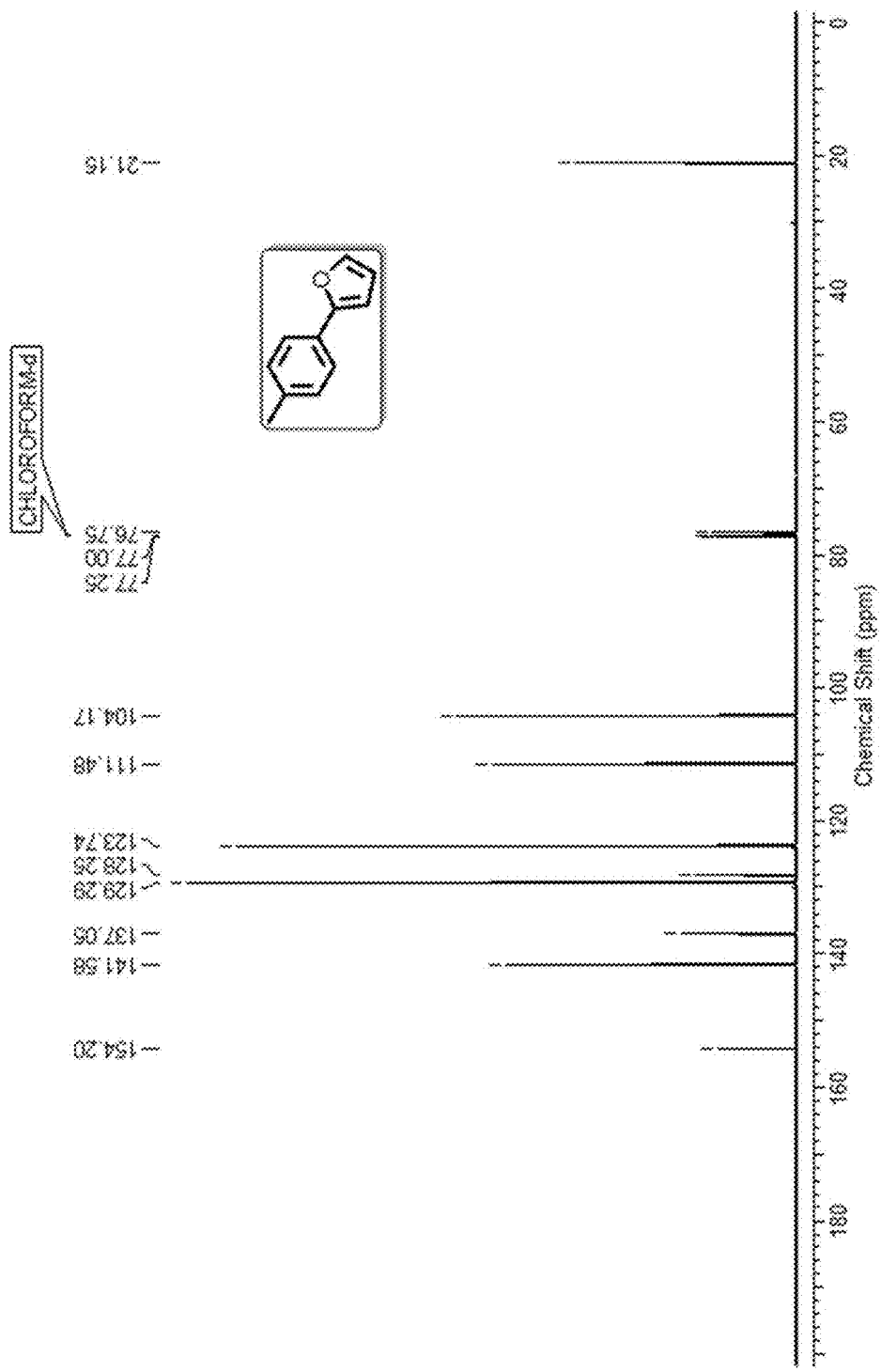
Figure 51:
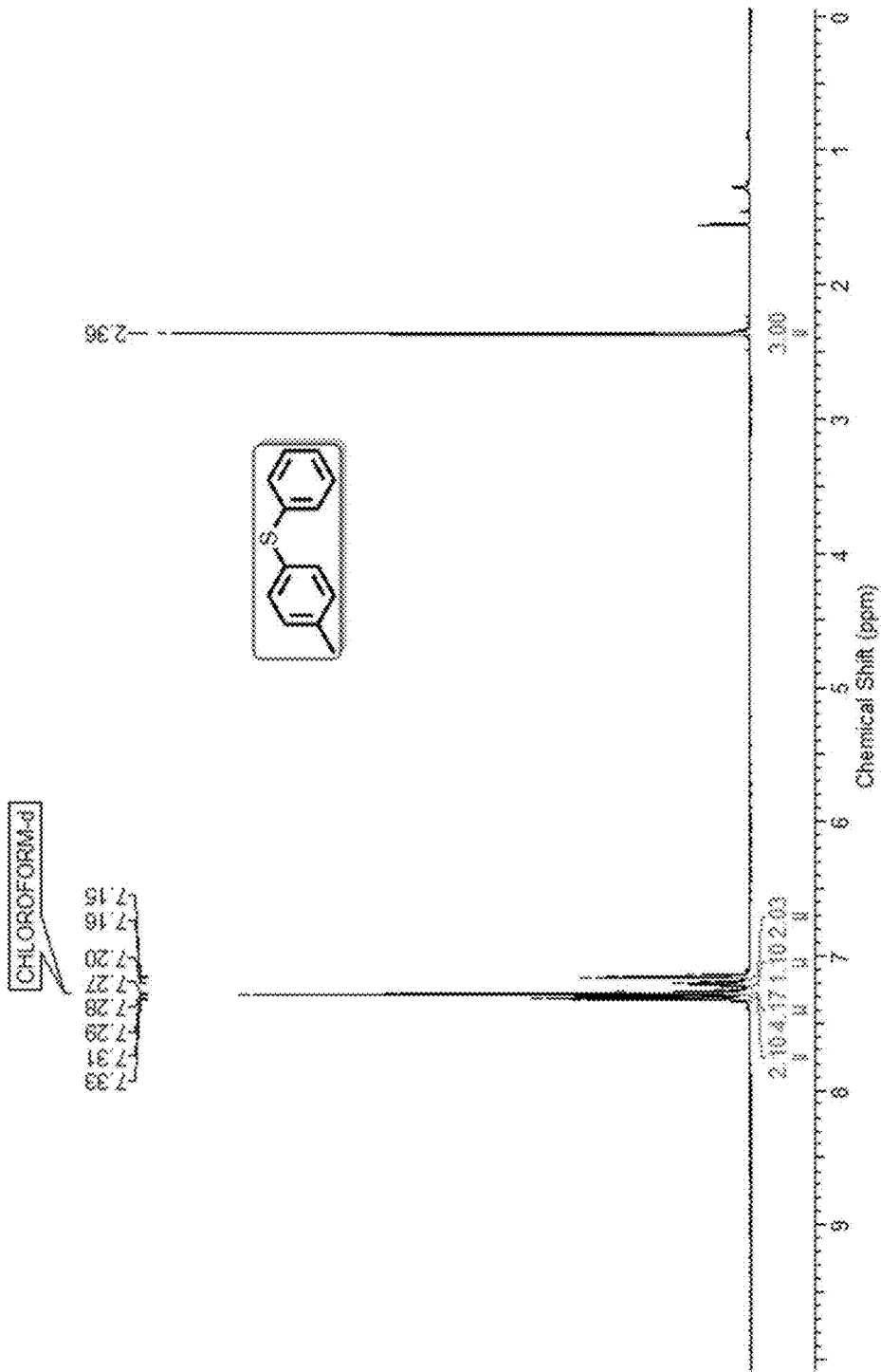
Figure 52:
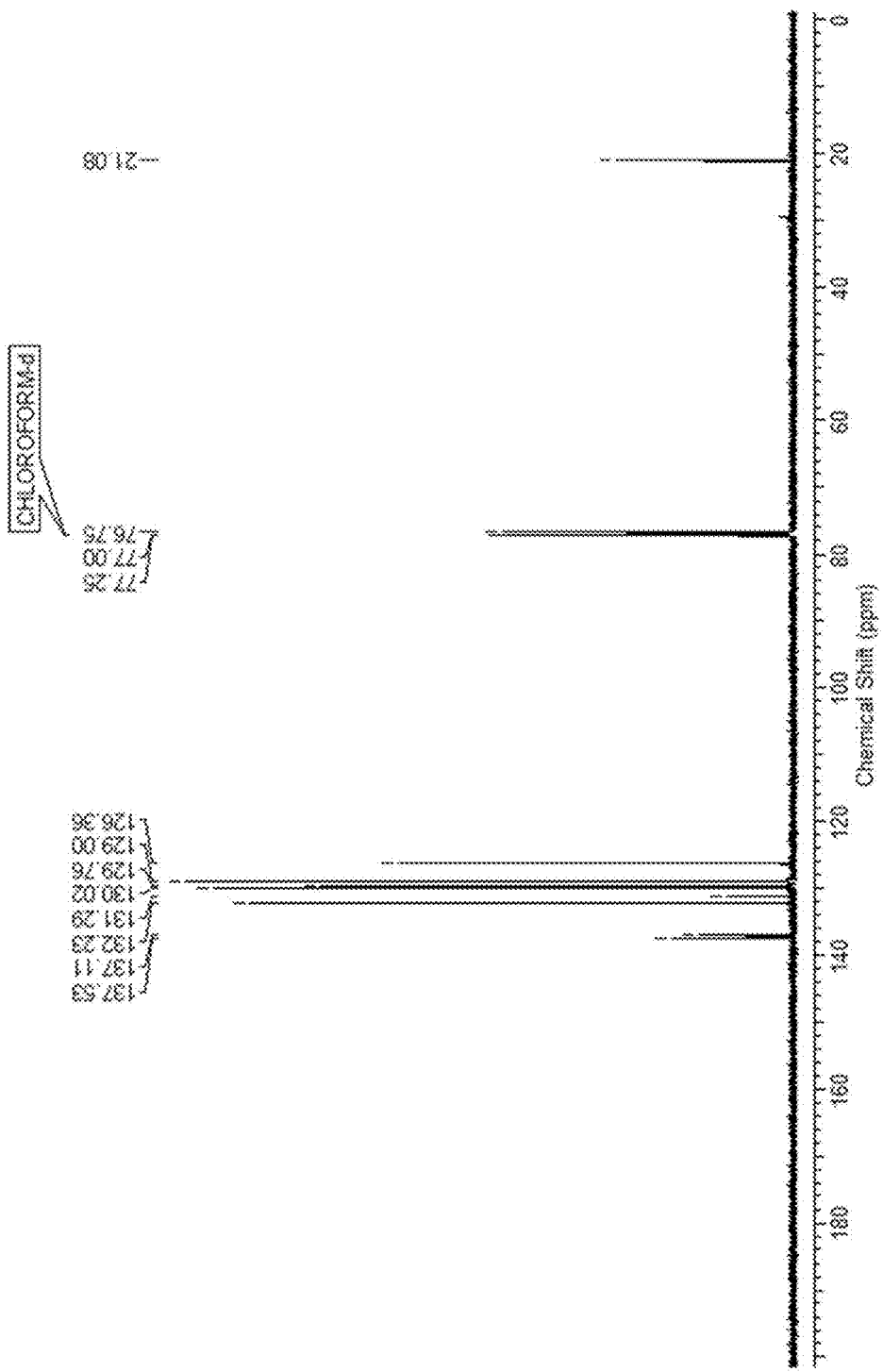
Figure 53:
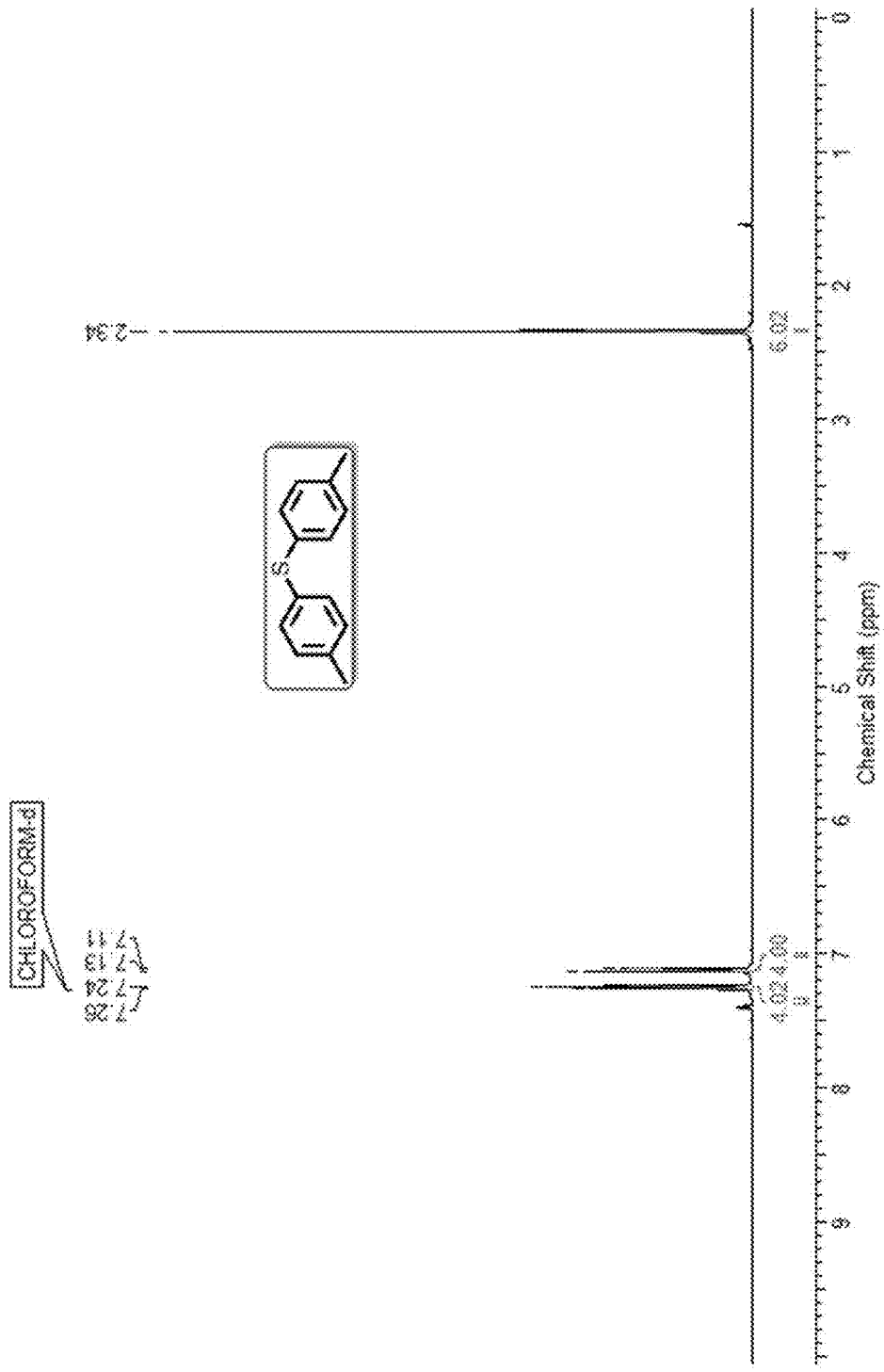
Figure 54:
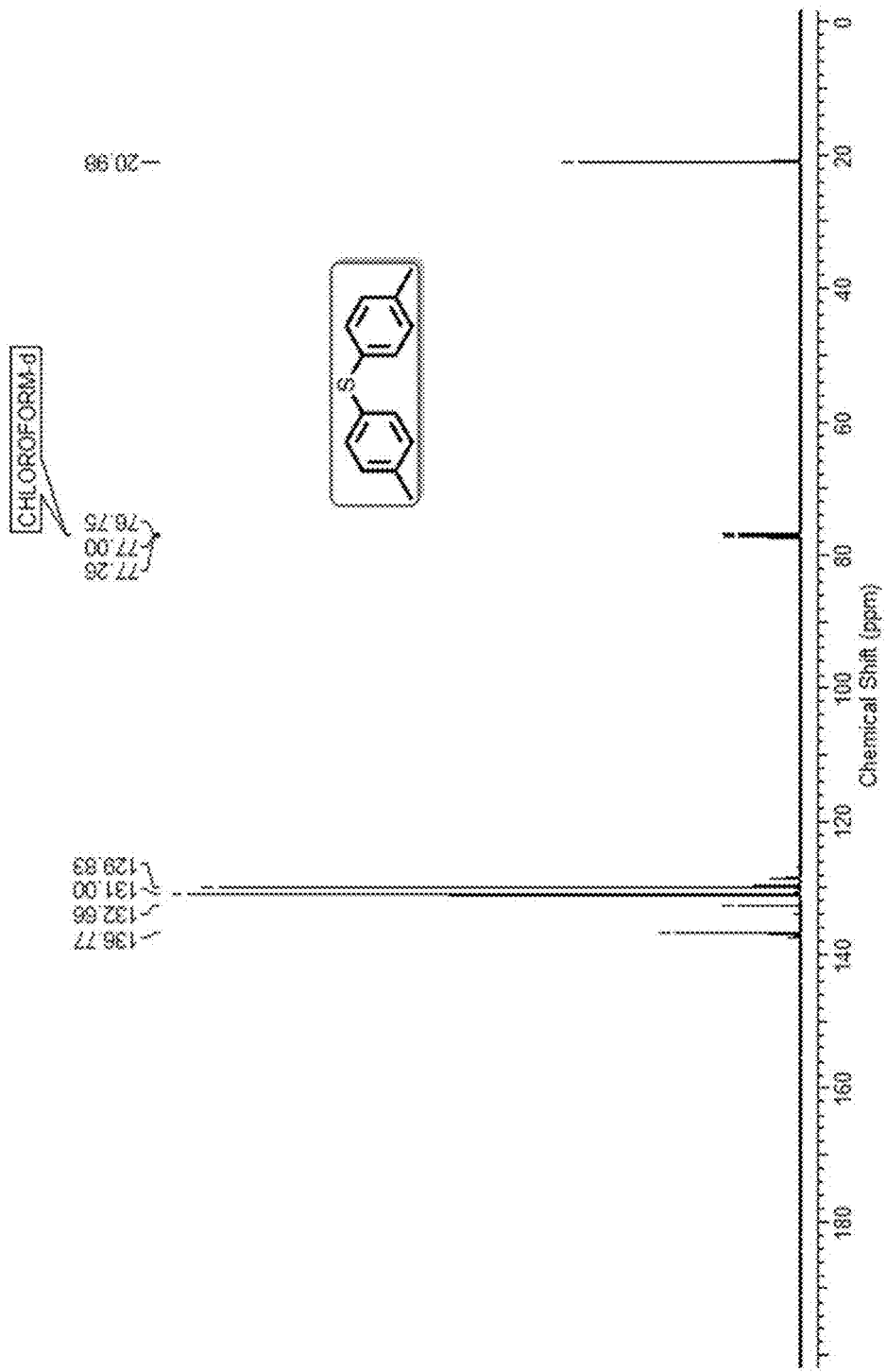
Figure 55:
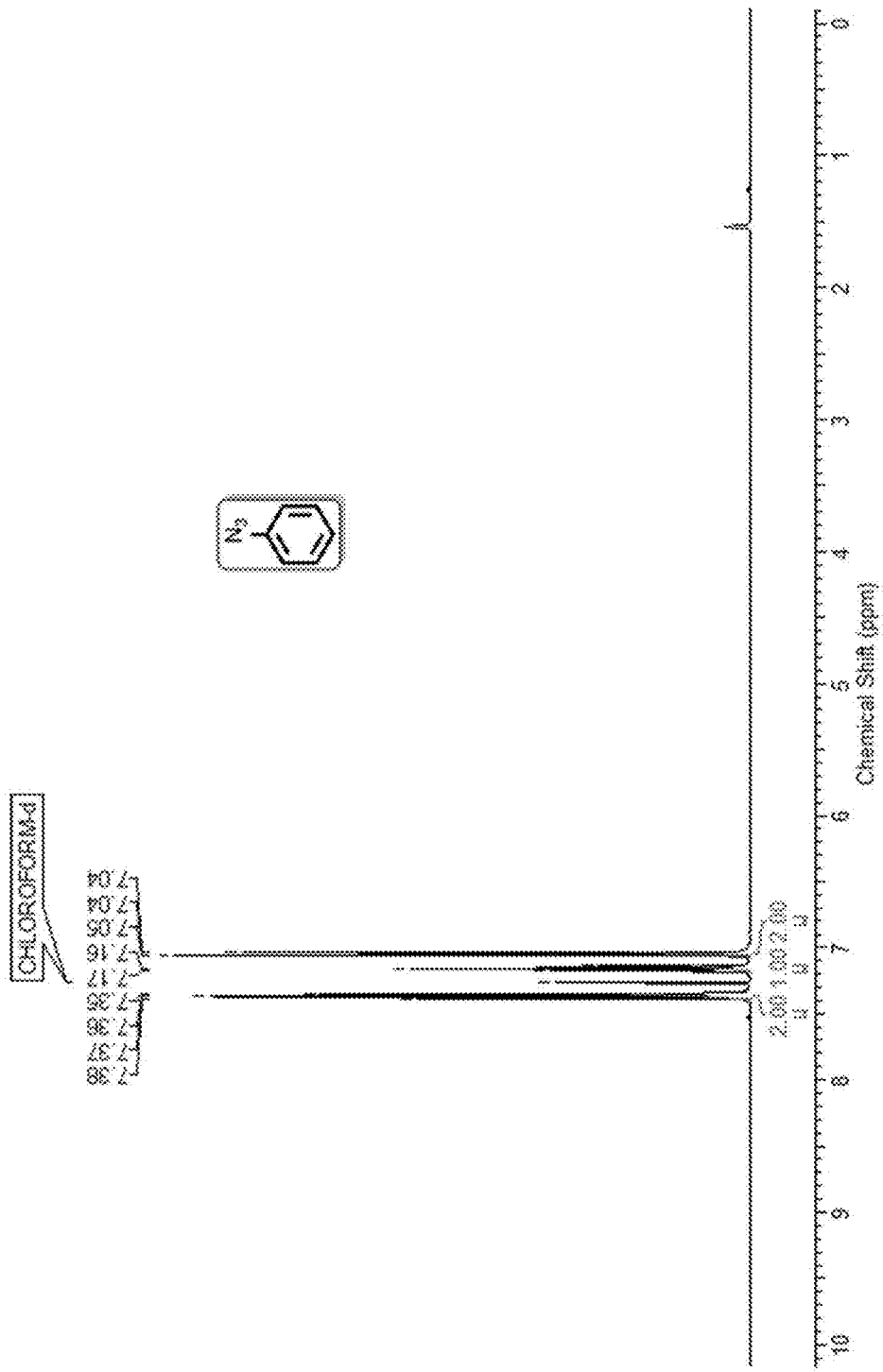
Figure 56:
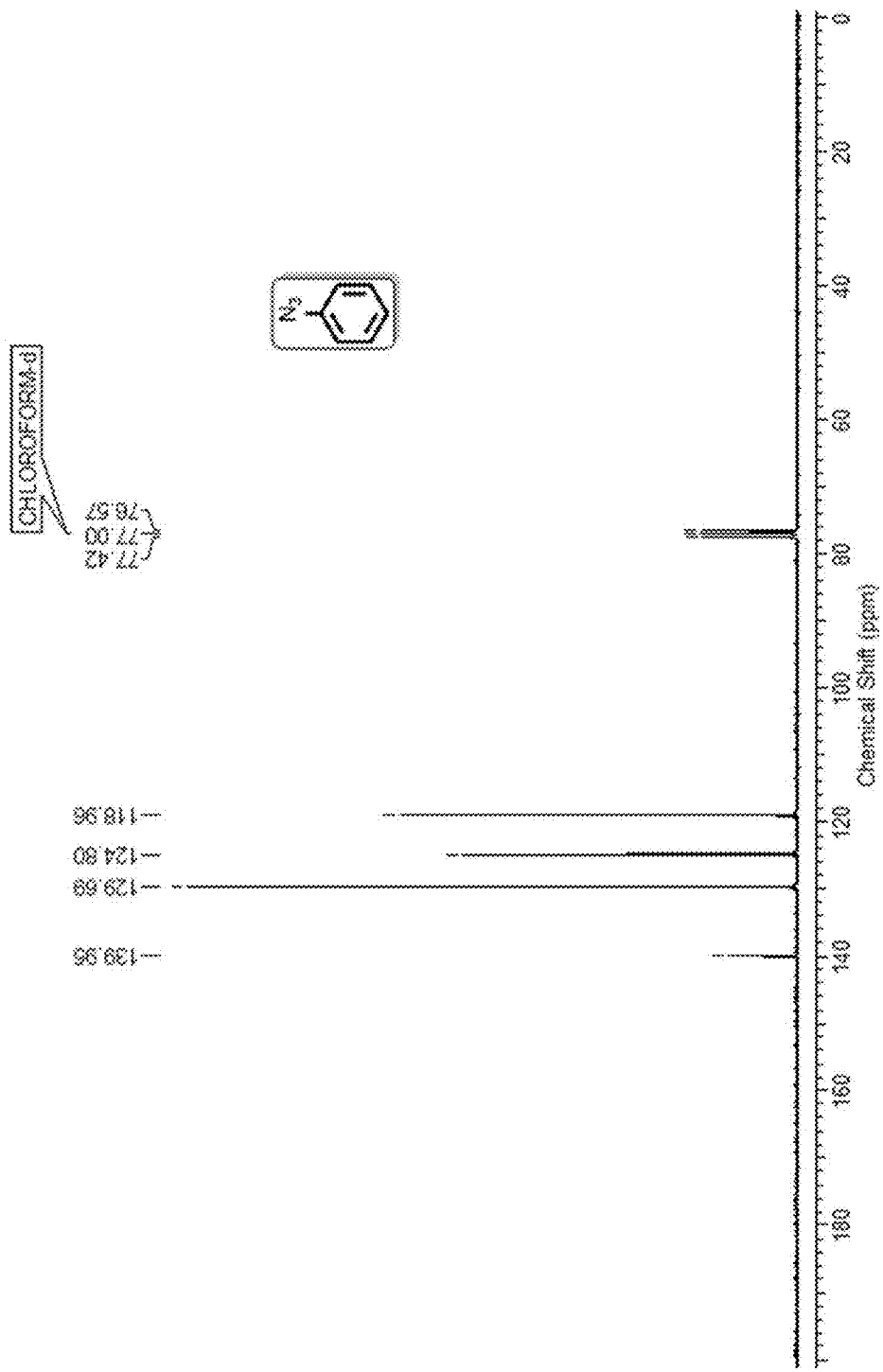
Figure 57:
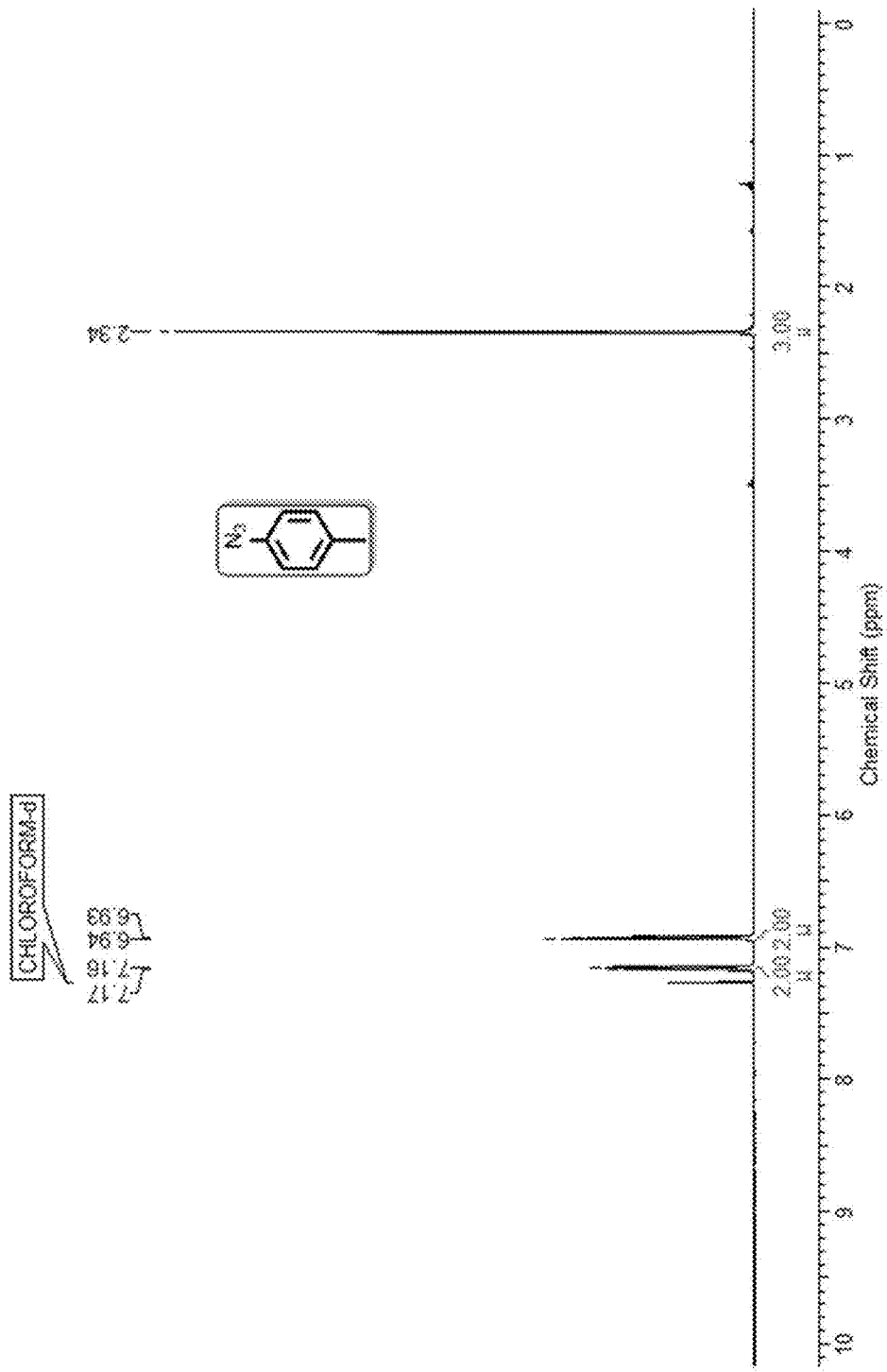
Figure 58:
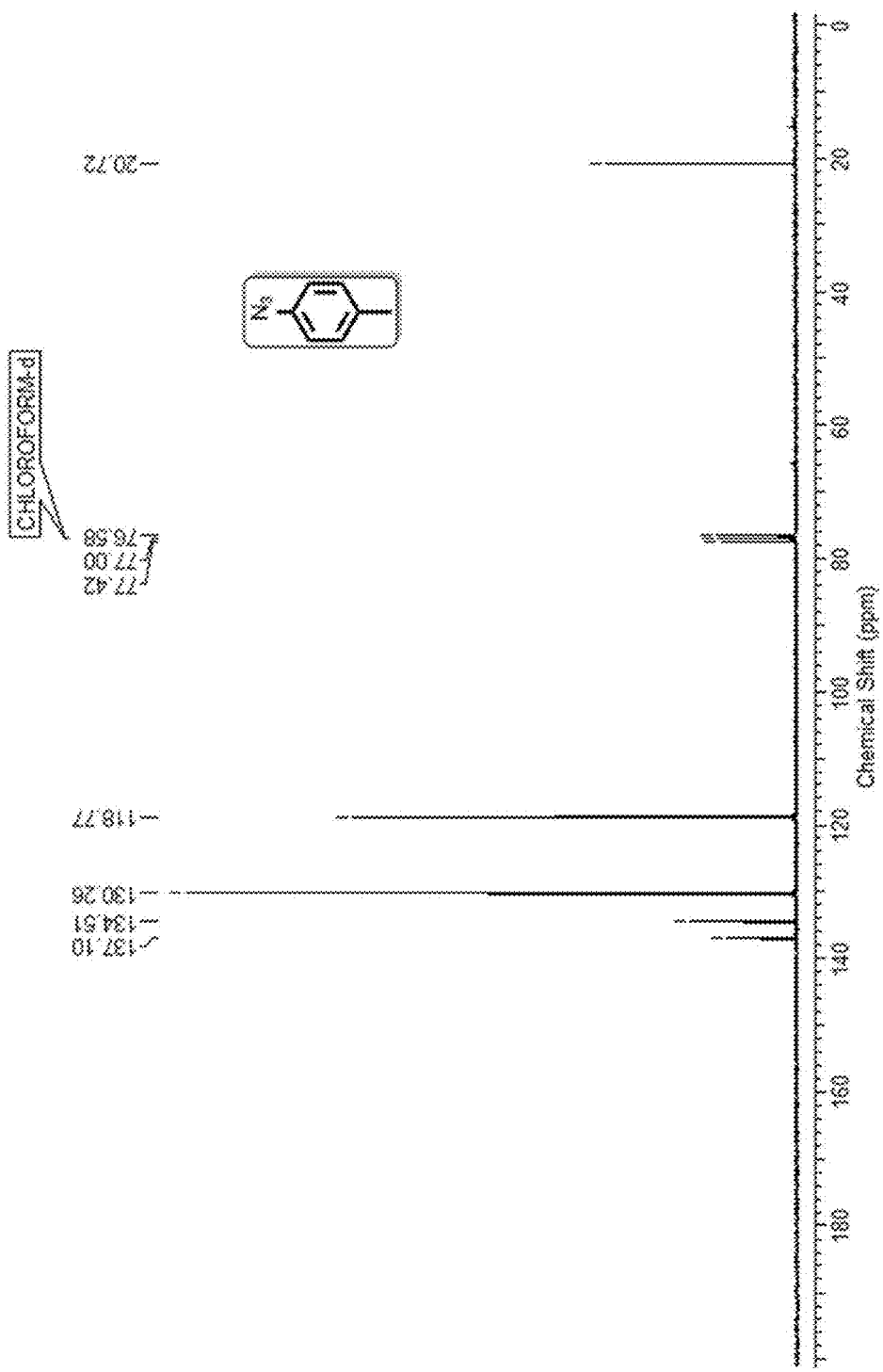
Figure 59B:
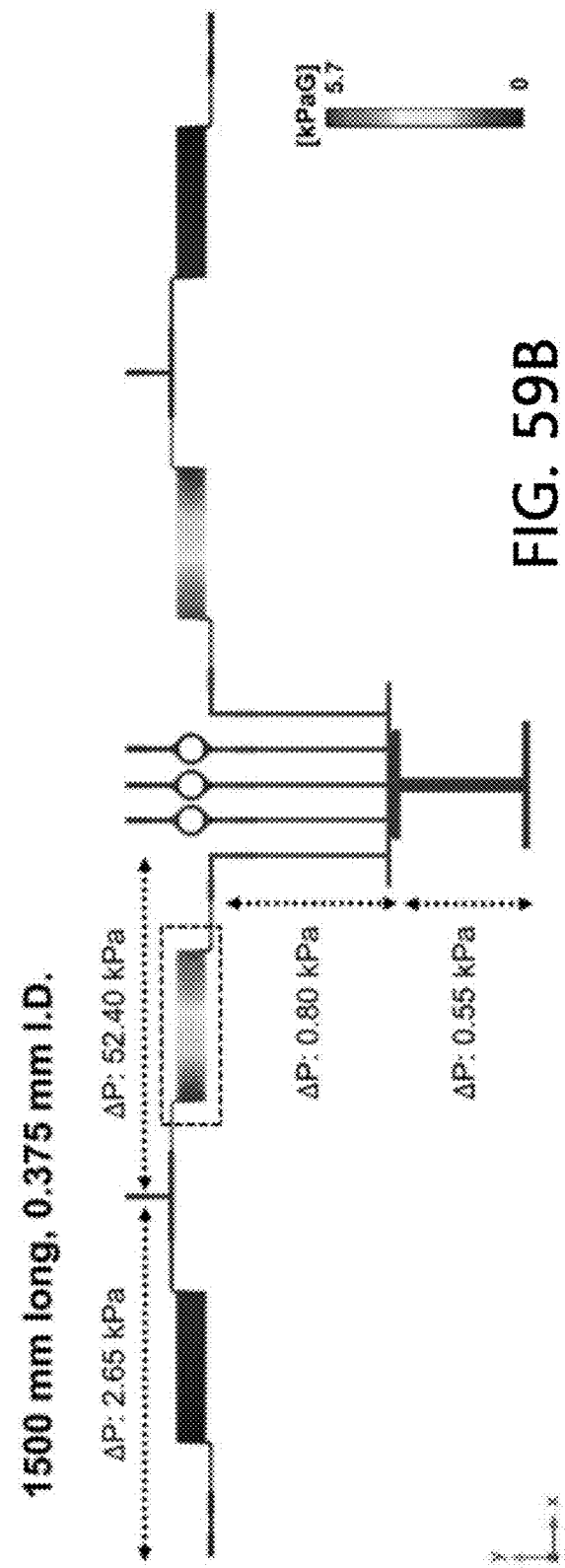
Figure 60A:
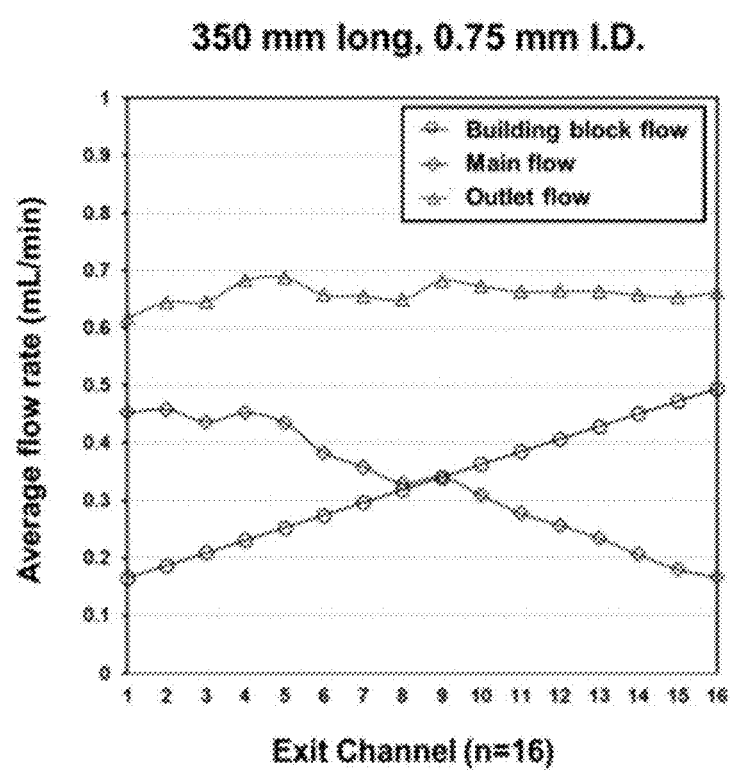
FIGS. 60A and 60B are graphs comparing the average flow rate in each capillary when the length and diameter of the duct are configured differently according to an exemplary embodiment of the present invention.
Figure 60B:
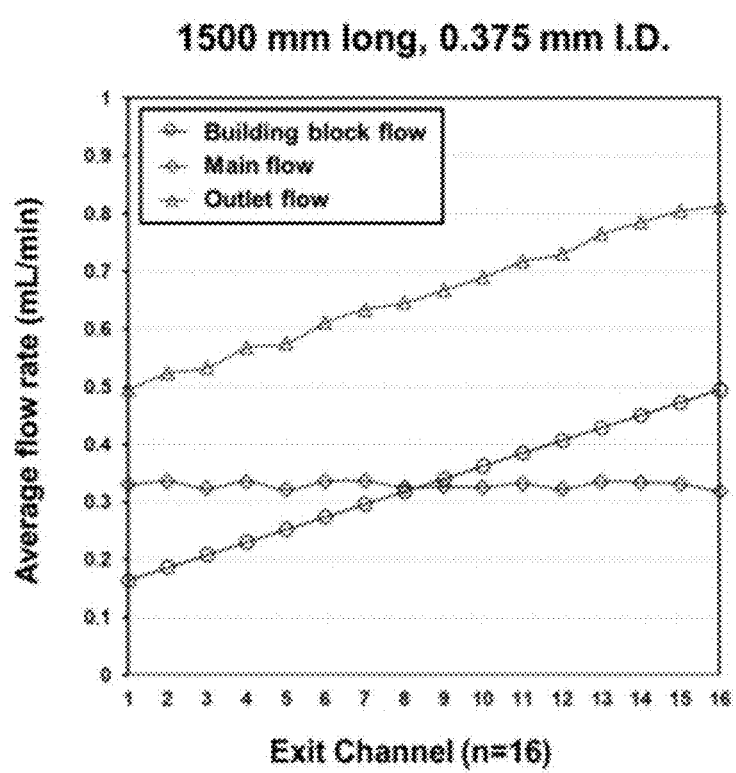

FIG. 13 shows that 96 conditions in 16 reactors may be screened in 6 sequences at different times. In order to find optimal conditions for an aryl diazonium-based chemical library, the flow parallel synthesizer according to the present invention may be used to screen for reaction variables in reaction time (30 to 900 seconds) or/and concentration.

Figure 14:
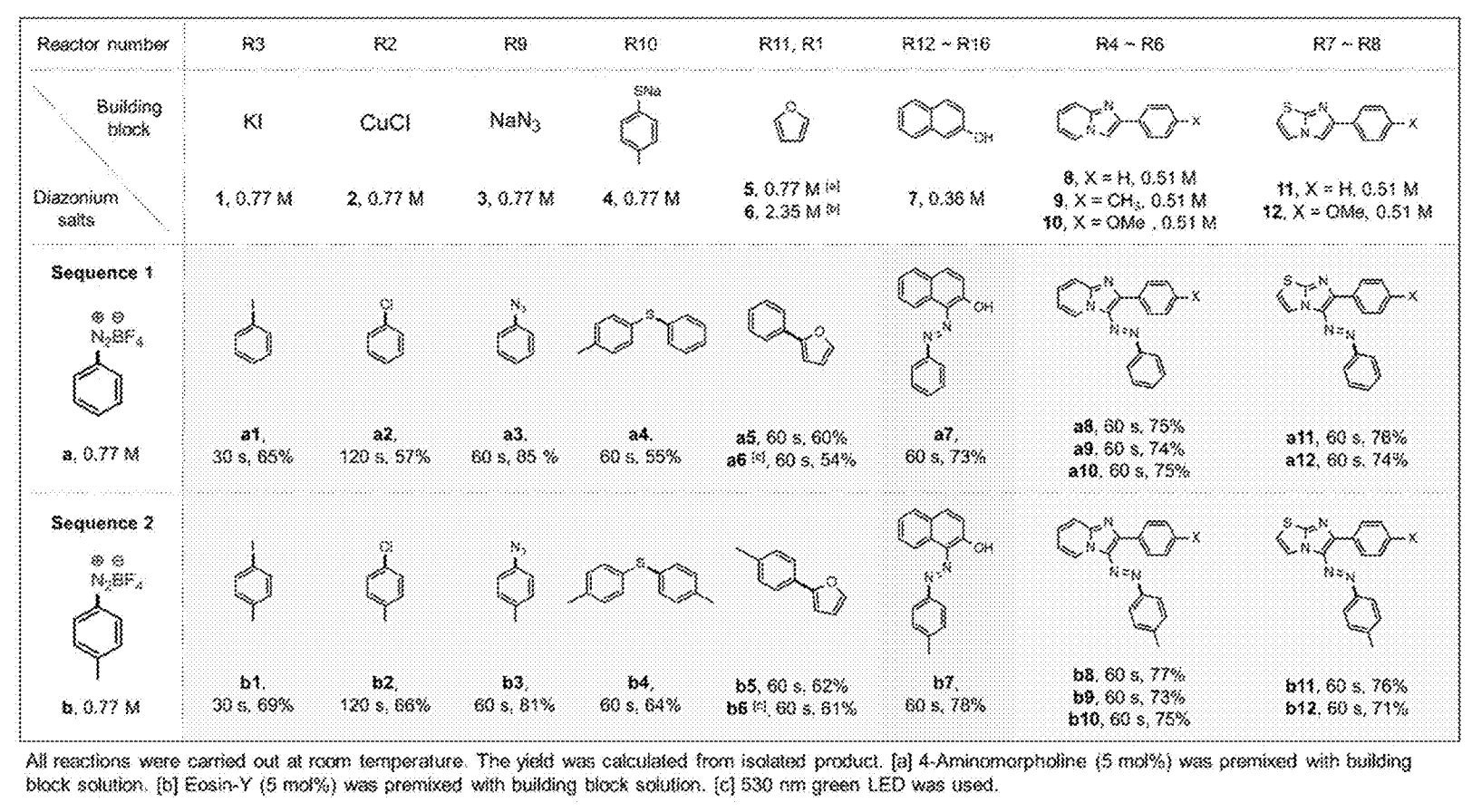

Optimization results of 96 reaction conditions are shown in Table 3 and FIG. 14 below.

TABLE 3

| Total | Rx. type | Reactor # | Concentration of second reactant (building block) | Reaction time | Product | Yield, % [e] | Batch yield, % [e] | Capillary yield, % [e] |
|---|---|---|---|---|---|---|---|---|
| 1 | a1 | R3 | 0.77 M | $t_r$ = 30 s | 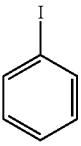 | 65 | 72 | 75 |
| 2 | | | | $t_r$ = 60 s | | 61 | 30 min | 30 s |
| 3 | | | | $t_r$ = 120 s | | 63 | | |
| 4 | | | | $t_r$ = 300 s | | 62 | | |
| 5 | | | | $t_r$ = 600 s | | 60 | | |
| 6 | | | | $t_r$ = 900 s | | 58 | | |
| 7 | a2 | R2 | 0.77 M | $t_r$ = 30 s | 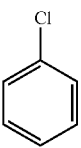 | 30 | 64 | 66 |
| 8 | | | | $t_r$ = 60 s | | 45 | 30 min | 120 s |
| 9 | | | | $t_r$ = 120 s | | 57 | | |
| 10 | | | | $t_r$ = 300 s | | 56 | | |
| 11 | | | | $t_r$ = 600 s | | 53 | | |
| 12 | | | | $t_r$ = 900 s | | 46 | | |
| 13 | a3 | R9 | 0.77 M | $t_r$ = 30 s | 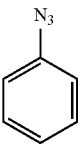 | 70 | 89 | 91 |
| 14 | | | | $t_r$ = 60 s | | 86 | 30 min | 60 s |
| 15 | | | | $t_r$ = 120 s | | 87 | | |
| 16 | | | | $t_r$ = 300 s | | 85 | | |
| 17 | | | | $t_r$ = 600 s | | 82 | | |
| 18 | | | | $t_r$ = 900 s | | 79 | | |
| 19 | a4 | R10 | 0.77 M | $t_r$ = 30 s | 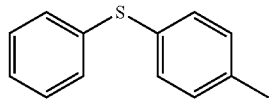 | 48 | 60 | 64 |
| 20 | | | | $t_r$ = 60 s | | 55 | 2 h | 60 s |
| 21 | | | | $t_r$ = 120 s | | 54 | | |
| 22 | | | | $t_r$ = 300 s | | 53 | | |
| 23 | | | | $t_r$ = 600 s | | 51 | | |
| 24 | | | | $t_r$ = 900 s | | 47 | | |
| 25 | a5 [c] | R11 | 0.77 M | $t_r$ = 30 s | 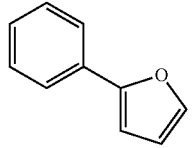 [SMILES: c1ccc(-c2ccco2)cc1] | 54 | 55 | 62 |
| 26 | | | | $t_r$ = 60 s | | 60 | 30 min | 60 s |
| 27 | | | | $t_r$ = 120 s | | 61 | | |
| 28 | | | | $t_r$ = 300 s | | 60 | | |
| 29 | | | | $t_r$ = 600 s | | 58 | | |
| 30 | | | | $t_r$ = 900 s | | 56 | | |
| 31 | a6 [d] | R1 | 2.35 M | $t_r$ = 30 s | 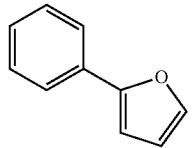 [SMILES: c1ccc(-c2ccco2)cc1] | n.r | 61 | 55 |
| 32 | | | | $t_r$ = 60 s | | 6 | 2 h | 600 s |
| 33 | | | | $t_r$ = 120 s | | 15 | | |
| 34 | | | | $t_r$ = 300 s | | 32 | | |
| 35 | | | | $t_r$ = 600 s | | 54 | | |
| 36 | | | | $t_r$ = 900 s | | 45 | | |
| 37 | a7 | R12 | 0.64 M | $t_r$ = 30 s | 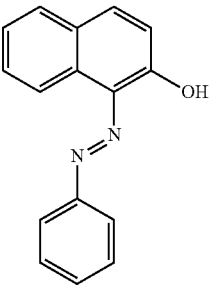 [SMILES: Oc1ccc2ccccc2c1/N=N/c1ccccc1] | Clog | 77 | Clog |
| 38 | | | | $t_r$ = 60 s | | | 1 h | |
| 39 | | | | $t_r$ = 120 s | | | | |
| 40 | | | | $t_r$ = 300 s | | | | |
| 41 | | | | $t_r$ = 600 s | | | | |
| 42 | | | | $t_r$ = 900 s | | | | |

TABLE 3-continued

| Total | Rx. type | Reactor # | Concentration of second reactant (building block) | Reaction time | Product | Yield, % [e] | Batch yield, % [e] | Capillary yield, % [e] |
|---|---|---|---|---|---|---|---|---|
| 43 | a7 | R13 | 0.51 M | $t_r$ = 30 s | 1-(phenyldiazenyl)naphthalen-2-ol | Clog | 79 | Clog |
| 44 | | | | $t_r$ = 60 s | | | 1 h | |
| 45 | | | | $t_r$ = 120 s | | | | |
| 46 | | | | $t_r$ = 300 s | | | | |
| 47 | | | | $t_r$ = 600 s | | | | |
| 48 | | | | $t_r$ = 900 s | | | | |
| 49 | a7 | R14 | 0.38 M | $t_r$ = 30 s | 1-(phenyldiazenyl)naphthalen-2-ol | 57 | 78 | 79 |
| 50 | | | | $t_r$ = 60 s | | 74 | 1 h | 60 s |
| 51 | | | | $t_r$ = 120 s | | 76 | | |
| 52 | | | | $t_r$ = 300 s | | 71 | | |
| 53 | | | | $t_r$ = 600 s | | Clog | | |
| 54 | | | | $t_r$ = 900 s | | Clog | | |
| 55 | a7 | R15 | 0.32 M | $t_r$ = 30 s | 1-(phenyldiazenyl)naphthalen-2-ol | 57 | 76 | 78 |
| 56 | | | | $t_r$ = 60 s | | 73 | 1 h | 60 s |
| 57 | | | | $t_r$ = 120 s | | 71 | | |
| 58 | | | | $t_r$ = 300 s | | 70 | | |
| 59 | | | | $t_r$ = 600 s | | Clog | | |
| 60 | | | | $t_r$ = 900 s | | Clog | | |
| 61 | a7 | R16 | 0.26 M | $t_r$ = 30 s | 1-(phenyldiazenyl)naphthalen-2-ol | 55 | 75 | 80 |
| 62 | | | | $t_r$ = 60 s | | 71 | 1 h | 60 s |
| 63 | | | | $t_r$ = 120 s | | 72 | | |
| 64 | | | | $t_r$ = 300 s | | 71 | | |
| 65 | | | | $t_r$ = 600 s | | Clog | | |
| 66 | | | | $t_r$ = 900 s | | Clog | | |
| 67 | a8 | R4 | 0.51 M | $t_r$ = 30 s | 2-phenylimidazo[1,2-a]pyridine derivative | 61 | 78 | 80 |
| 68 | | | | $t_r$ = 60 s | | 75 | 8 h | 60 s |
| 69 | | | | $t_r$ = 120 s | | 76 | | |
| 70 | | | | $t_r$ = 300 s | | 75 | | |
| 71 | | | | $t_r$ = 600 s | | 70 | | |
| 72 | | | | $t_r$ = 900 s | | 69 | | |

TABLE 3-continued

| Total | Rx. type | Reactor # | Concentration of second reactant (building block) | Reaction time | Product | Yield, % [e] | Batch yield, % [e] | Capillary yield, % [e] |
|---|---|---|---|---|---|---|---|---|
| 73 | a9 | R5 | 0.51 M | $t_r$ = 30 s | (imidazo[1,2-a]pyridine with 4-methylphenyl and phenyldiazenyl) | 66 | 79 | 82 |
| 74 | | | | $t_r$ = 60 s | | 84 | 8 h | 60 s |
| 75 | | | | $t_r$ = 120 s | | 83 | | |
| 76 | | | | $t_r$ = 300 s | | 80 | | |
| 77 | | | | $t_r$ = 600 s | | 78 | | |
| 78 | | | | $t_r$ = 900 s | | 76 | | |
| 79 | a10 | R6 | 0.51 M | $t_r$ = 30 s | (imidazo[1,2-a]pyridine with 4-OMe-phenyl and phenyldiazenyl) | 69 | 83 | 89 |
| 80 | | | | $t_r$ = 60 s | | 85 | 8 h | 60 s |
| 81 | | | | $t_r$ = 120 s | | 87 | | |
| 82 | | | | $t_r$ = 300 s | | 85 | | |
| 83 | | | | $t_r$ = 600 s | | 81 | | |
| 84 | | | | $t_r$ = 900 s | | 80 | | |
| 85 | a11 | R7 | 0.51 M | $t_r$ = 30 s | (imidazo[2,1-b]thiazole with phenyl and phenylamino) | 64 | 74 | 81 |
| 86 | | | | $t_r$ = 60 s | | 76 | 8 h | 60 s |
| 87 | | | | $t_r$ = 120 s | | 75 | | |
| 88 | | | | $t_r$ = 300 s | | 77 | | |
| 89 | | | | $t_r$ = 600 s | | 71 | | |
| 90 | | | | $t_r$ = 900 s | | 72 | | |
| 91 | a12 | R8 | 0.51 M | $t_r$ = 30 s | (imidazo[2,1-b]thiazole with 4-OMe-phenyl and phenylamino) | 60 | 78 | 80 |
| 92 | | | | $t_r$ = 60 s | | 74 | 8 h | 60 s |
| 93 | | | | $t_r$ = 120 s | | 76 | | |
| 94 | | | | $t_r$ = 300 s | | 75 | | |
| 95 | | | | $t_r$ = 600 s | | 71 | | |
| 96 | | | | $t_r$ = 900 s | | 68 | | |

In Table 3 above, [a] the concentration of the aryl diazonium salt is 0.77M, and the reaction temperature is room temperature. [b] is the residence time in each reactor. [c] Eosin-Y (5 mol %) was pre-mixed with the building block solution. A 530 nm green LED was wrapped around a transparent PFA capillary. [d] 4-Aminomorpholine (5 mol %) was pre-mixed with the building block solution. [e] is the isolated yield.

Example 10

Spectral Data of Synthetic Compounds

Spectral data of the compounds synthesized according to the present invention is as follows, and it was confirmed whether the compound was synthesized by the data of FIGS. 15 to 58.

10-1. (E)-2-Phenyl-3-(phenyldiazenyl)imidazo[1,2-a]pyridine $^1$H NMR (500 MHz, CDCl$_3$) δ=10.04 (d, J=6.9 Hz, 1H), 8.51-8.43 (m, 2H), 7.95-7.85 (m, 3H), 7.59-7.48 (m, 6H), 7.45-7.40 (m, 1H), 7.14 (t, J=6.9 Hz, 1H);

$^{13}$C NMR (125 MHz, CDCl$_3$) δ=153.6, 150.3, 145.7, 132.8, 132.0, 129.9, 129.5, 129.4, 129.3, 129.1, 128.4, 122.0, 117.2, 115.3

10-2. (E)-2-Phenyl-3-(p-tolyldiazenyl)imidazo[1,2-a]pyridine $^1$H NMR (500 MHz, CDCl$_3$) δ=10.05 (d, J=6.9 Hz, 1H), 8.51-8.45 (m, 2H), 7.91 (br. s., 1H), 7.83 (d, J=8.2 Hz, 2H), 7.60-7.55 (m, 3H), 7.53-7.48 (m, 1H), 7.35 (d, J=8.1 Hz, 2H), 7.15 (t, J=6.7 Hz, 1H), 2.47 (s, 3H);
$^{13}$C NMR (125 MHz, CDCl$_3$) δ=151.8, 149.4, 145.4, 140.0, 132.7, 132.0, 130.0, 129.9, 129.5, 129.4, 129.3, 128.5, 122.0, 117.2, 115.3, 21.4

10-3. (E)-3-(Phenyldiazenyl)-2-(p-tolyl)imidazo[1,2-a]pyridine $^1$H NMR (500 MHz, CDCl$_3$) δ=10.03-9.98 (m, 1H), 8.36 (d, J=8.2 Hz, 2H), 7.89-7.87 (m, 2H), 7.78 (d, J=8.8 Hz, 1H), 7.54-7.47 (m, 3H), 7.42-7.38 (m, 1H), 7.36 (d, J=7.9 Hz, 2H), 7.08-7.05 (m, 1H), 2.46 (s, 3H);
$^{13}$C NMR (125 MHz, CDCl$_3$) δ=153.8, 150.7, 145.9, 139.5, 131.9, 130.1, 129.9, 129.5, 129.4, 129.3, 129.1, 122.0, 117.2, 115.2, 21.4

10-4. (E)-2-(p-Tolyl)-3-(p-tolyldiazenyl)imidazo[1,2-a]pyridine $^1$H NMR (500 MHz, CDCl$_3$) δ=10.04 (d, J=6.9 Hz, 1H), 8.37 (d, J=8.1 Hz, 2H), 7.95 (d like, J=7.6 Hz, 1H), 7.80 (d, J=8.2 Hz, 2H), 7.57 (t, J=7.8 Hz, 1H), 7.37 (d, J=7.9 Hz, 2H), 7.33 (d, J=8.1 Hz, 2H), 7.14 (t, J=6.8 Hz, 1H), 2.46 (d like, J=2.7 Hz, 6H);
$^{13}$C NMR (125 MHz, CDCl$_3$) δ=151.8, 150.1, 145.7, 139.6, 139.2, 131.8, 130.3, 129.8, 129.7, 129.3, 129.2, 129.1, 121.9, 117.2, 114.9, 21.4, 21.3

10-5. (E)-2-(4-Methoxyphenyl)-3-(phenyldiazenyl)imidazo[1,2-a]pyridine $^1$H NMR (500 MHz, CDCl$_3$) δ=10.07-10.01 (m, 1H), 8.49-8.42 (m, 2H), 7.91-7.86 (m, 2H), 7.84 (d, J=8.8 Hz, 1H), 7.57-7.50 (m, 3H), 7.43-7.38 (m, 1H), 7.13-7.06 (m, 3H), 3.92 (s, 3H);
$^{13}$C NMR (125 MHz, CDCl$_3$) δ=160.8, 153.8, 150.6, 146.0, 131.7, 131.3, 129.4, 129.3, 129.1, 125.6, 121.9, 117.0, 114.9, 113.9, 55.3

10-6. (E)-2-(4-Methoxyphenyl)-3-(p-tolyldiazenyl)imidazo[1,2-a]pyridine $^1$H NMR (500 MHz, CDCl$_3$) δ=10.03 (d, J=6.9 Hz, 1H), 8.48-8.41 (m, 2H), 7.86 (d like, J=8.5 Hz, 1H), 7.79 (d, J=8.2 Hz, 2H), 7.53 (t, J=7.9 Hz, 1H), 7.33 (d, J=7.9 Hz, 2H), 7.12-7.05 (m, 3H), 3.92 (s, 3H), 2.45 (s, 3H);
$^{13}$C NMR (125 MHz, CDCl$_3$) δ=160.6, 151.7, 149.8, 145.7, 139.3, 131.5, 131.2, 129.6, 129.2, 129.0, 125.7, 121.7, 116.9, 114.6, 113.8, 55.2, 21.3

10-7. (E)-6-Phenyl-5-(phenyldiazenyl)imidazo[2,1-b]thiazole $^1$H NMR (500 MHz, CDCl$_3$) δ=8.59 (d, J=4.4 Hz, 1H), 8.41-8.37 (m, 2H), 7.89-7.87 (m, 2H), 7.54-7.50 (m, 4H), 7.46-7.40 (m, 2H), 6.99 (d, J=4.4 Hz, 1H);
$^{13}$C NMR (125 MHz, CDCl$_3$) δ=154.2, 153.2, 149.9, 135.8, 133.0, 129.7, 129.1, 129.0, 128.9, 128.5, 123.1, 122.2, 113.3

10-8. (E)-6-Phenyl-5-(p-tolyldiazenyl)imidazo[2,1-b]thiazole $^1$H NMR (500 MHz, CDCl$_3$) δ=8.58-8.53 (m, 1H), 8.43-8.35 (m, 2H), 7.82-7.74 (m, 2H), 7.51 (t, J=7.7 Hz, 2H), 7.43 (t, J=7.3 Hz, 1H), 7.31 (d, J=7.9 Hz, 2H), 6.93 (t, J=4.4 Hz, 1H), 2.45 (s, 3H)
$^{13}$C NMR (125 MHz, CDCl$_3$) δ=153.9, 151.4, 149.3, 140.2, 135.9, 133.2, 129.8, 128.9, 128.8, 128.5, 123.1, 122.2, 113.1, 21.4

10-9. (E)-6-(4-Methoxyphenyl)-5-(phenyldiazenyl)imidazo[2,1-b]thiazole $^1$H NMR (500 MHz, CDCl$_3$) δ=8.53 (dd, J=1.8, 4.3 Hz, 1H), 8.35 (d, J=8.9 Hz, 2H), 7.84 (d, J=8.1 Hz, 2H), 7.50 (t, J=7.7 Hz, 2H), 7.39 (t, J=7.3 Hz, 1H), 7.04 (d, J=8.9 Hz, 2H), 6.89 (dd, J=1.4, 4.4 Hz, 1H), 3.89 (s, 3H);
$^{13}$C NMR (125 MHz, CDCl$_3$) δ=160.5, 154.5, 153.4, 150.3, 135.4, 130.4, 129.4, 129.1, 125.9, 123.2, 122.1, 114.1, 112.7, 55.3

10-10. (E)-6-(4-Methoxyphenyl)-5-(p-tolyldiazenyl)imidazo[2,1-b]thiazole $^1$H NMR (500 MHz, CDCl$_3$) δ=8.54-8.47 (m, 1H), 8.34 (d, J=8.8 Hz, 2H), 7.73 (d, J=8.1 Hz, 2H), 7.31-7.26 (m, 2H), 7.03 (d, J=8.8 Hz, 2H), 6.90-6.82 (m, 1H), 3.89 (s, 3H), 2.43 (s, 3H);
$^{13}$C NMR (125 MHz, CDCl$_3$) δ=160.4, 154.1, 151.4, 149.6, 139.8, 135.4, 130.3, 129.7, 126.0, 123.2, 122.0, 114.0, 112.5, 55.3, 21.4

10-11. (E)-1-(Phenyldiazenyl) naphthalen-2-ol $^1$H NMR (200 MHz, CDCl$_3$) δ=8.54 (d, J=8.2 Hz, 1H), 7.76-7.65 (m, 3H), 7.60-7.29 (m, 6H), 6.85 (d, J=9.4 Hz, 1H);
$^{13}$C NMR (50 MHz, CDCl$_3$) δ=172.0, 144.7, 140.1, 133.6, 130.0, 129.6, 128.8, 128.6, 128.0, 127.4, 125.7, 124.8, 121.7, 118.5

10-12. (E)-1-(p-Tolyldiazenyl) naphthalen-2-ol $^1$H NMR (500 MHz, CDCl$_3$) δ=8.62 (d, J=8.4 Hz, 1H), 7.75 (d, J=9.3 Hz, 1H), 7.71-7.67 (m, 2H), 7.64 (d, J=7.9 Hz, 1H), 7.57 (ddd, J=1.3, 7.1, 8.3 Hz, 1H), 7.41 (ddd, J=1.2, 7.0, 7.9 Hz, 1H), 7.30 (d, J=7.9 Hz, 2H), 6.96 (d, J=9.3 Hz, 1H), 2.43 (s, 3H);
$^{13}$C NMR (125 MHz, CDCl$_3$) δ=168.3, 143.5, 138.8, 138.3, 133.5, 130.1, 129.7, 128.5, 128.4, 128.0, 125.3, 123.9, 121.6, 119.1, 21.2

10-13. Iodobenzene $^1$H NMR (500 MHz, CDCl$_3$) δ=7.73 (d, J=8.1 Hz, 2H), 7.35 (dt, J=0.8, 7.5 Hz, 1H), 7.16-7.09 (m, 2H);
$^{13}$C NMR (125 MHz, CDCl$_3$) δ=137.3, 130.1, 127.3, 94.4

10-14. 1-Iodo-4-methylbenzene $^1$H NMR (500 MHz, CDCl$_3$) δ=7.57 (d, J=8.2 Hz, 2H), 6.94 (d, J=7.8 Hz, 2H), 2.30 (s, 3H);
$^{13}$C NMR (125 MHz, CDCl$_3$) δ=137.4, 137.2, 131.1, 90.2, 21.0

10-15. Chlorobenzene $^1$H NMR (500 MHz, CDCl$_3$) δ=7.29-7.25 (m, 2H), 7.24-7.20 (m, 2H), 7.19-7.15 (m, 1H);
$^{13}$C NMR (126 MHz, CDCl$_3$) δ=134.2, 129.7, 128.6, 126.4

10-16. 1-Chloro-4-methylbenzene $^1$H NMR (500 MHz, CDCl$_3$) δ=7.28 (d, J=8.2 Hz, 2H), 7.16 (d, J=8.1 Hz, 2H), 2.38 (s, 3H);
$^{13}$C NMR (125 MHz, CDCl$_3$) δ=136.2, 131.1, 130.3, 128.2, 20.8

10-17. 2-Phenylfuran $^1$H NMR (500 MHz, CDCl$_3$) δ=7.74-7.66 (m, 2H), 7.52-7.45 (m, 1H), 7.40 (t, J=7.7 Hz, 2H), 7.30-7.25 (m, 1H), 6.67 (d, J=3.4 Hz, 1H), 6.49 (dd, J=1.8, 3.4 Hz, 1H);
$^{13}$C NMR (125 MHz, CDCl$_3$) δ=154.0, 142.0, 130.9, 128.6, 127.3, 123.8, 111.6, 104.9

10-18. 2-(p-Tolyl)furan $^1$H NMR (500 MHz, CDCl$_3$) δ=7.60 (d, J=8.2 Hz, 2H), 7.47 (s, 1H), 7.22 (d, J=7.9 Hz, 2H), 6.62 (d, J=3.2 Hz, 1H), 6.48 (dd, J=1.6, 3.1 Hz, 1H), 2.39 (s, 3H);
$^{13}$C NMR (125 MHz, CDCl$_3$) δ=154.2, 141.6, 137.1, 129.3, 128.2, 123.7, 111.5, 104.2, 21.1

10-19. Phenyl(p-tolyl)sulfane $^1$H NMR (500 MHz, CDCl$_3$) δ=7.32 (d, J=8.2 Hz, 2H), 7.29-7.26 (m, 4H), 7.23-7.18 (m, 1H), 7.15 (d, J=7.9 Hz, 2H), 2.36 (s, 3H); $^{13}$C NMR (125 MHz, CDCl$_3$) δ=137.5, 137.1, 132.2, 131.3, 130.0, 129.8, 129.0, 126.4, 21.1

10-20. Di-p-tolylsulfane $^1$H NMR (500 MHz, CDCl$_3$) δ=7.25 (d, J=8.1 Hz, 4H), 7.12 (d, J=7.9 Hz, 4H), 2.34 (s, 6H);
$^{13}$C NMR (125 MHz, CDCl$_3$) δ=136.8, 132.7, 131.0, 129.8, 21.0

10-21. Azidobenzene $^1$H NMR (500 MHz, CDCl$_3$) δ=7.39-7.34 (m, 2H), 7.18-7.13 (m, 1H), 7.07-7.02 (m, 2H);
$^{13}$C NMR (75 MHz, CDCl$_3$) δ=139.9, 129.7, 124.8, 119.0

10-22. 1-Azido-4-methylbenzene $^1$H NMR (500 MHz, CDCl$_3$) δ=7.16 (d, J=7.9 Hz, 2H), 6.93 (d, J=8.4 Hz, 2H), 2.34 (s, 3H);
$^{13}$C NMR (75 MHz, CDCl$_3$) δ=137.1, 134.5, 130.3, 118.8, 20.7

Experimental Example 1

Screening Method Using Parallel Synthesizer of Compound Library

As can be seen in FIG. 1, the flow parallel synthesizer according to the present invention is ready to demonstrate a wide range of flow chemistries by pre-forming the efficient parameter screening and synthesis library of aryldiazonium salts with model chemistry. First, 16×6 conditions of diazonium salt-based flow reactions were screened in parallel to find optimal conditions using benzene diazonium tetrafluoroborate (a) as the simplest and most stable diazonium precursor. In this experiment, a 0.77M solution of DMSO was pumped through two first inlets (D1 and D2, FIG. 5) at 6 different flow velocities ranging from 10.56 to 0.35 mL/min by using an HPLC pump.

Figure 3A:
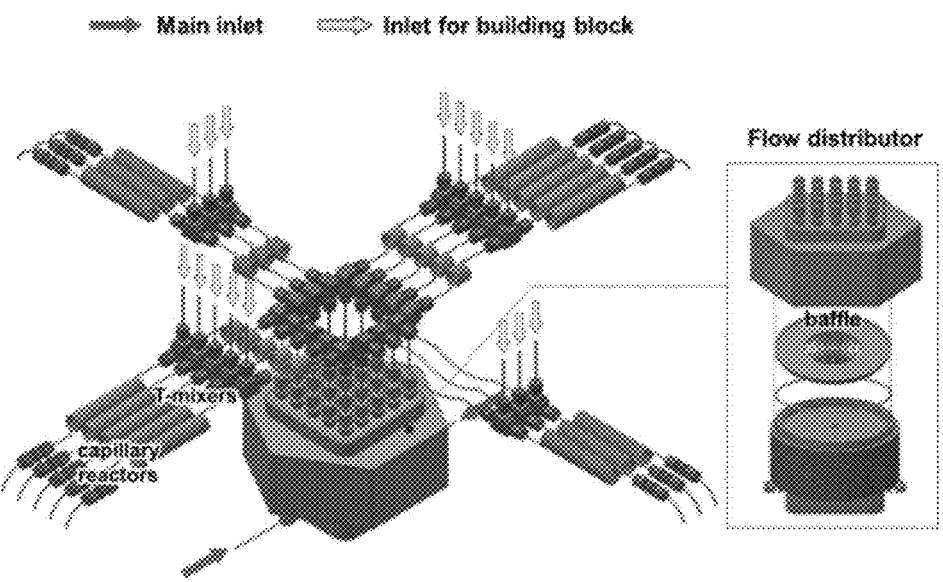
FIGS. 3A and 3B are block diagrams of the parallel synthesizer according to the present invention.
Figure 3B:
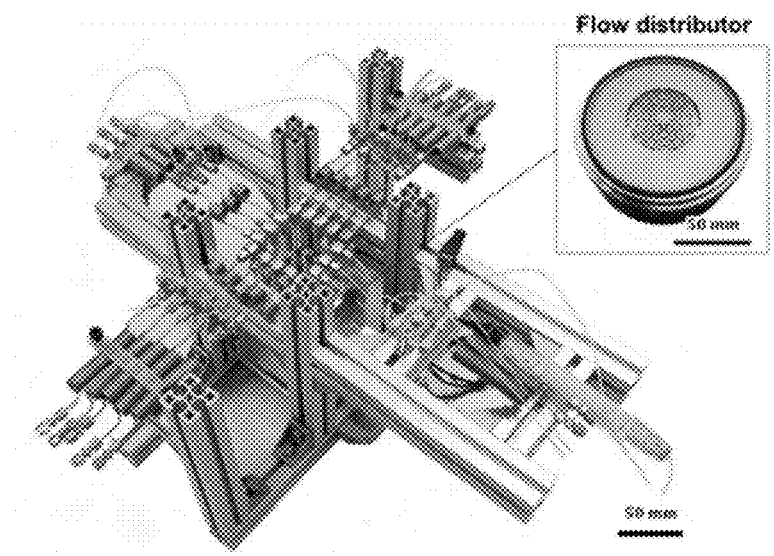

The flow of a diazonium solution was uniformly distributed across 16 individual stainless-steel capillaries of the flow synthesizer with high reliability as mentioned above. In addition, the capillaries were connected with a T-shaped mixer at a flow velocity in a range of 0.66 to 0.033 m/min corresponding to 1/16 of the initial flow velocity. The flow of the diazonium solution was merged with the flow of the second reactant (building block) including other chemical components in a range of 0.66 to 0.033 m/min through 16 inlets (I1 to I16) as illustrated in FIG. 3.

Figure 4A:
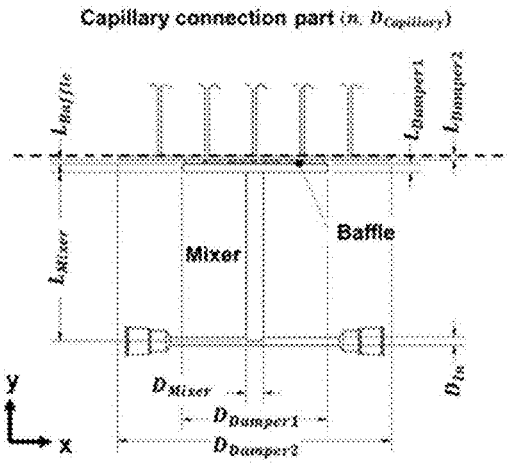
FIGS. 4A and 4B are cross-sectional views of the parallel synthesizer according to the present invention.
Figure 4B:
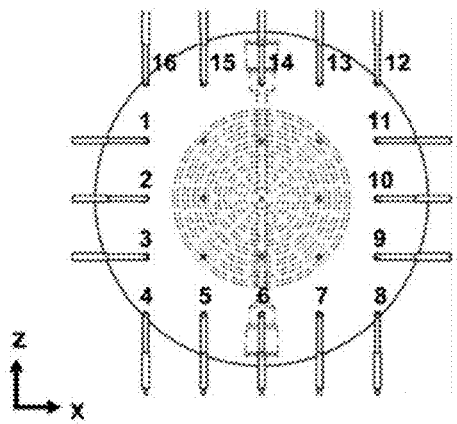

In order to show the aromatic substitution reaction, the second reactant of the second inlet I1 included a 3.85M furan solution and 5 mol % Eosin Y (6) to show the photochemical reaction, and in order to show the aromatic substitution reaction, I2 included a 0.77M CuCl solution (2), I3 included a 0.77M KI solution (1), I9 included a 0.77M NaN$_3$ solution (3), I10 included a 0.77M p-thiocresol sodium salt solution (4), and I11 included a pure solution of furan containing 5 mol % of a 4-aminomorpholine catalyst. The second inlets I12 to I16 included a mixture of β-naphthol (7) at 0.64, 0.51, 0.38, 0.32 and 0.26 M and NaOH for the concentration screening of azo-dye based carbocycles. I4 to I8 included 0.51 M imidazopyridine (8, 9, 10) and imidazothiazole derivatives (11, 12) solutions for the azo-coupling reactions of heterocycles. Various bond-forming reactions mixing the two reagents occurred simultaneously in 16 capillaries via the SNAr and radical pathways in multiple modes. Finally, the 16 second reactants (building blocks) introduced at the inlets I1 to I16 were reacted with benzene diazonium tetrafluoroborate (a) at a single concentration (0.77M) at 6 different residence times of 30, 60, 120, 300, 600 and 900 seconds, and it allowed for synthetic screening under 16×6 different conditions. The isolated yield of each sample collected during the optimization process is shown in FIG. 4.

When the experimental setup including the pump and the feed solution was prepared in the parallel synthesizer, 16 samples were obtained each time by flowing out the capillary reactors R1 to R16 at a specific flow velocity. After screening 6 different residence times by simply changing the flow velocity, a total of 16×8=96 samples were collected to find the optimal parameters at the reaction time and concentration showing the highest yield as summarized in Table 3.

Screening Results Using the Parallel Synthesizer of Compound Library

The aromatic substitution reaction (C—C, C—N, C—S) proceeded with a residence time of 60 seconds to obtain the desired products in good yield (55% to 86%), and it included the reaction of benzene diazonium tetrafluoroborate (a) with furan (5) in capillary R11 to provide product (a5), NaN$_3$ (3) in capillary R9 to provide product (a3) and R—SNa (4) in capillary R10 to provide product (a4). Similarly, KI (1) in capillary R3 provided product (a1), CuCl (2) in capillary R2 provided product (a2) to form C-halogen bonds based on the aromatic substitution of diazonium, and 30 seconds and 120 seconds were required to provide 65% and 57% yields of the desired products. The low yield of chlorobenzene is justified by the formation of a small amount of the Gomberg-Bachmann product, and a common side reaction which generally occurs with the use of CuCl forms an aryl radical in charge of the formation of ortho/para-chloro-1,1'-biphenyl. In contrast, aromatic substitution via organic photoredox catalysis between diazonium and furan (a6) in capillary R1 occurred with a residence time of 600 seconds in the presence of a green LED, delivering the arylated product in 54% yield. In addition, the azo-coupling reaction of carbocycles and β-napthol (7) at five different concentrations (0.64, 0.51, 0.38, 0.32 and 0.26M) in capillaries R12 to R16 provided product (a7) in 71% to 74% yields, respectively. Finally, the azo-coupling reaction of imidazopyridine (8 to 10), which is a heterocycle in capillaries R4 to R6, provided products (a8 to a10) in 78%, 79% and 83% yields, and imidazothiazoles (11 and 12) were used in capillaries R7 and R8 to provide products (a11 and a12) in 74% and 78% yields at a residence time of 60 seconds.

Pre-decomposition of the diazonium reagent results in a lower yield than that of a single capillary reactor because of the long stay of nitrogen gas, which is produced in the distributor, in the storage space (refer to Table 3). Fortunately, since the unique design of the system according to the invention allows for an even distribution of the gas/solution mixture, the overall flow distribution is not affected, as indicated in FIG. 7.

In addition, in the case of azo-dye synthesis, since capillaries (R12 to R16) were rarely clogged at high concentrations, concentration was considered as another important variable to be considered during the screening process. This problem was overcome by screening for five concentrations of β-naphthol (0.64, 0.51, 0.38, 0.32 and 0.26 M) for 6 residence times (30, 60, 120, 300, 600 and 900 seconds), and thus, 6×5=30 concentration-based data points were generated to determine the optimal concentrations needed to achieve excellent productivity. As a result, the highest yield of 74% of the Sudan dye was obtained at a concentration of 0.38M, compared to lower concentrations of 0.32 and 0.26 M where excess diazonium was pumped into the reaction, and some impurity formation was observed.

In addition to the above, due to low flow velocities, dye deposits were often precipitated, resulting in clogging in the capillaries. However, overall, when the capillaries were clogged at concentrations of 0.64 and 0.51 M or more, it was observed that the reactions proceeded without interruption in the remaining capillaries simply by reducing the initial inflow by 6.6% for each clogged capillary. In order to solve the chronic clogging problems of microreactors, it may be adjusted by maintaining a balanced flow of the second reactants (building blocks).

According to the present invention, the total time required to screen 16×δ=96 cases in terms of performance efficiency was about 60 minutes (based on steady state required for 6 different residence times), which was much less than performing in a batch mode. Therefore, it can be seen that the parallel synthesizer according to the present invention requires minimum labor and is cost-effective, user-friendly and very efficient in terms of screening.

Control of Reaction Time of Parallel Synthesizer of Compound Library

The results obtained from the screening data suggest that the flexibility of the flow parallel synthesizer may be improved by adjusting the system to select the residence time of each capillary according to the needs of the reaction. Three peristaltic pumps P1, P2 and P3 were connected to individual reactors R1, R2 and R3 in a way that the flow rate was controlled orthogonally. Three different types of reactions, such as iodination, chlorination and photochemical transformation, were performed at three residence times (600, 120 and 30 seconds) by applying the corresponding flow velocities of diazonium reagents (0.033, 0.17 and 0.66 mL/min, respectively).

Overall, in order to show the diversity of the flow parallel synthesizer, 6 sets of screenings (16×δ=96) were performed in which aromatic substitution-based and carbocycle-based azo-coupling and heterocycle-based azo-coupling were performed.

Next, by utilizing the above optimized conditions, with time intervals of 30 minutes including washing and stabilization steps to achieve steady state, the inventors of the present invention confirmed two sets of diazonium derivatives at a total flow velocity of 5.14 mL/min, ultimately leading to the generation of a library of (12×2=24) products, by using benzenediazonium tetrafluoroborate (a) and p-tolydiazonium tetrafluoroborate (b) at a total flow velocity of 5.14 m/min. The flow velocities of the three capillaries R1, R2 and R3 were set to (0.033, 0.17 and 0.66 mL/min), respectively. Capillaries R4 to R16 were set at a flow velocity of 0.33 m/min. Finally, the yields of each sample collected at each discharge unit of the parallel flow synthesizer are summarized in Table 1.

Finally, two different types of aryl diazonium were used to demonstrate the multiplex synthesis of a library of 24 compounds. In addition, the scale-out approach for the synthesis of Sudan dyes (a7 and b7) was demonstrated using five capillaries R12 to R16 with productivities of 6.8 g/h and 7.7 g/h, and it was shown that the parallel synthesizer according to the present invention may serve a dual role for screening as well as productivity.

Regardless of the reaction mixture analysis which is a bottleneck phenomenon that promotes screening proficiency, the main advantage of the flow parallel synthesizer according to the present invention is that it allows for the multiplex screening process efficiently at various substrate effects, concentrations and residence times. In general, the chemical performance of the flow parallel synthesizer was comparable to that of batch and a single capillary when the synthesis yields were compared (refer to Table 3). All automated flow platforms developed for advanced applications so far may only perform optimization of a single reaction set or all reaction variables at a given point in time to streamline the optimization process. However, according to the present invention, several synthesis chemistries are possible at once, but these are impossible with commercially available batch parallel synthesizers or reported automated flow platforms.

Although an exemplary embodiment of the present invention has been described above, the spirit of the present invention is not limited to the exemplary embodiment presented in the present specification, and those skilled in the art who understand the spirit of the present invention will be able to easily suggest other exemplary embodiments by modifying, changing, deleting or adding components within the scope of the same spirit, but this is also said to be within the scope of the present invention.

The invention claimed is:

1. A parallel synthesizer of a compound library, comprising:
   a first inlet unit through which a first reactant is introduced and at least one inlet is formed;
   a flow distributor connected to the first inlet unit and distributing the introduced first reactant in equal amounts, and formed with a damper and a baffle;
   a plurality of ducts connected to the flow distributor and through which the distributed first reactant passes, respectively;

a second inlet unit located at one side of the ducts and formed with an inlet through which a second reactant is introduced;

a plurality of reactors respectively connected to the ducts and in which a product is generated by a chemical reaction of the first reactant and the second reactant transported through the ducts; and a discharge unit formed on one side of the reactors to discharge the product, wherein the temperature and time of the chemical reaction can be independently controlled in each of the reactors, wherein each of the ducts is a coiled capillary thinner than the connected reactors, and wherein a flow velocity in the ducts is 0.3 to 0.5 mL/min.

2. The parallel synthesizer of claim 1, wherein the plurality of reactors are coiled capillaries.

3. The parallel synthesizer of claim 1, wherein the plurality of reactors can be independently controlled such that chemical reactions occur under different conditions.

4. The parallel synthesizer of claim 1, wherein the plurality of reactors comprise a temperature control unit.

5. The parallel synthesizer of claim 4, wherein the temperature control unit comprises a heating device or a cooling device.

6. The parallel synthesizer of claim 1, wherein the first inlet unit and the second inlet unit comprise a pump, and the pump introduces reactants into an inlet.

7. The parallel synthesizer of claim 6, wherein the pump is a syringe pump or a peristaltic pump.

8. The parallel synthesizer of claim 1, wherein the ducts further comprises a peristaltic pump at a position connected to the flow distributor to control the residence time of a compound in the ducts.

9. The parallel synthesizer of claim 1, wherein the ducts have a higher hydraulic pressure than the reactors.

10. A parallel synthesizer of a compound library, comprising:

a first inlet unit through which a first reactant is introduced and at least one inlet is formed;

a flow distributor connected to the first inlet unit and distributing the introduced first reactant in equal amounts, and formed with a damper and a baffle;

a plurality of ducts connected to the flow distributor and through which the distributed first reactant passes, respectively;

a second inlet unit located at one side of the ducts and formed with an inlet through which a second reactant is introduced;

a plurality of reactors respectively connected to the ducts and in which a product is generated by a chemical reaction of the first reactant and the second reactant transported through the ducts; and a discharge unit formed on one side of the reactors to discharge the product, wherein the temperature and time of the chemical reaction can be independently controlled in each of the reactors, wherein each of the ducts is a coiled capillary thinner than the connected reactors, wherein a flow velocity in the ducts is 0.3 to 0.5 mL/min, wherein the first reactant is an aryldiazonium salt, and wherein the aryldiazonium salt comprises a cation represented by Chemical Formula 1 below:

[Chemical Formula 1]

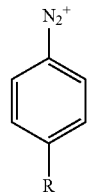

In Chemical Formula 1 above, R is hydrogen, a hydroxyl group, an ether group, a halogen atom, a carbonyl group, a nitro group, a naphthyl group, a cyano group, an amino group, an amidino group, hydrazine, hydrazone, a carboxyl group, a sulfonic acid group, a phosphoric acid group, an alkyl group having 1 to 12 carbon atoms, an alkenyl group having 1 to 12 carbon atoms, an alkynyl group having 1 to 12 carbon atoms, an aryl group having 6 to 10 carbon atoms, or an arylalkyl group having 7 to 10 carbon atoms.

* * * * *